(12) United States Patent
Pan et al.

(10) Patent No.: US 7,091,323 B2
(45) Date of Patent: Aug. 15, 2006

(54) HUMAN TIMP-1 ANTIBODIES

(75) Inventors: Clark Pan, Castro Valley, CA (US);
Andreas M. Knorr, Erkrath (DE);
Michael Schauer, Wuppertal (DE);
Claudia Hirth-Dietrich, Wuppertal (DE); Sabine Kraft, Planegg (DE);
Barbara Krebs, Bergisch Gladbach (DE)

(73) Assignees: Bayer Corporation, Pittsburgh, PA (US); Bayer Aktiengesellschaft, Leverkusen (DE)

( * ) Notice: Subject to any disclaimer, the term of this patent is extended or adjusted under 35 U.S.C. 154(b) by 352 days.

(21) Appl. No.: 10/128,520

(22) Filed: Apr. 24, 2002

(65) Prior Publication Data

US 2004/0105862 A1 Jun. 3, 2004

Related U.S. Application Data

(60) Provisional application No. 60/285,683, filed on Apr. 24, 2001.

(51) Int. Cl.
*A61K 39/395* (2006.01)
*C12P 21/08* (2006.01)
*C07K 16/40* (2006.01)

(52) U.S. Cl. .................... 530/388.15; 530/387.3; 530/388.2; 530/388.26; 424/142.1; 424/146.1; 424/133.1

(58) Field of Classification Search ............. 530/387.1, 530/388.15, 387.3, 388.2, 388.26; 424/142.1, 424/146.1, 133.1
See application file for complete search history.

(56) References Cited

U.S. PATENT DOCUMENTS

| | | | |
|---|---|---|---|
| 5,324,634 A | 6/1994 | Zucker | |
| 5,338,661 A | 8/1994 | Jensenius et al. | |
| 5,674,754 A | 10/1997 | Ahrens et al. | |
| 5,877,289 A | 3/1999 | Thorpe et al. | |
| 6,004,555 A | 12/1999 | Thorpe et al. | |
| 6,036,955 A | 3/2000 | Thorpe et al. | |
| 6,093,399 A | 7/2000 | Thorpe et al. | |

FOREIGN PATENT DOCUMENTS

| | | |
|---|---|---|
| JP | 8134098 | 5/1996 |
| WO | WO 00/20642 | 4/2000 |
| WO | WO 00/62070 | 10/2000 |

OTHER PUBLICATIONS

Reed, MJ et al. J. Cell Biochem. [Apr. 1, 2000] 77(1): 116-126.*
Paul W. E., editor. Fundamental Immunology, 3rd edition. Raven Press, New York. [1993] pp. 292-295.*
Holten-Andersen et al., "Characterization of Monoclonal Antibodies to Tissue Inhibitor of Metalloproteinases-1", *Journal of Clinical Ligand Assay*, vol. 25(1), pp. 87-90, (2002).
Krebs et al., "High-throughput generation and engineering of recombinant human antibodies", *Journal of Immunological Methods*, vol. 254(1-2), pp. 67-84, (2001).
Lu et al., "Immunological Quantitation of Levels of Tissue Inhibitor of Metalloproteinase-1 in Human Colon Cancer", *Cancer Research*, vol. 51(23), pp. 6231-6235 (1991).
Parsons et al, "Antifibrotic Effects of a Tissue Inhibitor of Metalloproteinase-1 Antibody on Established Liver Fibrosis in Rats", *Hepatology*, vol. 40(5), pp. 1106-1115 (2004).
Wozniak et al., "Expression of TIMP-1 in *Pichia pastoris*. Selection of an anti-TIMP-1 specific single-chain Fv antibody from a large non-immune library", *Clinica Chimica Acta*, vol. 327(1-2), pp. 171-179, (2003).
L. Guedez et al., "In Vitro Suppression of Programmed Cell Death of B Cells by Tissue Inhibitor of Metalloproteinases-1", The Journal of Clinical Investigation, vol. 102, No. 11, Dec. 1998, pp. 2002-2010.
M.N. Holten-Andersen et al., "Measurement of the Noncomplexed Free Fraction of Tissue Inhibitor of Metalloproteinases 1 in Plasma by Immunoassy", Clinical Chemistry, vol. 48, No. 8, 2002, pp. 1305-1313.

* cited by examiner

*Primary Examiner*—Christina Chan
*Assistant Examiner*—F. Pierre VanderVegt
(74) *Attorney, Agent, or Firm*—DLA Piper Rudnick Gray Cary US LLP

(57) ABSTRACT

Human antibodies that bind to TIMP-1 can be used as reagents to diagnose and treat disorders in which TIMP-1 is elevated, such as liver fibrosis, alcoholic liver disease, cardiac fibrosis, acute coronary syndrome, lupus nephritis, glomerulosclerotic renal disease, benign prostate hypertrophy, colon cancer, lung cancer, and idiopathic pulmonary fibrosis.

12 Claims, 19 Drawing Sheets

Sequence Summary HuCAL Libraries scFv1, scFv2, scFv3 and Fab1

VL

| Position | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | a | b | c | d | e | f | 1 | 2 | 3 | 4 |
|---|---|---|---|---|---|---|---|---|---|---|---|---|---|---|---|---|---|---|---|---|---|---|---|---|---|---|---|---|---|---|---|---|---|---|---|---|---|---|---|---|
|  | EcoRV | | | | | | | | | | | | | | | BanII | | | | | | | | | | | | | | | | | | PstI | | | | | | |
| VLk1 | D | I | Q | M | T | Q | S | P | S | S | L | S | A | S | V | G | D | R | V | T | I | T | C | R | A | S | Q | G | I | S | . | . | . | . | . | . | S | Y | L | A |
| VLk2 | D | I | V | M | T | Q | S | P | L | S | L | P | V | T | P | G | E | P | A | S | I | S | C | R | S | S | Q | S | L | L | H | S | . | . | . | N | G | Y | N | . |
| VLk3 | D | I | V | L | T | Q | S | P | A | T | L | S | L | S | P | G | E | R | A | T | L | S | C | R | A | S | Q | S | V | S | . | . | . | . | . | . | S | Y | L | A |
| VLk4 | D | I | V | M | T | Q | S | P | D | S | L | A | V | S | L | G | E | R | A | T | I | N | C | R | S | S | Q | S | V | L | Y | S | S | N | N | K | N | Y | L | A |
| VLλ1 | D | I | V | L | T | Q | . | P | P | S | . | S | V | S | G | A | P | G | Q | R | V | T | I | S | C | S | G | S | S | S | N | I | G | S | . | . | N | Y | V | S |
| VLλ2 | D | I | A | L | T | Q | . | P | A | S | . | V | S | G | S | P | G | Q | S | I | T | I | S | C | T | G | T | S | S | D | V | G | G | Y | . | . | N | Y | V | S |
| VLλ3 | D | I | E | L | T | Q | . | P | P | S | . | V | S | V | A | P | G | Q | T | A | R | I | S | C | S | G | D | A | L | G | D | . | . | . | . | . | K | Y | A | S |
|  | EcoRV | | | | | | | | | | | | | | | SexAI | | | | | | | | | BssSI | | | | | | | | | | | | | | | |

VH

| Position | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | a | b | 2 | 3 | 4 | 5 | 6 | 7 | 8 |
|---|---|---|---|---|---|---|---|---|---|---|---|---|---|---|---|---|---|---|---|---|---|---|---|---|---|---|---|---|---|---|---|---|---|---|---|---|---|---|---|
|  | MfeI | | | | | | | | | | | | | | | | | | | | | | | | BspEI | | | | | | | | | | | | | | |
| VH1A | Q | V | Q | L | V | Q | S | G | A | E | V | K | K | P | G | S | S | V | K | V | S | C | K | A | S | G | G | T | F | S | . | . | S | Y | A | I | S | W | V | R |
| VH1B | Q | V | Q | L | V | Q | S | G | A | E | V | K | K | P | G | A | S | V | K | V | S | C | K | A | S | G | Y | T | F | T | . | . | S | Y | R | M | H | W | V | R |
| VH2 | Q | V | Q | L | K | E | S | G | P | A | L | V | K | P | T | Q | T | L | T | L | T | C | T | F | S | G | F | S | L | S | T | S | G | V | G | V | G | W | I | R |
| VH3 | Q | V | Q | L | V | E | S | G | G | G | L | V | Q | P | G | G | S | L | R | L | S | C | A | A | S | G | F | T | F | S | . | . | S | Y | A | M | S | W | V | R |
| VH4 | Q | V | Q | L | Q | E | S | G | P | G | L | V | K | P | S | E | T | L | S | L | T | C | T | V | S | G | G | S | I | S | . | . | S | Y | Y | W | S | W | I | R |
| VH5 | Q | V | Q | L | V | Q | S | G | A | E | V | K | K | P | G | E | S | L | K | I | S | C | K | G | S | G | Y | S | F | T | . | . | S | Y | W | I | G | W | V | R |
| VH6 | Q | V | Q | L | Q | Q | S | G | P | G | L | V | K | P | S | Q | T | L | S | L | T | C | A | I | S | G | D | S | V | S | . | . | S | N | S | A | A | W | N | . |

FIG. 1

FIG. 1, cnt.

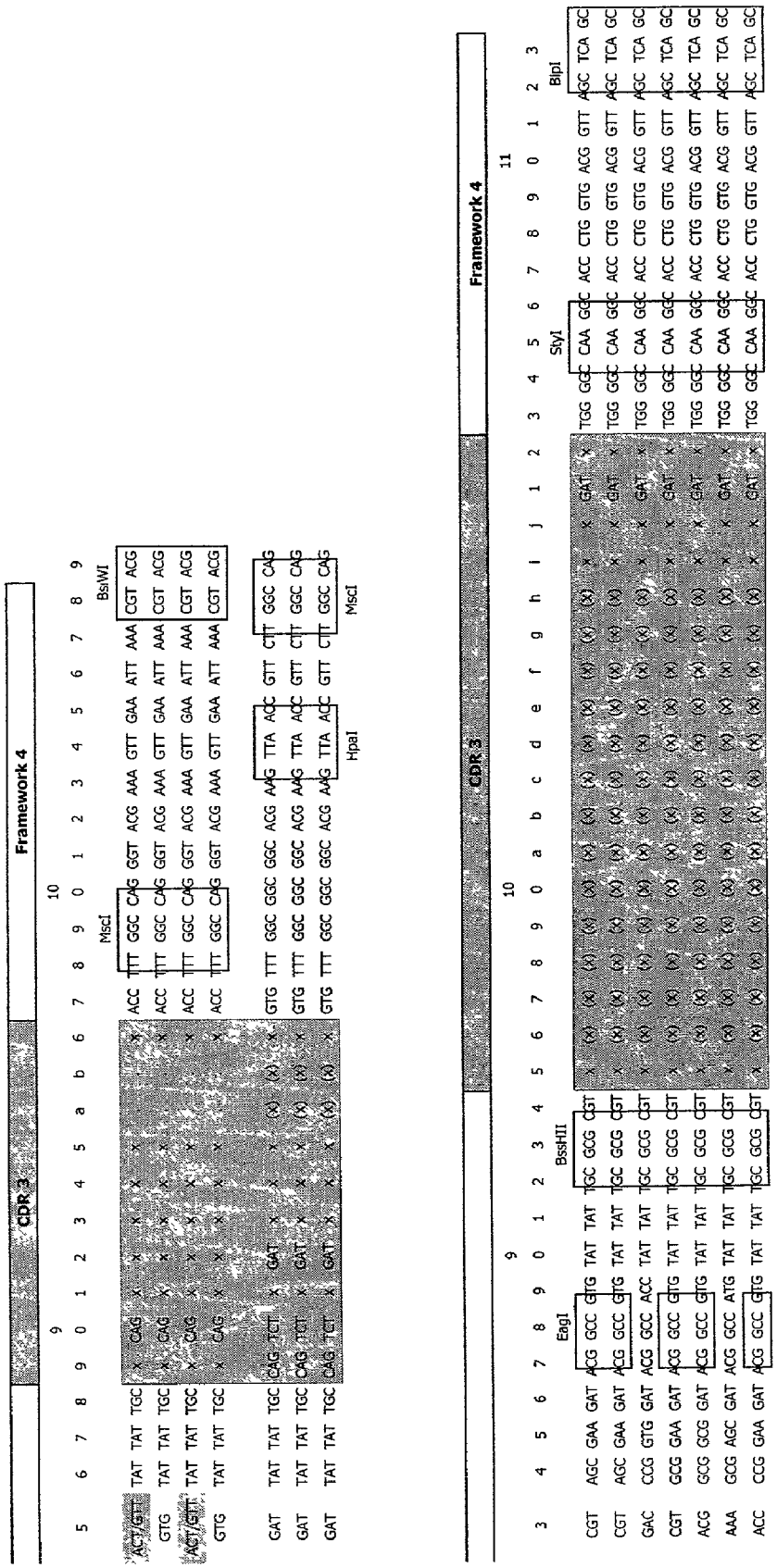
FIG. 2, cont.

FIG. 5

```
TIMP1_human 135850    1 CTCVPPHPQTAFCNSDLVIRAKFVGTPEVNQTTLYQRYEIKMTKMYKGFQ   50
TIMP1_rat   1174697   1 CSCAPTHPQTAFCNSDLVIRAKFMGSPEIIETTLYQRYEIKMTKMLKGFD   50
                        * * *********** **.*.** . .*** . ********* ****

TIMP1_human 135850   51 ALGDAADIRFVYTPAMESVCGYFHRSHNRSEEFLIAGKLQDGLLHITTCS  100
TIMP1_rat   1174697  51 AVGNATGFRFAYTPAMESLCGYVHKSQNRSEEFLIAGRLRNGNLHITACS  100
                        *.*.*. * **.*****.*** *.*.**********.*.* *****.**

TIMP1_human 135850  101 FVAPWNSLSLAQRRGFTKTYTVGCEECTVFPCLSIPCKLQSGTHCLWTDQ  150
TIMP1_rat   1174697 101 FLVPWHNLSPAQQKAFVKTYSAGCCGVCTVFPCSAIPCKLESDSHCLWTDQ 150
                        *.****..** **..*.***.. ** ******* ******.* .******

TIMP1_human 135850  151 LLQGSEKGFQSRHLACLPREPGLCTWQSLRSQIA           184
TIMP1_rat   1174697 151 ILMGSEKGYQSDHFACLPRNPDLCTWQYLGVSMTRSLPLAKAEA 194
                        .* *****.**.*.*****.*..**** *  *
```

SEQUENCE LISTING

```
<160> NUMBER OF SEQ ID NOS: 381

<210> SEQ ID NO 1
<211> LENGTH: 4
<212> TYPE: PRT
<213> ORGANISM: Homo sapiens

<400> SEQUENCE: 1

Phe Met Asp Ile
 1

<210> SEQ ID NO 2
<211> LENGTH: 4
<212> TYPE: PRT
<213> ORGANISM: Homo sapiens

<400> SEQUENCE: 2

Gly Phe Asp Tyr
 1

<210> SEQ ID NO 3
<211> LENGTH: 4
<212> TYPE: PRT
<213> ORGANISM: Homo sapiens

<400> SEQUENCE: 3

Phe Leu Asp Ile
 1

<210> SEQ ID NO 4
<211> LENGTH: 8
<212> TYPE: PRT
<213> ORGANISM: Homo sapiens

<400> SEQUENCE: 4

Thr Phe Pro Ile Asp Ala Asp Ser
 1               5

<210> SEQ ID NO 5
<211> LENGTH: 5
<212> TYPE: PRT
<213> ORGANISM: Homo sapiens

<400> SEQUENCE: 5
```

```
Gly His Val Asp Tyr
 1               5

<210> SEQ ID NO 6
<211> LENGTH: 9
<212> TYPE: PRT
<213> ORGANISM: Homo sapiens

<400> SEQUENCE: 6

Tyr Trp Arg Gly Leu Ser Phe Asp Ile
 1               5

<210> SEQ ID NO 7
<211> LENGTH: 4
<212> TYPE: PRT
<213> ORGANISM: Homo sapiens

<400> SEQUENCE: 7

Phe Phe Asp Tyr
 1

<210> SEQ ID NO 8
<211> LENGTH: 12
<212> TYPE: PRT
<213> ORGANISM: Homo sapiens

<400> SEQUENCE: 8

Gly Leu Tyr Trp Ala Val Tyr Pro Tyr Phe Asp Phe
 1               5                  10

<210> SEQ ID NO 9
<211> LENGTH: 11
<212> TYPE: PRT
<213> ORGANISM: Homo sapiens

<400> SEQUENCE: 9

Leu Asp Thr Tyr Tyr Pro Asp Leu Phe Asp Tyr
 1               5                  10

<210> SEQ ID NO 10
<211> LENGTH: 7
<212> TYPE: PRT
<213> ORGANISM: Homo sapiens

<400> SEQUENCE: 10

Thr Tyr Tyr Tyr Phe Asp Ser
 1               5

<210> SEQ ID NO 11
<211> LENGTH: 11
<212> TYPE: PRT
<213> ORGANISM: Homo sapiens

<400> SEQUENCE: 11

Tyr Met Ala Tyr Met Ala Glu Ala Ile Asp Val
 1               5                  10

<210> SEQ ID NO 12
<211> LENGTH: 17
<212> TYPE: PRT
<213> ORGANISM: Homo sapiens

<400> SEQUENCE: 12

Leu Val Gly Ile Val Gly Tyr Lys Pro Asp Glu Leu Leu Tyr Phe Asp
```

-continued

```
                 1               5                  10                  15
Val

<210> SEQ ID NO 13
<211> LENGTH: 9
<212> TYPE: PRT
<213> ORGANISM: Homo sapiens

<400> SEQUENCE: 13

Tyr Gly Ala Tyr Phe Gly Leu Asp Tyr
 1               5

<210> SEQ ID NO 14
<211> LENGTH: 9
<212> TYPE: PRT
<213> ORGANISM: Homo sapiens

<400> SEQUENCE: 14

Gly Tyr Ala Asp Ile Ser Phe Asp Tyr
 1               5

<210> SEQ ID NO 15
<211> LENGTH: 7
<212> TYPE: PRT
<213> ORGANISM: Homo sapiens

<400> SEQUENCE: 15

Tyr Tyr Leu Leu Leu Asp Tyr
 1               5

<210> SEQ ID NO 16
<211> LENGTH: 16
<212> TYPE: PRT
<213> ORGANISM: Homo sapiens

<400> SEQUENCE: 16

Trp Ser Asp Gln Ser Tyr His Tyr Tyr Trp His Pro Tyr Phe Asp Val
 1               5                  10                  15

<210> SEQ ID NO 17
<211> LENGTH: 7
<212> TYPE: PRT
<213> ORGANISM: Homo sapiens

<400> SEQUENCE: 17

Leu Ile Gly Tyr Phe Asp Leu
 1               5

<210> SEQ ID NO 18
<211> LENGTH: 12
<212> TYPE: PRT
<213> ORGANISM: Homo sapiens

<400> SEQUENCE: 18

Leu Thr Asn Tyr Phe Asp Ser Ile Tyr Tyr Asp His
 1               5                  10

<210> SEQ ID NO 19
<211> LENGTH: 12
<212> TYPE: PRT
<213> ORGANISM: Homo sapiens

<400> SEQUENCE: 19

Leu Val Gly Gly Gly Tyr Asp Leu Met Phe Asp Ser
```

<210> SEQ ID NO 20
<211> LENGTH: 13
<212> TYPE: PRT
<213> ORGANISM: Homo sapiens

<400> SEQUENCE: 20

Tyr Val Thr Tyr Gly Tyr Asp Asp Tyr His Phe Asp Tyr
1               5                   10

<210> SEQ ID NO 21
<211> LENGTH: 6
<212> TYPE: PRT
<213> ORGANISM: Homo sapiens

<400> SEQUENCE: 21

Ser Gly Tyr Leu Asp Tyr
1               5

<210> SEQ ID NO 22
<211> LENGTH: 18
<212> TYPE: PRT
<213> ORGANISM: Homo sapiens

<400> SEQUENCE: 22

Tyr Ile Gly Tyr Thr Asn Val Met Asp Ile Arg Pro Gly Tyr Phe Leu
1               5                   10                  15

Asp Tyr

<210> SEQ ID NO 23
<211> LENGTH: 12
<212> TYPE: PRT
<213> ORGANISM: Homo sapiens

<400> SEQUENCE: 23

Phe Arg Ala Tyr Gly Asp Asp Phe Tyr Phe Asp Val
1               5                   10

<210> SEQ ID NO 24
<211> LENGTH: 15
<212> TYPE: PRT
<213> ORGANISM: Homo sapiens
<220> FEATURE:
<221> NAME/KEY: VARIANT
<222> LOCATION: (1)...(15)
<223> OTHER INFORMATION: Xaa = Any Amino Acid

<400> SEQUENCE: 24

Xaa Met Trp Ser Asp Tyr Gly Gln Leu Val Lys Gly Gly Asp Ile
1               5                   10                  15

<210> SEQ ID NO 25
<211> LENGTH: 11
<212> TYPE: PRT
<213> ORGANISM: Homo sapiens

<400> SEQUENCE: 25

Tyr Tyr Val Thr Asp Thr Ala Tyr Phe Asp Tyr
1               5                   10

<210> SEQ ID NO 26
<211> LENGTH: 11
<212> TYPE: PRT
<213> ORGANISM: Homo sapiens

```
<400> SEQUENCE: 26

His Asp Phe Asp Gly Ser Ile Phe Met Asp Phe
 1               5                   10

<210> SEQ ID NO 27
<211> LENGTH: 12
<212> TYPE: PRT
<213> ORGANISM: Homo sapiens

<400> SEQUENCE: 27

Tyr Ala Gly His Gln Tyr Glu Phe Phe Asp Phe
 1               5                   10

<210> SEQ ID NO 28
<211> LENGTH: 11
<212> TYPE: PRT
<213> ORGANISM: Homo sapiens

<400> SEQUENCE: 28

Leu Tyr Ala Asp Ala Asp Ile Tyr Phe Asp Tyr
 1               5                   10

<210> SEQ ID NO 29
<211> LENGTH: 9
<212> TYPE: PRT
<213> ORGANISM: Homo sapiens

<400> SEQUENCE: 29

Thr Lys Tyr Val Gly Ser Glu Asp Val
 1               5

<210> SEQ ID NO 30
<211> LENGTH: 9
<212> TYPE: PRT
<213> ORGANISM: Homo sapiens

<400> SEQUENCE: 30

Tyr Arg Tyr Pro His Met Phe Asp Phe
 1               5

<210> SEQ ID NO 31
<211> LENGTH: 11
<212> TYPE: PRT
<213> ORGANISM: Homo sapiens

<400> SEQUENCE: 31

Leu Phe Ala Gly Leu Glu Leu Tyr Phe Asp Tyr
 1               5                   10

<210> SEQ ID NO 32
<211> LENGTH: 8
<212> TYPE: PRT
<213> ORGANISM: Homo sapiens

<400> SEQUENCE: 32

Gly Gly Phe Phe Asn Met Asp Tyr
 1               5

<210> SEQ ID NO 33
<211> LENGTH: 10
<212> TYPE: PRT
<213> ORGANISM: Homo sapiens

<400> SEQUENCE: 33
```

```
Gly Tyr Ile Pro Tyr His Leu Phe Asp Tyr
 1               5                  10

<210> SEQ ID NO 34
<211> LENGTH: 12
<212> TYPE: PRT
<213> ORGANISM: Homo sapiens

<400> SEQUENCE: 34

Tyr Tyr Gly Phe Glu Tyr Asp Leu Leu Phe Asp Asn
 1               5                  10

<210> SEQ ID NO 35
<211> LENGTH: 8
<212> TYPE: PRT
<213> ORGANISM: Homo sapiens

<400> SEQUENCE: 35

Ile Thr Tyr Ile Gly Tyr Asp Phe
 1               5

<210> SEQ ID NO 36
<211> LENGTH: 7
<212> TYPE: PRT
<213> ORGANISM: Homo sapiens

<400> SEQUENCE: 36

Gln Glu Trp Tyr Met Asp Tyr
 1               5

<210> SEQ ID NO 37
<211> LENGTH: 11
<212> TYPE: PRT
<213> ORGANISM: Homo sapiens

<400> SEQUENCE: 37

Leu Tyr Pro Glu Asp Leu Ile Tyr Phe Asp Tyr
 1               5                  10

<210> SEQ ID NO 38
<211> LENGTH: 15
<212> TYPE: PRT
<213> ORGANISM: Homo sapiens

<400> SEQUENCE: 38

Trp Met Thr Pro Pro Gly His Tyr Tyr Gly Tyr Thr Phe Asp Val
 1               5                  10                  15

<210> SEQ ID NO 39
<211> LENGTH: 12
<212> TYPE: PRT
<213> ORGANISM: Homo sapiens

<400> SEQUENCE: 39

Leu Arg Val His Asp Tyr Ala Met Tyr Phe Asp Leu
 1               5                  10

<210> SEQ ID NO 40
<211> LENGTH: 13
<212> TYPE: PRT
<213> ORGANISM: Homo sapiens

<400> SEQUENCE: 40

Phe Val Ser Tyr Asn Gly Ser Val Pro Tyr Phe Asp Tyr
```

<210> SEQ ID NO 41
<211> LENGTH: 11
<212> TYPE: PRT
<213> ORGANISM: Homo sapiens

<400> SEQUENCE: 41

Ile Ile Gly Asp Tyr Val Ile Phe Phe Asp Val
1               5                   10

<210> SEQ ID NO 42
<211> LENGTH: 11
<212> TYPE: PRT
<213> ORGANISM: Homo sapiens

<400> SEQUENCE: 42

Leu Phe Thr Tyr Pro Phe Leu Tyr Phe Asp Val
1               5                   10

<210> SEQ ID NO 43
<211> LENGTH: 11
<212> TYPE: PRT
<213> ORGANISM: Homo sapiens

<400> SEQUENCE: 43

Ile Leu Thr Gly His Val Leu Leu Phe Asp Tyr
1               5                   10

<210> SEQ ID NO 44
<211> LENGTH: 9
<212> TYPE: PRT
<213> ORGANISM: Homo sapiens

<400> SEQUENCE: 44

Gln Ser Tyr Asp Tyr Gln Gln Phe Thr
1               5

<210> SEQ ID NO 45
<211> LENGTH: 9
<212> TYPE: PRT
<213> ORGANISM: Homo sapiens

<400> SEQUENCE: 45

Gln Ser Tyr Asp Phe Lys Thr Tyr Leu
1               5

<210> SEQ ID NO 46
<211> LENGTH: 9
<212> TYPE: PRT
<213> ORGANISM: Homo sapiens

<400> SEQUENCE: 46

Gln Ser Tyr Asp Phe Leu Arg Phe Ser
1               5

<210> SEQ ID NO 47
<211> LENGTH: 9
<212> TYPE: PRT
<213> ORGANISM: Homo sapiens

<400> SEQUENCE: 47

Gln Ser Tyr Asp Phe Ile Asn Val Ile
1               5

-continued

```
<210> SEQ ID NO 48
<211> LENGTH: 9
<212> TYPE: PRT
<213> ORGANISM: Homo sapiens

<400> SEQUENCE: 48

Gln Ser Tyr Asp Phe Val Arg Phe Met
 1               5

<210> SEQ ID NO 49
<211> LENGTH: 9
<212> TYPE: PRT
<213> ORGANISM: Homo sapiens

<400> SEQUENCE: 49

Gln Ser Tyr Asp Phe Tyr Lys Phe Asn
 1               5

<210> SEQ ID NO 50
<211> LENGTH: 9
<212> TYPE: PRT
<213> ORGANISM: Homo sapiens

<400> SEQUENCE: 50

Gln Ser Tyr Asp Phe Arg Arg Phe Ser
 1               5

<210> SEQ ID NO 51
<211> LENGTH: 9
<212> TYPE: PRT
<213> ORGANISM: Homo sapiens

<400> SEQUENCE: 51

Gln Ser Arg Asp Phe Asn Arg Gly Pro
 1               5

<210> SEQ ID NO 52
<211> LENGTH: 8
<212> TYPE: PRT
<213> ORGANISM: Homo sapiens

<400> SEQUENCE: 52

Gln Ser Tyr Asp Gln Arg Lys Trp
 1               5

<210> SEQ ID NO 53
<211> LENGTH: 8
<212> TYPE: PRT
<213> ORGANISM: Homo sapiens

<400> SEQUENCE: 53

Gln Gln Leu Tyr Gly Thr Val Ser
 1               5

<210> SEQ ID NO 54
<211> LENGTH: 9
<212> TYPE: PRT
<213> ORGANISM: Homo sapiens

<400> SEQUENCE: 54

Gln Ser Tyr Asp Gly Phe Lys Thr His
 1               5

<210> SEQ ID NO 55
```

```
<211> LENGTH: 8
<212> TYPE: PRT
<213> ORGANISM: Homo sapiens

<400> SEQUENCE: 55

Gln Ser Tyr Asp Tyr Ser Leu Leu
 1               5

<210> SEQ ID NO 56
<211> LENGTH: 8
<212> TYPE: PRT
<213> ORGANISM: Homo sapiens

<400> SEQUENCE: 56

Gln Ser Tyr Asp Phe Asn Phe His
 1               5

<210> SEQ ID NO 57
<211> LENGTH: 10
<212> TYPE: PRT
<213> ORGANISM: Homo sapiens

<400> SEQUENCE: 57

Gln Ser Tyr Asp Met Ile Ala Arg Tyr Pro
 1               5                  10

<210> SEQ ID NO 58
<211> LENGTH: 10
<212> TYPE: PRT
<213> ORGANISM: Homo sapiens

<400> SEQUENCE: 58

Gln Ser Trp Asp Ile His Pro Phe Asp Val
 1               5                  10

<210> SEQ ID NO 59
<211> LENGTH: 8
<212> TYPE: PRT
<213> ORGANISM: Homo sapiens

<400> SEQUENCE: 59

Gln Ser Trp Asp Leu Glu Pro Tyr
 1               5

<210> SEQ ID NO 60
<211> LENGTH: 9
<212> TYPE: PRT
<213> ORGANISM: Homo sapiens

<400> SEQUENCE: 60

Gln Ser Tyr Asp Val Leu Asp Ser Glu
 1               5

<210> SEQ ID NO 61
<211> LENGTH: 10
<212> TYPE: PRT
<213> ORGANISM: Homo sapiens

<400> SEQUENCE: 61

Gln Ser Tyr Asp Pro Ser His Pro Ser Lys
 1               5                  10

<210> SEQ ID NO 62
<211> LENGTH: 8
<212> TYPE: PRT
```

-continued

<213> ORGANISM: Homo sapiens

<400> SEQUENCE: 62

Gln Ser Tyr Asp Asp Met Gln Phe
1               5

<210> SEQ ID NO 63
<211> LENGTH: 9
<212> TYPE: PRT
<213> ORGANISM: Homo sapiens

<400> SEQUENCE: 63

Gln Ser Trp Asp Ile Asn His Ala Ile
1               5

<210> SEQ ID NO 64
<211> LENGTH: 9
<212> TYPE: PRT
<213> ORGANISM: Homo sapiens

<400> SEQUENCE: 64

Gln Ser Tyr Asp Tyr Tyr Asp Tyr Gly
1               5

<210> SEQ ID NO 65
<211> LENGTH: 8
<212> TYPE: PRT
<213> ORGANISM: Homo sapiens

<400> SEQUENCE: 65

Gln Gln Ala Asn Asp Phe Pro Ile
1               5

<210> SEQ ID NO 66
<211> LENGTH: 10
<212> TYPE: PRT
<213> ORGANISM: Homo sapiens

<400> SEQUENCE: 66

Gln Ser Trp Asp Asn Leu Lys Met Pro Val
1               5                   10

<210> SEQ ID NO 67
<211> LENGTH: 10
<212> TYPE: PRT
<213> ORGANISM: Homo sapiens

<400> SEQUENCE: 67

Gln Ser Tyr Asp Val Phe Pro Ile Asn Arg
1               5                   10

<210> SEQ ID NO 68
<211> LENGTH: 7
<212> TYPE: PRT
<213> ORGANISM: Homo sapiens

<400> SEQUENCE: 68

Gln Ser Asp Leu Tyr Phe Pro
1               5

<210> SEQ ID NO 69
<211> LENGTH: 8
<212> TYPE: PRT
<213> ORGANISM: Homo sapiens

```
<400> SEQUENCE: 69

Gln Ser Tyr Asp Val Thr Pro Arg
1               5

<210> SEQ ID NO 70
<211> LENGTH: 9
<212> TYPE: PRT
<213> ORGANISM: Homo sapiens

<400> SEQUENCE: 70

Gln Ser Tyr Asp Pro Val Gly Phe Pro
1               5

<210> SEQ ID NO 71
<211> LENGTH: 8
<212> TYPE: PRT
<213> ORGANISM: Homo sapiens

<400> SEQUENCE: 71

Gln Ser Tyr Asp Leu Ser Pro Arg
1               5

<210> SEQ ID NO 72
<211> LENGTH: 10
<212> TYPE: PRT
<213> ORGANISM: Homo sapiens

<400> SEQUENCE: 72

Gln Ser Tyr Asp Phe Ser His Tyr Phe Phe
1               5                   10

<210> SEQ ID NO 73
<211> LENGTH: 9
<212> TYPE: PRT
<213> ORGANISM: Homo sapiens

<400> SEQUENCE: 73

Gln Ser Tyr Asp Leu Arg Tyr Ser His
1               5

<210> SEQ ID NO 74
<211> LENGTH: 8
<212> TYPE: PRT
<213> ORGANISM: Homo sapiens

<400> SEQUENCE: 74

Gln Ser Tyr Asp Leu Arg Asn Arg
1               5

<210> SEQ ID NO 75
<211> LENGTH: 9
<212> TYPE: PRT
<213> ORGANISM: Homo sapiens

<400> SEQUENCE: 75

Gln Ser Tyr Asp Phe Thr Tyr Gly Ser
1               5

<210> SEQ ID NO 76
<211> LENGTH: 8
<212> TYPE: PRT
<213> ORGANISM: Homo sapiens

<400> SEQUENCE: 76
```

Gln Gln Phe Asn Asp Ser Pro Tyr
1               5

<210> SEQ ID NO 77
<211> LENGTH: 9
<212> TYPE: PRT
<213> ORGANISM: Homo sapiens

<400> SEQUENCE: 77

Gln Ser Tyr Asp Ile Ser Gly Tyr Pro
1               5

<210> SEQ ID NO 78
<211> LENGTH: 10
<212> TYPE: PRT
<213> ORGANISM: Homo sapiens

<400> SEQUENCE: 78

Gln Ser Arg Asp Leu Tyr Tyr Val Tyr Tyr
1               5                   10

<210> SEQ ID NO 79
<211> LENGTH: 8
<212> TYPE: PRT
<213> ORGANISM: Homo sapiens

<400> SEQUENCE: 79

Gln Ser Tyr Asp Arg Ser Met Trp
1               5

<210> SEQ ID NO 80
<211> LENGTH: 9
<212> TYPE: PRT
<213> ORGANISM: Homo sapiens

<400> SEQUENCE: 80

Gln Ser Trp Asp Val Gln Thr Asp Lys
1               5

<210> SEQ ID NO 81
<211> LENGTH: 9
<212> TYPE: PRT
<213> ORGANISM: Homo sapiens

<400> SEQUENCE: 81

Gln Ser Trp Asp Pro Ser His Tyr Tyr
1               5

<210> SEQ ID NO 82
<211> LENGTH: 9
<212> TYPE: PRT
<213> ORGANISM: Homo sapiens

<400> SEQUENCE: 82

Gln Ser Tyr Asp Ile Met Pro Glu Arg
1               5

<210> SEQ ID NO 83
<211> LENGTH: 9
<212> TYPE: PRT
<213> ORGANISM: Homo sapiens

<400> SEQUENCE: 83

Gln Ser Met Asp Phe Arg Leu Met His
1               5

```
<210> SEQ ID NO 84
<211> LENGTH: 9
<212> TYPE: PRT
<213> ORGANISM: Homo sapiens

<400> SEQUENCE: 84

Gln Ser Phe Asp Met Ile His Pro Tyr
 1               5

<210> SEQ ID NO 85
<211> LENGTH: 7
<212> TYPE: PRT
<213> ORGANISM: Homo sapiens

<400> SEQUENCE: 85

Gln Ser Asp Phe Pro Val Met
 1               5

<210> SEQ ID NO 86
<211> LENGTH: 7
<212> TYPE: PRT
<213> ORGANISM: Homo sapiens

<400> SEQUENCE: 86

Gln Ser Asp Asn Pro Tyr Leu
 1               5

<210> SEQ ID NO 87
<211> LENGTH: 11
<212> TYPE: PRT
<213> ORGANISM: Homo sapiens

<400> SEQUENCE: 87

Thr Cys Val Pro Pro His Pro Gln Thr Ala Phe
 1               5                  10

<210> SEQ ID NO 88
<211> LENGTH: 12
<212> TYPE: PRT
<213> ORGANISM: Homo sapiens

<400> SEQUENCE: 88

Cys Thr Ser Val Pro Pro His Pro Gln Thr Ala Phe
 1               5                  10

<210> SEQ ID NO 89
<211> LENGTH: 12
<212> TYPE: PRT
<213> ORGANISM: Homo sapiens

<400> SEQUENCE: 89

Ser Thr Cys Val Pro Pro His Pro Gln Thr Ala Phe
 1               5                  10

<210> SEQ ID NO 90
<211> LENGTH: 13
<212> TYPE: PRT
<213> ORGANISM: Homo sapiens

<400> SEQUENCE: 90

Ser Thr Ser Val Pro Pro His Pro Gln Thr Ala Phe Cys
 1               5                  10
```

<210> SEQ ID NO 91
<211> LENGTH: 10
<212> TYPE: PRT
<213> ORGANISM: Homo sapiens

<400> SEQUENCE: 91

Cys Glu Val Asn Gln Thr Thr Leu Tyr Gln
1               5                   10

<210> SEQ ID NO 92
<211> LENGTH: 12
<212> TYPE: PRT
<213> ORGANISM: Homo sapiens

<400> SEQUENCE: 92

Pro Ala Met Glu Ser Val Cys Gly Tyr Phe His Arg
1               5                   10

<210> SEQ ID NO 93
<211> LENGTH: 16
<212> TYPE: PRT
<213> ORGANISM: Homo sapiens

<400> SEQUENCE: 93

Pro Ala Met Glu Ser Val Cys Gly Tyr Phe His Arg Ser His Asn Arg
1               5                   10                  15

<210> SEQ ID NO 94
<211> LENGTH: 17
<212> TYPE: PRT
<213> ORGANISM: Homo sapiens

<400> SEQUENCE: 94

Cys Pro Ala Met Glu Ser Val Ser Gly Tyr Phe His Arg Ser His Asn
1               5                   10                  15

Arg

<210> SEQ ID NO 95
<211> LENGTH: 17
<212> TYPE: PRT
<213> ORGANISM: Homo sapiens

<400> SEQUENCE: 95

Pro Ala Met Glu Ser Val Ser Gly Tyr Phe His Arg Ser His Asn Arg
1               5                   10                  15

Cys

<210> SEQ ID NO 96
<211> LENGTH: 12
<212> TYPE: PRT
<213> ORGANISM: Homo sapiens

<400> SEQUENCE: 96

Cys Leu Trp Thr Asp Gln Leu Leu Gln Gly Ser Glu
1               5                   10

<210> SEQ ID NO 97
<211> LENGTH: 215
<212> TYPE: PRT
<213> ORGANISM: Homo sapiens

<400> SEQUENCE: 97

Asp Ile Ala Leu Thr Gln Pro Ala Ser Val Ser Gly Ser Pro Gly Gln
1               5                   10                  15

```
Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Tyr Gln
                85                  90                  95

Gln Phe Thr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala
    210                 215

<210> SEQ ID NO 98
<211> LENGTH: 215
<212> TYPE: PRT
<213> ORGANISM: Homo sapiens

<400> SEQUENCE: 98

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Phe Lys
                85                  90                  95

Thr Tyr Leu Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
```

```
                        165                 170                 175
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Ala
    210                 215

<210> SEQ ID NO 99
<211> LENGTH: 211
<212> TYPE: PRT
<213> ORGANISM: Homo sapiens

<400> SEQUENCE: 99

Asp Ile Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Tyr Asp Phe Leu
                 85                  90                  95

Arg Phe Ser Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala
    210

<210> SEQ ID NO 100
<211> LENGTH: 215
<212> TYPE: PRT
<213> ORGANISM: Homo sapiens

<400> SEQUENCE: 100

Asp Ile Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
```

```
            50                  55                  60
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Tyr Asp Phe Ile
                 85                  90                  95

Asn Val Ile Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala
    210                 215

<210> SEQ ID NO 101
<211> LENGTH: 215
<212> TYPE: PRT
<213> ORGANISM: Homo sapiens

<400> SEQUENCE: 101

Asp Ile Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Tyr Asp Phe Val
                 85                  90                  95

Arg Phe Met Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205
```

-continued

Thr Val Ala Pro Thr Glu Ala
    210             215

<210> SEQ ID NO 102
<211> LENGTH: 215
<212> TYPE: PRT
<213> ORGANISM: Homo sapiens

<400> SEQUENCE: 102

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Phe Tyr
                85                  90                  95

Lys Phe Asn Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala
    210             215

<210> SEQ ID NO 103
<211> LENGTH: 215
<212> TYPE: PRT
<213> ORGANISM: Homo sapiens

<400> SEQUENCE: 103

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Phe Arg
                85                  90                  95

```
Arg Phe Ser Val Phe Gly Gly Thr Lys Leu Thr Val Leu Gly Gln
            100                 105                 110
Pro Lys Ala Ala Pro Ser Val Thr Leu Phe Pro Pro Ser Ser Glu Glu
            115                 120                 125
Leu Gln Ala Asn Lys Ala Thr Leu Val Cys Leu Ile Ser Asp Phe Tyr
        130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Ala
    210                 215

<210> SEQ ID NO 104
<211> LENGTH: 214
<212> TYPE: PRT
<213> ORGANISM: Homo sapiens

<400> SEQUENCE: 104

Asp Ile Val Leu Thr Gln Pro Pro Ser Val Ser Gly Ala Pro Gly Gln
1               5                   10                  15
Arg Val Thr Ile Ser Cys Ser Gly Ser Ser Ser Asn Ile Gly Ser Asn
            20                  25                  30
Tyr Val Ser Trp Tyr Gln Gln Leu Pro Gly Thr Ala Pro Lys Leu Leu
        35                  40                  45
Ile Tyr Asp Asn Asn Gln Arg Pro Ser Gly Val Pro Asp Arg Phe Ser
    50                  55                  60
Gly Ser Lys Ser Gly Thr Ser Ala Ser Leu Ala Ile Thr Gly Leu Gln
65                  70                  75                  80
Ser Glu Asp Glu Ala Asp Tyr Tyr Cys Gln Ser Arg Asp Phe Asn Arg
                85                  90                  95
Gly Pro Val Phe Gly Gly Gly Thr Lys Leu Thr Val Leu Gly Gln Pro
            100                 105                 110
Lys Ala Ala Pro Ser Val Thr Leu Phe Pro Pro Ser Ser Glu Glu Leu
        115                 120                 125
Gln Ala Asn Lys Ala Thr Leu Val Cys Leu Ile Ser Asp Phe Tyr Pro
    130                 135                 140
Gly Ala Val Thr Val Ala Trp Lys Ala Asp Ser Ser Pro Val Lys Ala
145                 150                 155                 160
Gly Val Glu Thr Thr Thr Pro Ser Lys Gln Ser Asn Asn Lys Tyr Ala
                165                 170                 175
Ala Ser Ser Tyr Leu Ser Leu Thr Pro Glu Gln Trp Lys Ser His Arg
            180                 185                 190
Ser Tyr Ser Cys Gln Val Thr His Glu Gly Ser Thr Val Glu Lys Thr
        195                 200                 205
Val Ala Pro Thr Glu Ala
    210

<210> SEQ ID NO 105
<211> LENGTH: 213
<212> TYPE: PRT
<213> ORGANISM: Homo sapiens
```

<400> SEQUENCE: 105

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Gln Arg Lys
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
    210

<210> SEQ ID NO 106
<211> LENGTH: 215
<212> TYPE: PRT
<213> ORGANISM: Homo sapiens

<400> SEQUENCE: 106

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Leu Tyr Gly Thr Ser
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Ala
    210                 215

<210> SEQ ID NO 107
<211> LENGTH: 214
<212> TYPE: PRT
<213> ORGANISM: Homo sapiens

<400> SEQUENCE: 107

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Gly Phe Lys
                85                  90                  95

Thr His Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Ala
    210

<210> SEQ ID NO 108
<211> LENGTH: 211
<212> TYPE: PRT
<213> ORGANISM: Homo sapiens

<400> SEQUENCE: 108

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
            20                  25                  30
```

-continued

Ser Trp Tyr Gln Gln Lys Pro Gly Gln Ala Pro Val Leu Val Ile Tyr
                35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Asp Tyr Ser Leu Leu Val
                 85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Ala
    210

<210> SEQ ID NO 109
<211> LENGTH: 211
<212> TYPE: PRT
<213> ORGANISM: Homo sapiens

<400> SEQUENCE: 109

Asp Ile Glu Leu Thr Gln Pro Pro Ser Val Ser Val Ala Pro Gly Gln
 1               5                  10                  15

Thr Ala Arg Ile Ser Cys Ser Gly Asp Ala Leu Gly Asp Lys Tyr Ala
                 20                  25                  30

Ser Trp Tyr Gln Gln Lys Pro Gly Gln Ala Pro Val Leu Val Ile Tyr
                35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Asp Phe Asn Phe His Val
                 85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser

```
                  180                 185                 190
Cys Gln Val Thr His Glu Gly Ser Thr Val Glu Lys Thr Val Ala Pro
            195                 200                 205
Thr Glu Ala
    210

<210> SEQ ID NO 110
<211> LENGTH: 216
<212> TYPE: PRT
<213> ORGANISM: Homo sapiens

<400> SEQUENCE: 110

Asp Ile Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Tyr Asp Met Ile
                 85                  90                  95

Ala Arg Tyr Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Ala
    210                 215

<210> SEQ ID NO 111
<211> LENGTH: 213
<212> TYPE: PRT
<213> ORGANISM: Homo sapiens

<400> SEQUENCE: 111

Asp Ile Glu Leu Thr Gln Pro Pro Ser Val Ser Val Ala Pro Gly Gln
  1               5                  10                  15

Thr Ala Arg Ile Ser Cys Ser Gly Asp Ala Leu Gly Asp Lys Tyr Ala
             20                  25                  30

Ser Trp Tyr Gln Gln Lys Pro Gly Gln Ala Pro Val Leu Val Ile Tyr
         35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
```

```
                65                  70                  75                  80
Asp Glu Ala Asp Tyr Tyr Cys Gln Ser Trp Asp Ile His Pro Phe Asp
                    85                  90                  95

Val Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
                115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
            195                 200                 205

Ala Pro Thr Glu Ala
            210

<210> SEQ ID NO 112
<211> LENGTH: 213
<212> TYPE: PRT
<213> ORGANISM: Homo sapiens

<400> SEQUENCE: 112

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
                20                  25                  30

Tyr Val Ser Trp Tyr Gln Gln Leu Pro Gly Thr Ala Pro Lys Leu Leu
            35                  40                  45

Ile Tyr Asp Asn Asn Gln Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Trp Asp Leu Glu Pro
                    85                  90                  95

Tyr Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
                115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
            195                 200                 205

Ala Pro Thr Glu Ala
            210
```

<210> SEQ ID NO 113
<211> LENGTH: 215
<212> TYPE: PRT
<213> ORGANISM: Homo sapiens

<400> SEQUENCE: 113

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Val Leu
                85                  90                  95

Asp Ser Glu Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala
    210                 215

<210> SEQ ID NO 114
<211> LENGTH: 216
<212> TYPE: PRT
<213> ORGANISM: Homo sapiens

<400> SEQUENCE: 114

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Pro Ser
                85                  90                  95

His Pro Ser Lys Val Phe Gly Gly Gly Thr Lys Leu Thr Val Leu Gly
            100                 105                 110

```
Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Ala
    210                 215

<210> SEQ ID NO 115
<211> LENGTH: 214
<212> TYPE: PRT
<213> ORGANISM: Homo sapiens

<400> SEQUENCE: 115

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Asp Met
                85                  90                  95

Gln Phe Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
                195                 200                 205

Val Ala Pro Thr Glu Ala
    210

<210> SEQ ID NO 116
<211> LENGTH: 215
<212> TYPE: PRT
<213> ORGANISM: Homo sapiens

<400> SEQUENCE: 116
```

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Gln Ser Trp Asp Ile Asn
                85                  90                  95

His Ala Ile Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala
    210                 215

<210> SEQ ID NO 117
<211> LENGTH: 215
<212> TYPE: PRT
<213> ORGANISM: Homo sapiens

<400> SEQUENCE: 117

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Gln Ser Tyr Asp Tyr Tyr
                85                  90                  95

Asp Tyr Gly Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
        180                 185                 190

Arg Ser Tyr Ser Cys Gln Val Thr His Glu Gly Ser Thr Val Glu Lys
    195                 200                 205

Thr Val Ala Pro Thr Glu Ala
    210                 215

<210> SEQ ID NO 118
<211> LENGTH: 215
<212> TYPE: PRT
<213> ORGANISM: Homo sapiens

<400> SEQUENCE: 118

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Ala Asn Asp Phe Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Ala
    210                 215

<210> SEQ ID NO 119
<211> LENGTH: 216
<212> TYPE: PRT
<213> ORGANISM: Homo sapiens

<400> SEQUENCE: 119

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45
```

```
Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Trp Asp Asn Leu
                85                  90                  95

Lys Met Pro Val Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Ala
    210                 215

<210> SEQ ID NO 120
<211> LENGTH: 216
<212> TYPE: PRT
<213> ORGANISM: Homo sapiens

<400> SEQUENCE: 120

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Val Phe
                85                  90                  95

Pro Ile Asn Arg Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
```

```
                    195                 200                 205
Lys Thr Val Ala Pro Thr Glu Ala
    210                 215

<210> SEQ ID NO 121
<211> LENGTH: 213
<212> TYPE: PRT
<213> ORGANISM: Homo sapiens

<400> SEQUENCE: 121

Asp Ile Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Asp Leu Tyr Phe
                 85                  90                  95

Pro Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
    210

<210> SEQ ID NO 122
<211> LENGTH: 214
<212> TYPE: PRT
<213> ORGANISM: Homo sapiens

<400> SEQUENCE: 122

Asp Ile Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Val Thr
```

```
                     85                  90                  95
Pro Arg Val Phe Gly Gly Thr Lys Leu Thr Val Leu Gly Gln Pro
                100                 105                 110
Lys Ala Ala Pro Ser Val Thr Leu Phe Pro Pro Ser Ser Glu Glu Leu
                115                 120                 125
Gln Ala Asn Lys Ala Thr Leu Val Cys Leu Ile Ser Asp Phe Tyr Pro
            130                 135                 140
Gly Ala Val Thr Val Ala Trp Lys Ala Asp Ser Ser Pro Val Lys Ala
145                 150                 155                 160
Gly Val Glu Thr Thr Thr Pro Ser Lys Gln Ser Asn Asn Lys Tyr Ala
                165                 170                 175
Ala Ser Ser Tyr Leu Ser Leu Thr Pro Glu Gln Trp Lys Ser His Arg
            180                 185                 190
Ser Tyr Ser Cys Gln Val Thr His Glu Gly Ser Thr Val Glu Lys Thr
        195                 200                 205
Val Ala Pro Thr Glu Ala
    210
```

<210> SEQ ID NO 123
<211> LENGTH: 212
<212> TYPE: PRT
<213> ORGANISM: Homo sapiens

<400> SEQUENCE: 123

```
Asp Ile Glu Leu Thr Gln Pro Pro Ser Val Ser Val Ala Pro Gly Gln
1               5                   10                  15
Thr Ala Arg Ile Ser Cys Ser Gly Asp Ala Leu Gly Asp Lys Tyr Ala
                20                  25                  30
Ser Trp Tyr Gln Gln Lys Pro Gly Gln Ala Pro Val Leu Val Ile Tyr
            35                  40                  45
Asp Asp Ser Asp Arg Pro Ser Gly Ile Pro Glu Arg Phe Ser Gly Ser
        50                  55                  60
Asn Ser Gly Asn Thr Ala Thr Leu Thr Ile Ser Gly Thr Gln Ala Glu
65                  70                  75                  80
Asp Glu Ala Asp Tyr Tyr Cys Gln Ser Arg Asp Pro Val Gly Phe Pro
                85                  90                  95
Val Phe Gly Gly Gly Thr Lys Leu Thr Val Leu Gly Gln Pro Lys Ala
                100                 105                 110
Ala Pro Ser Val Thr Leu Phe Pro Pro Ser Ser Glu Glu Leu Gln Ala
            115                 120                 125
Asn Lys Ala Thr Leu Val Cys Leu Ile Ser Asp Phe Tyr Pro Gly Ala
        130                 135                 140
Val Thr Val Ala Trp Lys Ala Asp Ser Ser Pro Val Lys Ala Gly Val
145                 150                 155                 160
Glu Thr Thr Thr Pro Ser Lys Gln Ser Asn Asn Lys Tyr Ala Ala Ser
                165                 170                 175
Ser Tyr Leu Ser Leu Thr Pro Glu Gln Trp Lys Ser His Arg Ser Tyr
            180                 185                 190
Ser Cys Gln Val Thr His Glu Gly Ser Thr Val Glu Lys Thr Val Ala
        195                 200                 205
Pro Thr Glu Ala
    210
```

<210> SEQ ID NO 124
<211> LENGTH: 214

<212> TYPE: PRT
<213> ORGANISM: Homo sapiens

<400> SEQUENCE: 124

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Leu Ser
                85                  90                  95

Pro Arg Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Ala
    210

<210> SEQ ID NO 125
<211> LENGTH: 216
<212> TYPE: PRT
<213> ORGANISM: Homo sapiens

<400> SEQUENCE: 125

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Phe Ser
                85                  90                  95

His Tyr Phe Phe Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

```
Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Ala
    210                 215

<210> SEQ ID NO 126
<211> LENGTH: 212
<212> TYPE: PRT
<213> ORGANISM: Homo sapiens

<400> SEQUENCE: 126

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
                20                  25                  30

Ser Trp Tyr Gln Gln Lys Pro Gly Gln Ala Pro Val Leu Val Ile Tyr
            35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Leu Arg Tyr Ser His
                85                  90                  95

Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Ala
    210

<210> SEQ ID NO 127
<211> LENGTH: 214
<212> TYPE: PRT
<213> ORGANISM: Homo sapiens

<400> SEQUENCE: 127

Asp Ile Ala Leu Thr Gln Pro Ala Ser Val Ser Gly Ser Pro Gly Gln
1               5                   10                  15
```

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Leu Arg
                85                  90                  95

Asn Arg Val Phe Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Ala
            210

<210> SEQ ID NO 128
<211> LENGTH: 215
<212> TYPE: PRT
<213> ORGANISM: Homo sapiens

<400> SEQUENCE: 128

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Phe Thr
                85                  90                  95

Tyr Gly Ser Val Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

```
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Ala
    210                 215

<210> SEQ ID NO 129
<211> LENGTH: 215
<212> TYPE: PRT
<213> ORGANISM: Homo sapiens

<400> SEQUENCE: 129

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Asn Asp Ser Pro
                85                  90                  95

Tyr Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Ala
    210                 215

<210> SEQ ID NO 130
<211> LENGTH: 215
<212> TYPE: PRT
<213> ORGANISM: Homo sapiens

<400> SEQUENCE: 130

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Tyr Asp Ile Ser
                 85                  90                  95

Gly Tyr Pro Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala
    210                 215

<210> SEQ ID NO 131
<211> LENGTH: 216
<212> TYPE: PRT
<213> ORGANISM: Homo sapiens

<400> SEQUENCE: 131

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Arg Asp Leu Tyr
                 85                  90                  95

Tyr Val Tyr Tyr Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Ala
```

<210> SEQ ID NO 132
<211> LENGTH: 211
<212> TYPE: PRT
<213> ORGANISM: Homo sapiens

<400> SEQUENCE: 132

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
            20                  25                  30

Ser Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Arg Ser Met Trp Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Ala
    210

<210> SEQ ID NO 133
<211> LENGTH: 215
<212> TYPE: PRT
<213> ORGANISM: Homo sapiens

<400> SEQUENCE: 133

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Trp Asp Val Gln
                85                  90                  95

Thr Asp Lys Val Phe Gly Gly Gly Thr Lys Leu Thr Val Leu Gly Gln

-continued

```
                100                 105                 110
Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala
    210                 215

<210> SEQ ID NO 134
<211> LENGTH: 212
<212> TYPE: PRT
<213> ORGANISM: Homo sapiens

<400> SEQUENCE: 134

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
                20                  25                  30

Ser Trp Tyr Gln Gln Lys Pro Gly Gln Ala Pro Val Leu Val Ile Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Pro Ser His Tyr Tyr
                85                  90                  95

Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Ala
    210

<210> SEQ ID NO 135
<211> LENGTH: 215
<212> TYPE: PRT
<213> ORGANISM: Homo sapiens
```

<400> SEQUENCE: 135

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Gln Ser Tyr Asp Ile Met
                85                  90                  95

Pro Glu Arg Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala
    210                 215

<210> SEQ ID NO 136
<211> LENGTH: 215
<212> TYPE: PRT
<213> ORGANISM: Homo sapiens

<400> SEQUENCE: 136

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Gln Ser Met Asp Phe Arg
                85                  90                  95

Leu Met His Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

```
Pro Gly Ala Val Thr Val Ala Trp Lys Ala Asp Ser Ser Pro Val Lys
145                 150                 155                 160

Ala Gly Val Glu Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Ala
    210                 215

<210> SEQ ID NO 137
<211> LENGTH: 215
<212> TYPE: PRT
<213> ORGANISM: Homo sapiens

<400> SEQUENCE: 137

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Phe Asp Met Ile
                85                  90                  95

His Pro Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Ala
    210                 215

<210> SEQ ID NO 138
<211> LENGTH: 213
<212> TYPE: PRT
<213> ORGANISM: Homo sapiens

<400> SEQUENCE: 138

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30
```

```
Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Asp Phe Pro Val
                 85                  90                  95

Met Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
    210

<210> SEQ ID NO 139
<211> LENGTH: 213
<212> TYPE: PRT
<213> ORGANISM: Homo sapiens

<400> SEQUENCE: 139

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Asp Asn Pro Tyr
                 85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190
```

```
Tyr Ser Cys Gln Val Thr His Glu Gly Ser Thr Val Glu Lys Thr Val
            195                 200                 205

Ala Pro Thr Glu Ala
        210

<210> SEQ ID NO 140
<211> LENGTH: 217
<212> TYPE: PRT
<213> ORGANISM: Homo sapiens

<400> SEQUENCE: 140

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Met Asp Ile Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Glu Phe
    210                 215

<210> SEQ ID NO 141
<211> LENGTH: 217
<212> TYPE: PRT
<213> ORGANISM: Homo sapiens

<400> SEQUENCE: 141

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Gly Phe Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Glu Phe
    210                 215

<210> SEQ ID NO 142
<211> LENGTH: 217
<212> TYPE: PRT
<213> ORGANISM: Homo sapiens

<400> SEQUENCE: 142

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Leu Asp Ile Trp Gly Gln Gly Thr Leu Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Glu Phe
    210                 215
```

```
<210> SEQ ID NO 143
<211> LENGTH: 221
<212> TYPE: PRT
<213> ORGANISM: Homo sapiens

<400> SEQUENCE: 143

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Thr Phe Pro Ile Asp Ala Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Glu Phe
    210                 215                 220

<210> SEQ ID NO 144
<211> LENGTH: 218
<212> TYPE: PRT
<213> ORGANISM: Homo sapiens

<400> SEQUENCE: 144

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly His Val Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
```

-continued

```
                115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Glu Phe
    210                 215

<210> SEQ ID NO 145
<211> LENGTH: 222
<212> TYPE: PRT
<213> ORGANISM: Homo sapiens

<400> SEQUENCE: 145

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Arg Gly Leu Ser Phe Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Glu Phe
    210                 215                 220

<210> SEQ ID NO 146
<211> LENGTH: 217
<212> TYPE: PRT
<213> ORGANISM: Homo sapiens

<400> SEQUENCE: 146

Gln Val Gln Leu Val Glu Ser Gly Gly Gly Leu Val Gln Pro Gly Gly
```

```
            1               5              10              15
Ser Leu Arg Leu Ser Cys Ala Ala Ser Gly Phe Thr Phe Ser Ser Tyr
                20              25              30

Ala Met Ser Trp Val Arg Gln Ala Pro Gly Lys Gly Leu Glu Trp Val
            35              40              45

Ser Ala Ile Ser Gly Ser Gly Gly Ser Thr Tyr Tyr Ala Asp Ser Val
         50              55              60

Lys Gly Arg Phe Thr Ile Ser Arg Asp Asn Ser Lys Asn Thr Leu Tyr
 65              70              75              80

Leu Gln Met Asn Ser Leu Arg Ala Glu Asp Thr Ala Val Tyr Tyr Cys
                85              90              95

Ala Arg Phe Phe Asp Tyr Trp Gly Gln Gly Thr Leu Val Thr Val Ser
            100             105             110

Ser Ala Ser Thr Lys Gly Pro Ser Val Phe Pro Leu Ala Pro Ser Ser
        115             120             125

Lys Ser Thr Ser Gly Gly Thr Ala Ala Leu Gly Cys Leu Val Lys Asp
    130             135             140

Tyr Phe Pro Glu Pro Val Thr Val Ser Trp Asn Ser Gly Ala Leu Thr
145             150             155             160

Ser Gly Val His Thr Phe Pro Ala Val Leu Gln Ser Ser Gly Leu Tyr
                165             170             175

Ser Leu Ser Ser Val Val Thr Val Pro Ser Ser Ser Leu Gly Thr Gln
            180             185             190

Thr Tyr Ile Cys Asn Val Asn His Lys Pro Ser Asn Thr Lys Val Asp
        195             200             205

Lys Lys Val Glu Pro Lys Ser Glu Phe
    210             215

<210> SEQ ID NO 147
<211> LENGTH: 225
<212> TYPE: PRT
<213> ORGANISM: Homo sapiens

<400> SEQUENCE: 147

Gln Val Gln Leu Val Gln Ser Gly Ala Glu Val Lys Lys Pro Gly Ser
 1               5              10              15

Ser Val Lys Val Ser Cys Lys Ala Ser Gly Gly Thr Phe Ser Ser Tyr
                20              25              30

Ala Ile Ser Trp Val Arg Gln Ala Pro Gly Gln Gly Leu Glu Trp Met
            35              40              45

Gly Gly Ile Ile Pro Ile Phe Gly Thr Ala Asn Tyr Ala Gln Lys Phe
         50              55              60

Gln Gly Arg Val Thr Ile Thr Ala Asp Glu Ser Thr Ser Thr Ala Tyr
 65              70              75              80

Met Glu Leu Ser Ser Leu Arg Ser Glu Asp Thr Ala Val Tyr Tyr Cys
                85              90              95

Ala Arg Gly Leu Tyr Trp Ala Val Tyr Pro Tyr Phe Asp Phe Trp Gly
            100             105             110

Gln Gly Thr Leu Val Thr Val Ser Ser Ala Ser Thr Lys Gly Pro Ser
        115             120             125

Val Phe Pro Leu Ala Pro Ser Ser Lys Ser Thr Ser Gly Gly Thr Ala
    130             135             140

Ala Leu Gly Cys Leu Val Lys Asp Tyr Phe Pro Glu Pro Val Thr Val
145             150             155             160
```

```
Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Glu
    210                 215                 220

Phe
225

<210> SEQ ID NO 148
<211> LENGTH: 224
<212> TYPE: PRT
<213> ORGANISM: Homo sapiens

<400> SEQUENCE: 148

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Asp Thr Tyr Tyr Pro Asp Leu Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Glu Phe
    210                 215                 220

<210> SEQ ID NO 149
<211> LENGTH: 220
<212> TYPE: PRT
<213> ORGANISM: Homo sapiens

<400> SEQUENCE: 149

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

```
Ala Ile Ser Trp Val Arg Gln Ala Pro Gly Gln Gly Leu Glu Trp Met
            35                  40                  45
Gly Gly Ile Ile Pro Ile Phe Gly Thr Ala Asn Tyr Ala Gln Lys Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Thr Tyr Tyr Tyr Phe Asp Ser Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Glu Phe
210                 215                 220

<210> SEQ ID NO 150
<211> LENGTH: 224
<212> TYPE: PRT
<213> ORGANISM: Homo sapiens

<400> SEQUENCE: 150

Gln Val Gln Leu Val Glu Ser Gly Gly Gly Leu Val Gln Pro Gly Gly
  1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Tyr Met Ala Tyr Met Ala Glu Ala Ile Asp Val Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Glu Phe
    210                 215                 220
```

<210> SEQ ID NO 151
<211> LENGTH: 230
<212> TYPE: PRT
<213> ORGANISM: Homo sapiens

<400> SEQUENCE: 151

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Val Gly Ile Val Gly Tyr Lys Pro Asp Glu Leu Leu Tyr
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Glu Phe
225                 230
```

<210> SEQ ID NO 152
<211> LENGTH: 222
<212> TYPE: PRT
<213> ORGANISM: Homo sapiens

<400> SEQUENCE: 152

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Gly Ala Tyr Phe Gly Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Glu Phe
    210                 215                 220

<210> SEQ ID NO 153
<211> LENGTH: 225
<212> TYPE: PRT
<213> ORGANISM: Homo sapiens

<400> SEQUENCE: 153

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
                 20                  25                  30

Ser Ala Ala Trp Asn Trp Ile Arg Gln Ser Pro Gly Arg Gly Leu Glu
             35                  40                  45

Trp Leu Gly Arg Thr Tyr Tyr Arg Ser Lys Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Gly Tyr Ala Asp Ile Ser Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
```

```
            210                 215                 220
Phe
225

<210> SEQ ID NO 154
<211> LENGTH: 220
<212> TYPE: PRT
<213> ORGANISM: Homo sapiens

<400> SEQUENCE: 154

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Leu Leu Leu Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Glu Phe
    210                 215                 220

<210> SEQ ID NO 155
<211> LENGTH: 229
<212> TYPE: PRT
<213> ORGANISM: Homo sapiens

<400> SEQUENCE: 155

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
                    85                  90                  95
Ala Arg Trp Ser Asp Gln Ser Tyr His Tyr Tyr Trp His Pro Tyr Phe
                100                 105                 110

Asp Val Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Glu Phe
225

<210> SEQ ID NO 156
<211> LENGTH: 220
<212> TYPE: PRT
<213> ORGANISM: Homo sapiens

<400> SEQUENCE: 156

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ile Gly Tyr Phe Asp Leu Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Glu Phe
    210                 215                 220
```

-continued

```
<210> SEQ ID NO 157
<211> LENGTH: 225
<212> TYPE: PRT
<213> ORGANISM: Homo sapiens

<400> SEQUENCE: 157

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Thr Asn Tyr Phe Asp Ser Ile Tyr Tyr Asp His Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe
225

<210> SEQ ID NO 158
<211> LENGTH: 225
<212> TYPE: PRT
<213> ORGANISM: Homo sapiens

<400> SEQUENCE: 158

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

```
Ala Arg Leu Val Gly Gly Tyr Asp Leu Met Phe Asp Ser Trp Gly
        100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Glu
        210                 215                 220

Phe
225

<210> SEQ ID NO 159
<211> LENGTH: 226
<212> TYPE: PRT
<213> ORGANISM: Homo sapiens

<400> SEQUENCE: 159

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Val Thr Tyr Gly Tyr Asp Asp Tyr His Phe Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
        210                 215                 220

Glu Phe
225
```

<210> SEQ ID NO 160
<211> LENGTH: 219
<212> TYPE: PRT
<213> ORGANISM: Homo sapiens

<400> SEQUENCE: 160

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Gly Tyr Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Glu Phe
    210                 215
```

<210> SEQ ID NO 161
<211> LENGTH: 231
<212> TYPE: PRT
<213> ORGANISM: Homo sapiens

<400> SEQUENCE: 161

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Ile Gly Tyr Thr Asn Val Met Asp Ile Arg Pro Gly Phe
            100                 105                 110
```

-continued

```
Tyr Leu Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Glu Phe
225                 230

<210> SEQ ID NO 162
<211> LENGTH: 225
<212> TYPE: PRT
<213> ORGANISM: Homo sapiens

<400> SEQUENCE: 162

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Phe Arg Ala Tyr Gly Asp Asp Phe Tyr Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe
225
```

-continued

```
<210> SEQ ID NO 163
<211> LENGTH: 228
<212> TYPE: PRT
<213> ORGANISM: Homo sapiens

<400> SEQUENCE: 163

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Met Trp Ser Asp Tyr Gly Gln Leu Val Lys Gly Gly Asp
            100                 105                 110

Ile Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Glu Phe
225

<210> SEQ ID NO 164
<211> LENGTH: 224
<212> TYPE: PRT
<213> ORGANISM: Homo sapiens

<400> SEQUENCE: 164

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Tyr Val Thr Asp Thr Ala Tyr Phe Asp Tyr Trp Gly Gln
```

-continued

```
               100                 105                 110
Gly Thr Leu Val Thr Val Ser Ser Ala Ser Thr Lys Gly Pro Ser Val
           115                 120                 125
Phe Pro Leu Ala Pro Ser Ser Lys Ser Thr Ser Gly Gly Thr Ala Ala
       130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
               165                 170                 175
Leu Gln Ser Ser Gly Leu Tyr Ser Leu Ser Val Val Thr Val Pro
           180                 185                 190
Ser Ser Ser Leu Gly Thr Gln Thr Tyr Ile Cys Asn Val Asn His Lys
       195                 200                 205
Pro Ser Asn Thr Lys Val Asp Lys Lys Val Glu Pro Lys Ser Glu Phe
   210                 215                 220
```

<210> SEQ ID NO 165
<211> LENGTH: 224
<212> TYPE: PRT
<213> ORGANISM: Homo sapiens

<400> SEQUENCE: 165

```
Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg His Asp Phe Asp Gly Ser Ile Phe Met Asp Phe Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Glu Phe
    210                 215                 220
```

<210> SEQ ID NO 166
<211> LENGTH: 225
<212> TYPE: PRT
<213> ORGANISM: Homo sapiens

<400> SEQUENCE: 166

```
Gln Val Gln Leu Val Gln Ser Gly Ala Glu Val Lys Lys Pro Gly Glu
  1               5                  10                  15
Ser Leu Lys Ile Ser Cys Lys Gly Ser Gly Tyr Ser Phe Thr Ser Tyr
             20                  25                  30
Trp Ile Gly Trp Val Arg Gln Met Pro Gly Lys Gly Leu Glu Trp Met
         35                  40                  45
Gly Ile Ile Tyr Pro Gly Asp Ser Asp Thr Arg Tyr Ser Pro Ser Phe
     50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Tyr Ala Gly His Gln Tyr Glu Phe Phe Asp Phe Trp Gly
             100                 105                 110
Gln Gly Thr Leu Val Thr Val Ser Ser Ala Ser Thr Lys Gly Pro Ser
         115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Glu
    210                 215                 220
Phe
225
```

<210> SEQ ID NO 167
<211> LENGTH: 224
<212> TYPE: PRT
<213> ORGANISM: Homo sapiens

<400> SEQUENCE: 167

```
Gln Val Gln Leu Val Gln Ser Gly Ala Glu Val Lys Lys Pro Gly Glu
  1               5                  10                  15
Ser Leu Lys Ile Ser Cys Lys Gly Ser Gly Tyr Ser Phe Thr Ser Tyr
             20                  25                  30
Trp Ile Gly Trp Val Arg Gln Met Pro Gly Lys Gly Leu Glu Trp Met
         35                  40                  45
Gly Ile Ile Tyr Pro Gly Asp Ser Asp Thr Arg Tyr Ser Pro Ser Phe
     50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Leu Tyr Ala Asp Ala Asp Ile Tyr Phe Asp Tyr Trp Gly Gln
             100                 105                 110
Gly Thr Leu Val Thr Val Ser Ser Ala Ser Thr Lys Gly Pro Ser Val
         115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Glu Phe
    210                 215                 220

<210> SEQ ID NO 168
<211> LENGTH: 222
<212> TYPE: PRT
<213> ORGANISM: Homo sapiens

<400> SEQUENCE: 168

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Val Gly Ser Glu Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Glu Phe
    210                 215                 220

<210> SEQ ID NO 169
<211> LENGTH: 222
<212> TYPE: PRT
<213> ORGANISM: Homo sapiens

<400> SEQUENCE: 169

Gln Val Gln Leu Val Gln Ser Gly Ala Glu Val Lys Lys Pro Gly Glu
1               5                   10                  15
```

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Arg Tyr Pro His Met Phe Asp Phe Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Glu Phe
    210                 215                 220

<210> SEQ ID NO 170
<211> LENGTH: 224
<212> TYPE: PRT
<213> ORGANISM: Homo sapiens

<400> SEQUENCE: 170

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Phe Ala Gly Leu Glu Leu Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

-continued

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Glu Phe
    210                 215                 220

<210> SEQ ID NO 171
<211> LENGTH: 221
<212> TYPE: PRT
<213> ORGANISM: Homo sapiens

<400> SEQUENCE: 171

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Phe Phe Asn Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Glu Phe
    210                 215                 220

<210> SEQ ID NO 172
<211> LENGTH: 223
<212> TYPE: PRT
<213> ORGANISM: Homo sapiens

<400> SEQUENCE: 172

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

-continued

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Ile Pro Tyr His Leu Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Glu Phe
    210                 215                 220

<210> SEQ ID NO 173
<211> LENGTH: 225
<212> TYPE: PRT
<213> ORGANISM: Homo sapiens

<400> SEQUENCE: 173

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Tyr Gly Phe Glu Tyr Asp Leu Leu Phe Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu

```
            210                 215                 220
Phe
225

<210> SEQ ID NO 174
<211> LENGTH: 221
<212> TYPE: PRT
<213> ORGANISM: Homo sapiens

<400> SEQUENCE: 174

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ile Thr Tyr Ile Gly Tyr Asp Phe Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Glu Phe
    210                 215                 220

<210> SEQ ID NO 175
<211> LENGTH: 220
<212> TYPE: PRT
<213> ORGANISM: Homo sapiens

<400> SEQUENCE: 175

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
```

-continued

```
                    85                  90                  95
Ala Arg Gln Glu Trp Tyr Met Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Glu Phe
210                 215                 220
```

<210> SEQ ID NO 176
<211> LENGTH: 224
<212> TYPE: PRT
<213> ORGANISM: Homo sapiens

<400> SEQUENCE: 176

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Tyr Pro Glu Asp Leu Ile Tyr Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Glu Phe
    210                 215                 220
```

<210> SEQ ID NO 177
<211> LENGTH: 231

```
<212> TYPE: PRT
<213> ORGANISM: Homo sapiens

<400> SEQUENCE: 177

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Gly Arg Gly Leu Glu
         35                  40                  45

Trp Leu Gly Arg Thr Tyr Tyr Arg Ser Lys Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
             85                  90                  95

Tyr Tyr Cys Ala Arg Trp Met Thr Pro Gly His Tyr Tyr Gly Tyr
            100                 105                 110

Thr Phe Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Glu Phe
225                 230

<210> SEQ ID NO 178
<211> LENGTH: 225
<212> TYPE: PRT
<213> ORGANISM: Homo sapiens

<400> SEQUENCE: 178

Gln Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
             85                  90                  95

Ala Arg Leu Arg Val His Asp Tyr Ala Met Tyr Phe Asp Leu Trp Gly
            100                 105                 110
```

```
Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe
225

<210> SEQ ID NO 179
<211> LENGTH: 226
<212> TYPE: PRT
<213> ORGANISM: Homo sapiens

<400> SEQUENCE: 179

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Phe Val Ser Tyr Asn Gly Ser Val Pro Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Glu Phe
225

<210> SEQ ID NO 180
```

```
<211> LENGTH: 224
<212> TYPE: PRT
<213> ORGANISM: Homo sapiens

<400> SEQUENCE: 180

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ile Ile Gly Asp Tyr Val Ile Phe Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Glu Phe
    210                 215                 220

<210> SEQ ID NO 181
<211> LENGTH: 224
<212> TYPE: PRT
<213> ORGANISM: Homo sapiens

<400> SEQUENCE: 181

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Phe Thr Tyr Pro Phe Leu Tyr Phe Asp Val Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Glu Phe
    210                 215                 220

<210> SEQ ID NO 182
<211> LENGTH: 224
<212> TYPE: PRT
<213> ORGANISM: Homo sapiens

<400> SEQUENCE: 182

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ile Leu Thr Gly His Val Leu Leu Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Glu Phe
    210                 215                 220

<210> SEQ ID NO 183
<211> LENGTH: 27
<212> TYPE: DNA
<213> ORGANISM: Homo sapiens

<400> SEQUENCE: 183
cagagctatg actatcagca gtttact                                      27
```

<210> SEQ ID NO 184
<211> LENGTH: 26
<212> TYPE: DNA
<213> ORGANISM: Homo sapiens

<400> SEQUENCE: 184
cagagctatg actttaagac ttatct                                    26

<210> SEQ ID NO 185
<211> LENGTH: 26
<212> TYPE: DNA
<213> ORGANISM: Homo sapiens

<400> SEQUENCE: 185
cagagctatg actttcttcg tttttc                                    26

<210> SEQ ID NO 186
<211> LENGTH: 27
<212> TYPE: DNA
<213> ORGANISM: Homo sapiens

<400> SEQUENCE: 186
cagagctatg actttattaa tgttatt                                   27

<210> SEQ ID NO 187
<211> LENGTH: 27
<212> TYPE: DNA
<213> ORGANISM: Homo sapiens

<400> SEQUENCE: 187
cagagctatg actttgttcg ttttatg                                   27

<210> SEQ ID NO 188
<211> LENGTH: 27
<212> TYPE: DNA
<213> ORGANISM: Homo sapiens

<400> SEQUENCE: 188
cagagctatg acttttataa gtttaat                                   27

<210> SEQ ID NO 189
<211> LENGTH: 27
<212> TYPE: DNA
<213> ORGANISM: Homo sapiens

<400> SEQUENCE: 189
cagagctatg actttcgtcg tttttct                                   27

<210> SEQ ID NO 190
<211> LENGTH: 27
<212> TYPE: DNA
<213> ORGANISM: Homo sapiens

<400> SEQUENCE: 190
cagagccgtg actttaatcg tggtcct                                   27

<210> SEQ ID NO 191
<211> LENGTH: 24
<212> TYPE: DNA
<213> ORGANISM: Homo sapiens

<400> SEQUENCE: 191
cagagctatg accagcgtaa gtgg                                      24

<210> SEQ ID NO 192
<211> LENGTH: 24
<212> TYPE: DNA
<213> ORGANISM: Homo sapiens

<400> SEQUENCE: 192
cagcagcttt atggtacttc tgtt                                      24

<210> SEQ ID NO 193
<211> LENGTH: 27
<212> TYPE: DNA
<213> ORGANISM: Homo sapiens

<400> SEQUENCE: 193
cagagctatg acggttttaa gactcat                                   27

<210> SEQ ID NO 194
<211> LENGTH: 24
<212> TYPE: DNA
<213> ORGANISM: Homo sapiens

<400> SEQUENCE: 194
cagagctatg actattctct tctt                                      24

<210> SEQ ID NO 195
<211> LENGTH: 24
<212> TYPE: DNA
<213> ORGANISM: Homo sapiens

<400> SEQUENCE: 195
cagagctatg actttaattt tcat                                      24

<210> SEQ ID NO 196
<211> LENGTH: 30
<212> TYPE: DNA
<213> ORGANISM: Homo sapiens

<400> SEQUENCE: 196
cagagctatg acatgattgc tcgttatcct                                30

<210> SEQ ID NO 197
<211> LENGTH: 30
<212> TYPE: DNA
<213> ORGANISM: Homo sapiens

<400> SEQUENCE: 197
cagagctggg acattcatcc ttttgatgtt                                30

<210> SEQ ID NO 198
<211> LENGTH: 24
<212> TYPE: DNA
<213> ORGANISM: Homo sapiens

<400> SEQUENCE: 198
cagagctggg accttgagcc ttat                                      24

<210> SEQ ID NO 199
<211> LENGTH: 27
<212> TYPE: DNA
<213> ORGANISM: Homo sapiens

<400> SEQUENCE: 199

|  |  |
|---|---|
| cagagctatg acgttcttga ttctgag | 27 |

<210> SEQ ID NO 200
<211> LENGTH: 30
<212> TYPE: DNA
<213> ORGANISM: Homo sapiens

<400> SEQUENCE: 200

|  |  |
|---|---|
| cagagctatg acccttctca tccttctaag | 30 |

<210> SEQ ID NO 201
<211> LENGTH: 24
<212> TYPE: DNA
<213> ORGANISM: Homo sapiens

<400> SEQUENCE: 201

|  |  |
|---|---|
| cagagctatg acgatatgca gttt | 24 |

<210> SEQ ID NO 202
<211> LENGTH: 27
<212> TYPE: DNA
<213> ORGANISM: Homo sapiens

<400> SEQUENCE: 202

|  |  |
|---|---|
| cagagctggg acattaatca tgctatt | 27 |

<210> SEQ ID NO 203
<211> LENGTH: 27
<212> TYPE: DNA
<213> ORGANISM: Homo sapiens

<400> SEQUENCE: 203

|  |  |
|---|---|
| cagagctatg actattatga ttatggt | 27 |

<210> SEQ ID NO 204
<211> LENGTH: 24
<212> TYPE: DNA
<213> ORGANISM: Homo sapiens

<400> SEQUENCE: 204

|  |  |
|---|---|
| cagcaggcta atgattttcc tatt | 24 |

<210> SEQ ID NO 205
<211> LENGTH: 30
<212> TYPE: DNA
<213> ORGANISM: Homo sapiens

<400> SEQUENCE: 205

|  |  |
|---|---|
| cagagctggg acaatcttaa gatgcctgtt | 30 |

<210> SEQ ID NO 206
<211> LENGTH: 30
<212> TYPE: DNA
<213> ORGANISM: Homo sapiens

<400> SEQUENCE: 206

|  |  |
|---|---|
| cagagctatg acgtttttcc tattaatcgt | 30 |

<210> SEQ ID NO 207
<211> LENGTH: 21
<212> TYPE: DNA
<213> ORGANISM: Homo sapiens

<400> SEQUENCE: 207

```
cagagcgatc tttatttccc t                                          21

<210> SEQ ID NO 208
<211> LENGTH: 24
<212> TYPE: DNA
<213> ORGANISM: Homo sapiens

<400> SEQUENCE: 208
cagagctatg acgttactcc tcgt                                       24

<210> SEQ ID NO 209
<211> LENGTH: 27
<212> TYPE: DNA
<213> ORGANISM: Homo sapiens

<400> SEQUENCE: 209
cagagccgtg accctgttgg ttttcct                                    27

<210> SEQ ID NO 210
<211> LENGTH: 24
<212> TYPE: DNA
<213> ORGANISM: Homo sapiens

<400> SEQUENCE: 210
cagagctatg acctttctcc tcgt                                       24

<210> SEQ ID NO 211
<211> LENGTH: 30
<212> TYPE: DNA
<213> ORGANISM: Homo sapiens

<400> SEQUENCE: 211
cagagctatg acttttctca ttatttttt                                  30

<210> SEQ ID NO 212
<211> LENGTH: 27
<212> TYPE: DNA
<213> ORGANISM: Homo sapiens

<400> SEQUENCE: 212
cagagctatg accttcgtta ttctcat                                    27

<210> SEQ ID NO 213
<211> LENGTH: 24
<212> TYPE: DNA
<213> ORGANISM: Homo sapiens

<400> SEQUENCE: 213
cagagctatg accttcgtaa tcgt                                       24

<210> SEQ ID NO 214
<211> LENGTH: 27
<212> TYPE: DNA
<213> ORGANISM: Homo sapiens

<400> SEQUENCE: 214
cagagctatg actttactta tggttct                                    27

<210> SEQ ID NO 215
<211> LENGTH: 24
<212> TYPE: DNA
<213> ORGANISM: Homo sapiens
```

```
<400> SEQUENCE: 215
cagcagttta atgattctcc ttat                                          24

<210> SEQ ID NO 216
<211> LENGTH: 27
<212> TYPE: DNA
<213> ORGANISM: Homo sapiens

<400> SEQUENCE: 216
cagagctatg acatttctgg ttatcct                                       27

<210> SEQ ID NO 217
<211> LENGTH: 30
<212> TYPE: DNA
<213> ORGANISM: Homo sapiens

<400> SEQUENCE: 217
cagagccgtg acctttatta tgtttattat                                    30

<210> SEQ ID NO 218
<211> LENGTH: 24
<212> TYPE: DNA
<213> ORGANISM: Homo sapiens

<400> SEQUENCE: 218
cagagctatg accgttctat gtgg                                          24

<210> SEQ ID NO 219
<211> LENGTH: 27
<212> TYPE: DNA
<213> ORGANISM: Homo sapiens

<400> SEQUENCE: 219
cagagctggg acgttcagac tgataag                                       27

<210> SEQ ID NO 220
<211> LENGTH: 27
<212> TYPE: DNA
<213> ORGANISM: Homo sapiens

<400> SEQUENCE: 220
cagagctggg acccttctca ttattat                                       27

<210> SEQ ID NO 221
<211> LENGTH: 27
<212> TYPE: DNA
<213> ORGANISM: Homo sapiens

<400> SEQUENCE: 221
cagagctatg acattatgcc tgagcgt                                       27

<210> SEQ ID NO 222
<211> LENGTH: 27
<212> TYPE: DNA
<213> ORGANISM: Homo sapiens

<400> SEQUENCE: 222
cagagcatgg actttcgtct tatgcat                                       27

<210> SEQ ID NO 223
<211> LENGTH: 27
<212> TYPE: DNA
<213> ORGANISM: Homo sapiens
```

-continued

```
<400> SEQUENCE: 223
cagagctttg acatgattca tccttat                                               27

<210> SEQ ID NO 224
<211> LENGTH: 21
<212> TYPE: DNA
<213> ORGANISM: Homo sapiens

<400> SEQUENCE: 224
cagagcgact ttcctgttat g                                                     21

<210> SEQ ID NO 225
<211> LENGTH: 21
<212> TYPE: DNA
<213> ORGANISM: Homo sapiens

<400> SEQUENCE: 225
cagagcgaca atccttatct t                                                     21

<210> SEQ ID NO 226
<211> LENGTH: 12
<212> TYPE: DNA
<213> ORGANISM: Homo sapiens

<400> SEQUENCE: 226
tttatggata tt                                                               12

<210> SEQ ID NO 227
<211> LENGTH: 12
<212> TYPE: DNA
<213> ORGANISM: Homo sapiens

<400> SEQUENCE: 227
ggttttgatt at                                                               12

<210> SEQ ID NO 228
<211> LENGTH: 12
<212> TYPE: DNA
<213> ORGANISM: Homo sapiens

<400> SEQUENCE: 228
tttcttgata tt                                                               12

<210> SEQ ID NO 229
<211> LENGTH: 24
<212> TYPE: DNA
<213> ORGANISM: Homo sapiens

<400> SEQUENCE: 229
acttttccta ttgatgctga ttct                                                  24

<210> SEQ ID NO 230
<211> LENGTH: 15
<212> TYPE: DNA
<213> ORGANISM: Homo sapiens

<400> SEQUENCE: 230
ggtcatgttg attat                                                            15

<210> SEQ ID NO 231
<211> LENGTH: 27
<212> TYPE: DNA
```

<210> SEQ ID NO 231
<211> LENGTH: 27
<212> TYPE: DNA
<213> ORGANISM: Homo sapiens

<400> SEQUENCE: 231
tattggcgtg gtctttcttt tgatatt                                27

<210> SEQ ID NO 232
<211> LENGTH: 12
<212> TYPE: DNA
<213> ORGANISM: Homo sapiens

<400> SEQUENCE: 232 tttttttgatt at                                               12

<210> SEQ ID NO 233
<211> LENGTH: 36
<212> TYPE: DNA
<213> ORGANISM: Homo sapiens

<400> SEQUENCE: 233
ggtctttatt gggctgttta tccttatttt gatttt                     36

<210> SEQ ID NO 234
<211> LENGTH: 33
<212> TYPE: DNA
<213> ORGANISM: Homo sapiens

<400> SEQUENCE: 234
cttgatactt attatcctga tcttttttgat tat                       33

<210> SEQ ID NO 235
<211> LENGTH: 21
<212> TYPE: DNA
<213> ORGANISM: Homo sapiens

<400> SEQUENCE: 235
acttattatt attttgattc t                                     21

<210> SEQ ID NO 236
<211> LENGTH: 33
<212> TYPE: DNA
<213> ORGANISM: Homo sapiens

<400> SEQUENCE: 236
tatatggctt atatggctga ggctattgat gtt                        33

<210> SEQ ID NO 237
<211> LENGTH: 51
<212> TYPE: DNA
<213> ORGANISM: Homo sapiens

<400> SEQUENCE: 237
cttgttggta ttgttggtta taagcctgat gagcttcttt attttgatgt t    51

<210> SEQ ID NO 238
<211> LENGTH: 27
<212> TYPE: DNA
<213> ORGANISM: Homo sapiens

<400> SEQUENCE: 238
tatggtgctt attttggtct tgattat                                27

<210> SEQ ID NO 239
<211> LENGTH: 27

```
<212> TYPE: DNA
<213> ORGANISM: Homo sapiens

<400> SEQUENCE: 239
ggttatgctg atatttcttt tgattat                                    27

<210> SEQ ID NO 240
<211> LENGTH: 21
<212> TYPE: DNA
<213> ORGANISM: Homo sapiens

<400> SEQUENCE: 240
tattatcttc ttcttgatta t                                          21

<210> SEQ ID NO 241
<211> LENGTH: 48
<212> TYPE: DNA
<213> ORGANISM: Homo sapiens

<400> SEQUENCE: 241
tggtctgatc agtcttatca ttattattgg catccttatt ttgatgtt             48

<210> SEQ ID NO 242
<211> LENGTH: 21
<212> TYPE: DNA
<213> ORGANISM: Homo sapiens

<400> SEQUENCE: 242
cttattggtt attttgatct t                                          21

<210> SEQ ID NO 243
<211> LENGTH: 36
<212> TYPE: DNA
<213> ORGANISM: Homo sapiens

<400> SEQUENCE: 243
cttactaatt attttgattc tatttattat gatcat                          36

<210> SEQ ID NO 244
<211> LENGTH: 36
<212> TYPE: DNA
<213> ORGANISM: Homo sapiens

<400> SEQUENCE: 244
cttgttggtg gtggttatga tcttatgttt gattct                          36

<210> SEQ ID NO 245
<211> LENGTH: 39
<212> TYPE: DNA
<213> ORGANISM: Homo sapiens

<400> SEQUENCE: 245
tatgttactt atggttatga tgattatcat tttgattat                       39

<210> SEQ ID NO 246
<211> LENGTH: 18
<212> TYPE: DNA
<213> ORGANISM: Homo sapiens

<400> SEQUENCE: 246
tctggttatc ttgattat                                              18

<210> SEQ ID NO 247
```

```
<211> LENGTH: 54
<212> TYPE: DNA
<213> ORGANISM: Homo sapiens

<400> SEQUENCE: 247
tatattggtt atactaatgt tatggatatt cgtcctggtt tttatcttga ttat        54

<210> SEQ ID NO 248
<211> LENGTH: 36
<212> TYPE: DNA
<213> ORGANISM: Homo sapiens

<400> SEQUENCE: 248
tttcgtgctt atggtgatga tttttatttt gatgtt                            36

<210> SEQ ID NO 249
<211> LENGTH: 45
<212> TYPE: DNA
<213> ORGANISM: Homo sapiens

<400> SEQUENCE: 249
attatgtggt ctgattatgg tcagcttgtt aagggtggtg atatt                  45

<210> SEQ ID NO 250
<211> LENGTH: 33
<212> TYPE: DNA
<213> ORGANISM: Homo sapiens

<400> SEQUENCE: 250
tattatgtta ctgatactgc ttattttgat tat                               33

<210> SEQ ID NO 251
<211> LENGTH: 33
<212> TYPE: DNA
<213> ORGANISM: Homo sapiens

<400> SEQUENCE: 251
catgattttg atggttctat ttttatggat ttt                               33

<210> SEQ ID NO 252
<211> LENGTH: 36
<212> TYPE: DNA
<213> ORGANISM: Homo sapiens

<400> SEQUENCE: 252
tatgctggtc atcagtatga gttttttttt gatttt                            36

<210> SEQ ID NO 253
<211> LENGTH: 33
<212> TYPE: DNA
<213> ORGANISM: Homo sapiens

<400> SEQUENCE: 253
ctttatgctg atgctgatat ttattttgat tat                               33

<210> SEQ ID NO 254
<211> LENGTH: 27
<212> TYPE: DNA
<213> ORGANISM: Homo sapiens

<400> SEQUENCE: 254
actaagtatg ttggttctga ggatgtt                                      27
```

```
<210> SEQ ID NO 255
<211> LENGTH: 27
<212> TYPE: DNA
<213> ORGANISM: Homo sapiens

<400> SEQUENCE: 255
tatcgttatc ctcatatgtt tgatttt                                          27

<210> SEQ ID NO 256
<211> LENGTH: 33
<212> TYPE: DNA
<213> ORGANISM: Homo sapiens

<400> SEQUENCE: 256 cttttttgctg gtcttgagct ttattttgat tat                                  33

<210> SEQ ID NO 257
<211> LENGTH: 24
<212> TYPE: DNA
<213> ORGANISM: Homo sapiens

<400> SEQUENCE: 257
ggtggttttt ttaatatgga ttat                                             24

<210> SEQ ID NO 258
<211> LENGTH: 30
<212> TYPE: DNA
<213> ORGANISM: Homo sapiens

<400> SEQUENCE: 258
ggttatattc cttatcatct ttttgattat                                       30

<210> SEQ ID NO 259
<211> LENGTH: 36
<212> TYPE: DNA
<213> ORGANISM: Homo sapiens

<400> SEQUENCE: 259
tattatggtt ttgagtatga tcttcttttt gataat                                36

<210> SEQ ID NO 260
<211> LENGTH: 24
<212> TYPE: DNA
<213> ORGANISM: Homo sapiens

<400> SEQUENCE: 260
attacttata ttggttatga tttt                                             24

<210> SEQ ID NO 261
<211> LENGTH: 21
<212> TYPE: DNA
<213> ORGANISM: Homo sapiens

<400> SEQUENCE: 261
caggagtggt atatggatta t                                                21

<210> SEQ ID NO 262
<211> LENGTH: 33
<212> TYPE: DNA
<213> ORGANISM: Homo sapiens

<400> SEQUENCE: 262
ctttatcctg aggatcttat ttattttgat tat                                   33
```

<210> SEQ ID NO 263
<211> LENGTH: 45
<212> TYPE: DNA
<213> ORGANISM: Homo sapiens

<400> SEQUENCE: 263
tggatgactc ctcctggtca ttattatggt tatacttttg atgtt                45

<210> SEQ ID NO 264
<211> LENGTH: 36
<212> TYPE: DNA
<213> ORGANISM: Homo sapiens

<400> SEQUENCE: 264
cttcgtgttc atgattatgc tatgtatttt gatctt                          36

<210> SEQ ID NO 265
<211> LENGTH: 39
<212> TYPE: DNA
<213> ORGANISM: Homo sapiens

<400> SEQUENCE: 265
tttgtttctt ataatggttc tgttccttat tttgattat                       39

<210> SEQ ID NO 266
<211> LENGTH: 33
<212> TYPE: DNA
<213> ORGANISM: Homo sapiens

<400> SEQUENCE: 266
attattggtg attatgttat ttttttgat gtt                              33

<210> SEQ ID NO 267
<211> LENGTH: 33
<212> TYPE: DNA
<213> ORGANISM: Homo sapiens

<400> SEQUENCE: 267 cttttactt atccttttct ttattttgat gtt                              33

<210> SEQ ID NO 268
<211> LENGTH: 33
<212> TYPE: DNA
<213> ORGANISM: Homo sapiens

<400> SEQUENCE: 268
attcttactg gtcacgttct tctttttgat tat                             33

<210> SEQ ID NO 269
<211> LENGTH: 645
<212> TYPE: DNA
<213> ORGANISM: Homo sapiens

<400> SEQUENCE: 269
caggtgcaat tggtggaaag cggcggcggc ctggtgcaac cgggcggcag cctgcgtctg     60
agctgcgcgg cctccggatt taccttagc agctatgcga tgagctgggt gcgccaagcc    120
cctgggaagg gtctcgagtg ggtgagcgcg attagcggta gcggcggcag cacctattat    180
gcggatagcg tgaaaggccg ttttaccatt tcacgtgata attcgaaaaa cacccctgtat    240 ctgcaaaatga acagcctgcg tgcggaagat acggccgtgt attattgcgc gcgttttatg    300
gatatttggg gccaaggcac cctggtgacg gttagctcag cgtcgaccaa aggtccaagc    360

```
gtgtttccgc tggctccgag cagcaaaagc accagcggcg gcacggctgc cctgggctgc      420
ctggttaaag attatttccc ggaaccagtc accgtgagct ggaacagcgg ggcgctgacc      480
agcggcgtgc atacctttcc ggcggtgctg caaagcagcg gcctgtatag cctgagcagc      540
gttgtgaccg tgccgagcag cagcttaggc actcagacct atatttgcaa cgtgaaccat      600
aaaccgagca acaccaaagt ggataaaaaa gtggaaccga aaagc                      645

<210> SEQ ID NO 270
<211> LENGTH: 645
<212> TYPE: DNA
<213> ORGANISM: Homo sapiens

<400> SEQUENCE: 270
caggtgcaat tggtggaaag cggcggcggc ctggtgcaac cgggcggcag cctgcgtctg      60
agctgcgcgg cctccggatt tacctttagc agctatgcga tgagctgggt gcgccaagcc     120
cctgggaagg gtctcgagtg ggtgagcgcg attagcggta gcggcggcag cacctattat     180
gcggatagcg tgaaaggccg ttttaccatt tcacgtgata attcgaaaaa caccctgtat     240
ctgcaaatga acagcctgcg tgcggaagat acggccgtgt attattcgc gcgtggtttt      300 gattattggg gccaaggcac cctggtgacg gttagctcag cgtcgaccaa aggtccaagc     360
gtgtttccgc tggctccgag cagcaaaagc accagcggcg gcacggctgc cctgggctgc     420
ctggttaaag attatttccc ggaaccagtc accgtgagct ggaacagcgg ggcgctgacc     480
agcggcgtgc atacctttcc ggcggtgctg caaagcagcg gcctgtatag cctgagcagc     540
gttgtgaccg tgccgagcag cagcttaggc actcagacct atatttgcaa cgtgaaccat     600
aaaccgagca acaccaaagt ggataaaaaa gtggaaccga aaagc                      645

<210> SEQ ID NO 271
<211> LENGTH: 645
<212> TYPE: DNA
<213> ORGANISM: Homo sapiens

<400> SEQUENCE: 271
caggtgcaat tggtggaaag cggcggcggc ctggtgcaac cgggcggcag cctgcgtctg      60
agctgcgcgg cctccggatt tacctttagc agctatgcga tgagctgggt gcgccaagcc     120
cctgggaagg gtctcgagtg ggtgagcgcg attagcggta gcggcggcag cacctattat     180
gcggatagcg tgaaaggccg ttttaccatt tcacgtgata attcgaaaaa caccctgtat     240
ctgcaaatga acagcctgcg tgcggaagat acggccgtgt attattcgc gcgttttctt      300 gatatttggg gccaaggcac cctggtgacg gttagctcag cgtcgaccaa aggtccaagc     360
gtgtttccgc tggctccgag cagcaaaagc accagcggcg gcacggctgc cctgggctgc     420
ctggttaaag attatttccc ggaaccagtc accgtgagct ggaacagcgg ggcgctgacc     480
agcggcgtgc atacctttcc ggcggtgctg caaagcagcg gcctgtatag cctgagcagc     540
gttgtgaccg tgccgagcag cagcttaggc actcagacct atatttgcaa cgtgaaccat     600
aaaccgagca acaccaaagt ggataaaaaa gtggaaccga aaagc                      645

<210> SEQ ID NO 272
<211> LENGTH: 657
<212> TYPE: DNA
<213> ORGANISM: Homo sapiens

<400> SEQUENCE: 272
```

| | |
|---|---|
| caggtgcaat tggtggaaag cggcggcggc ctggtgcaac cgggcggcag cctgcgtctg | 60 |
| agctgcgcgg cctccggatt tacctttagc agctatgcga tgagctgggt gcgccaagcc | 120 |
| cctgggaagg gtctcgagtg ggtgagcgcg attagcggta gcggcggcag cacctattat | 180 |
| gcggatagcg tgaaaggccg ttttaccatt tcacgtgata attcgaaaaa cacc ctgtat | 240 |
| ctgcaaatga acagcctgcg tgcggaagat acggccgtgt attattgcgc gcgtactttt | 300 |
| cctattgatg ctgattcttg gggccaaggc accctggtga cggttagctc agcgtcgacc | 360 |
| aaaggtccaa gcgtgtttcc gctggctccg agcagcaaaa gcaccagcgg cggcacggct | 420 |
| gccctgggct gcctggttaa agattatttc ccggaaccag tcaccgtgag ctggaacagc | 480 |
| ggggcgctga ccagcggcgt gcataccttt ccggcggtgc tgcaaagcag cggcctgtat | 540 |
| agcctgagca gcgttgtgac cgtgccgagc agcagcttag gcactcagac ctatatttgc | 600 |
| aacgtgaacc ataaaccgag caacaccaaa gtggataaaa aagtggaacc gaaaagc | 657 |

<210> SEQ ID NO 273
<211> LENGTH: 648
<212> TYPE: DNA
<213> ORGANISM: Homo sapiens

<400> SEQUENCE: 273

| | |
|---|---|
| caggtgcaat tggtggaaag cggcggcggc ctggtgcaac cgggcggcag cctgcgtctg | 60 |
| agctgcgcgg cctccggatt tacctttagc agctatgcga tgagctgggt gcgccaagcc | 120 |
| cctgggaagg gtctcgagtg ggtgagcgcg attagcggta gcggcggcag cacctattat | 180 |
| gcggatagcg tgaaaggccg ttttaccatt tcacgtgata attcgaaaaa cacc ctgtat | 240 |
| ctgcaaatga acagcctgcg tgcggaagat acggccgtgt attattgcgc gcgtggtcat | 300 |
| gttgattatt ggggccaagg caccctggtg acggttagct cagcgtcgac caaaggtcca | 360 |
| agcgtgtttc cgctggctcc gagcagcaaa agcaccagcg gcggcacggc tgccctgggc | 420 |
| tgcctggtta agattatttt cccggaacca gtcaccgtga gctggaacag cggggcgctg | 480 |
| accagcggcg tgcataccct tccgcggtg ctgcaaagca gcggcctgta tagcctgagc | 540 |
| agcgttgtga ccgtgccgag cagcagctta ggcactcaga cctatatttg caacgtgaac | 600 |
| cataaaccga gcaacaccaa agtggataaa aaagtggaac cgaaaagc | 648 |

<210> SEQ ID NO 274
<211> LENGTH: 660
<212> TYPE: DNA
<213> ORGANISM: Homo sapiens

<400> SEQUENCE: 274

| | |
|---|---|
| caggtgcaat tggtggaaag cggcggcggc ctggtgcaac cgggcggcag cctgcgtctg | 60 |
| agctgcgcgg cctccggatt tacctttagc agctatgcga tgagctgggt gcgccaagcc | 120 |
| cctgggaagg gtctcgagtg ggtgagcgcg attagcggta gcggcggcag cacctattat | 180 |
| gcggatagcg tgaaaggccg ttttaccatt tcacgtgata attcgaaaaa cacc ctgtat | 240 |
| ctgcaaatga acagcctgcg tgcggaagat acggccgtgt attattgcgc gcgttattgg | 300 |
| cgtggtcttt cttttgatat ttggggccaa ggcaccctgg tgacggttag ctcagcgtcg | 360 |
| accaaaggtc aagcgtgtt ccgctggct ccgagcagca aaagcaccag cggcggcacg | 420 |
| gctgccctgg gctgcctggt taagattat ttcccggaac cagtcaccgt gagctggaac | 480 |
| agcggggcgc tgaccagcgg cgtgcatacc tttccggcgg tgctgcaaag cagcggcctg | 540 |
| tatagcctga gcagcgttgt gaccgtgccg agcagcagct taggcactca gacctatatt | 600 |

-continued

```
tgcaacgtga accataaacc gagcaacacc aaagtggata aaaaagtgga accgaaaagc    660
```

<210> SEQ ID NO 275
<211> LENGTH: 645
<212> TYPE: DNA
<213> ORGANISM: Homo sapiens

<400> SEQUENCE: 275

```
caggtgcaat tggtggaaag cggcggcggc ctggtgcaac cgggcggcag cctgcgtctg     60
agctgcgcgg cctccggatt tacctttagc agctatgcga tgagctgggt gcgccaagcc    120
cctgggaagg gtctcgagtg ggtgagcgcg attagcggta gcggcggcag cacctattat    180
gcggatagcg tgaaaggccg ttttaccatt tcacgtgata attcgaaaaa cacccctgtat   240
ctgcaaatga acagcctgcg tgcggaagat acggccgtgt attattgcgc gcgtttttt    300
gattattggg gccaaggcac cctggtgacg gttagctcag cgtcgaccaa aggtccaagc    360
gtgtttccgc tggctccgag cagcaaaagc accagcggcg gcacggctgc cctgggctgc    420
ctggttaaag attatttccc ggaaccagtc accgtgagct ggaacagcgg ggcgctgacc    480
agcggcgtgc ataccttcc ggcggtgctg caaagcagcg gcctgtatag cctgagcagc     540
gttgtgaccg tgccgagcag cagcttaggc actcagacct atatttgcaa cgtgaaccat    600
aaaccgagca caccaaagt ggataaaaa gtggaaccga aaagc                      645
```

<210> SEQ ID NO 276
<211> LENGTH: 669
<212> TYPE: DNA
<213> ORGANISM: Homo sapiens

<400> SEQUENCE: 276

```
caggtgcaat tggttcagtc tggcgcggaa gtgaaaaaac cgggcagcag cgtgaaagtg     60
agctgcaaag cctccggagg cacttttagc agctatgcga ttagctgggt gcgccaagcc    120
cctgggcagg gtctcgagtg gatgggcggc attattccga ttttggcac ggcgaactac     180
gcgcagaagt ttcagggccg ggtgaccatt accgcggatg aaagcaccag caccgcgtat    240
atggaactga gcagcctgcg tagcgaagat acggccgtgt attattgcgc gcgtggtctt    300
tattgggctg ttatcctta ttttgattt tggggccaag gcaccctggt gacggttagc     360
tcagcgtcga ccaaaggtcc aagcgtgttt ccgctggctc cgagcagcaa aagcaccagc    420
ggcggcacgg ctgccctggg ctgcctggtt aaagattatt tcccggaacc agtcaccgtg    480
agctggaaca gcggggcgct gaccagcggc gtgcatacct tccggcggt gctgcaaagc    540
agcggcctgt atagcctgag cagcgttgtg accgtgccga gcagcagctt aggcactcag    600
acctatatt gcaacgtgaa ccataaaccg agcaacacca aagtggataa aaaagtggaa     660
ccgaaaagc                                                           669
```

<210> SEQ ID NO 277
<211> LENGTH: 666
<212> TYPE: DNA
<213> ORGANISM: Homo sapiens

<400> SEQUENCE: 277

```
caggtgcaat tggtggaaag cggcggcggc ctggtgcaac cgggcggcag cctgcgtctg     60
agctgcgcgg cctccggatt tacctttagc agctatgcga tgagctgggt gcgccaagcc    120
cctgggaagg gtctcgagtg ggtgagcgcg attagcggta gcggcggcag cacctattat    180
```

```
gcggatagcg tgaaaggccg ttttaccatt tcacgtgata attcgaaaaa caccctgtat    240
ctgcaaatga acagcctgcg tgcggaagat acggccgtgt attattgcgc gcgtcttgat    300
acttattatc ctgatctttt tgattattgg ggccaaggca ccctggtgac ggttagctca    360
gcgtcgacca aaggtccaag cgtgtttccg ctggctccga gcagcaaaag caccagcggc    420
ggcacggctg ccctgggctg cctggttaaa gattatttcc cggaaccagt caccgtgagc    480
tggaacagcg gggcgctgac cagcggcgtg cataccttc cggcggtgct gcaaagcagc    540
ggcctgtata gcctgagcag cgttgtgacc gtgccgagca gcagcttagg cactcagacc    600
tatatttgca acgtgaacca taaaccgagc aacaccaaag tggataaaaa agtggaaccg    660
aaaagc                                                               666
```

<210> SEQ ID NO 278
<211> LENGTH: 654
<212> TYPE: DNA
<213> ORGANISM: Homo sapiens
<400> SEQUENCE: 278

```
caggtgcaat tggttcagtc tggcgcggaa gtgaaaaaac cgggcagcag cgtgaaagtg     60
agctgcaaag cctccggagg cacttttagc agctatgcga ttagctgggt gcgccaagcc    120
cctgggcagg gtctcgagtg gatgggcggc attattccga ttttttggcac ggcgaactac    180 gcgcagaagt ttcagggccg ggtgaccatt accgcggatg aaagcaccag caccgcgtat    240
atggaactga gcagcctgcg tagcgaagat acggccgtgt attattgcgc gcgtacttat    300
tattattttg attcttgggg ccaaggcacc ctggtgacgg ttagctcagc gtcgaccaaa    360
ggtccaagcg tgtttccgct ggctccgagc agcaaaagca ccagcggcgg cacggctgcc    420
ctgggctgcc tggttaaaga ttatttcccg gaaccagtca ccgtgagctg gaacagcggg    480
gcgctgacca gcggcgtgca tacctttccg gcggtgctgc aaagcagcgg cctgtatagc    540
ctgagcagcg ttgtgaccgt gccgagcagc agcttaggca ctcagaccta tatttgcaac    600
gtgaaccata aaccgagcaa caccaaagtg gataaaaaag tggaaccgaa aagc         654
```

<210> SEQ ID NO 279
<211> LENGTH: 666
<212> TYPE: DNA
<213> ORGANISM: Homo sapiens
<400> SEQUENCE: 279

```
caggtgcaat tggtggaaag cggcggcggc ctggtgcaac cgggcggcag cctgcgtctg     60
agctgcgcgg cctccggatt tacctttagc agctatgcga tgagctgggt gcgccaagcc    120
cctgggaagg gtctcgagtg ggtgagcgcg attagcggta gcggcggcag cacctattat    180
gcggatagcg tgaaaggccg ttttaccatt tcacgtgata attcgaaaaa caccctgtat    240
ctgcaaatga acagcctgcg tgcggaagat acggccgtgt attattgcgc gcgttatatg    300
gcttatatgg ctgaggctat tgatgtttgg ggccaaggca ccctggtgac ggttagctca    360
gcgtcgacca aaggtccaag cgtgtttccg ctggctccga gcagcaaaag caccagcggc    420
ggcacggctg ccctgggctg cctggttaaa gattatttcc cggaaccagt caccgtgagc    480
tggaacagcg gggcgctgac cagcggcgtg cataccttc cggcggtgct gcaaagcagc    540
ggcctgtata gcctgagcag cgttgtgacc gtgccgagca gcagcttagg cactcagacc    600
tatatttgca acgtgaacca taaaccgagc aacaccaaag tggataaaaa agtggaaccg    660
aaaagc                                                               666
```

<210> SEQ ID NO 280
<211> LENGTH: 684
<212> TYPE: DNA
<213> ORGANISM: Homo sapiens

<400> SEQUENCE: 280

| | | | | | |
|---|---|---|---|---|---|
| caggtgcaat | tggttcagag | cggcgcggaa | gtgaaaaaac | cgggcgcgag | cgtgaaagtg | 60 |
| agctgcaaag | cctccggata | tacctttacc | agctattata | tgcactgggt | ccgccaagcc | 120 |
| cctgggcagg | gtctcgagtg | gatgggctgg | attaacccga | atagcggcgg | cacgaactac | 180 |
| gcgcagaagt | ttcagggccg | ggtgaccatg | acccgtgata | ccagcattag | caccgcgtat | 240 |
| atggaactga | gcagcctgcg | tagcgaagat | acggccgtgt | attattgcgc | gcgtcttgtt | 300 |
| ggtattgttg | gttataagcc | tgatgagctt | ctttattttg | atgtttgggg | ccaaggcacc | 360 |
| ctggtgacgg | ttagctcagc | gtcgaccaaa | ggtccaagcg | tgtttccgct | ggctccgagc | 420 |
| agcaaaagca | ccagcggcgg | cacggctgcc | ctgggctgcc | tggttaaaga | ttatttcccg | 480 |
| gaaccagtca | ccgtgagctg | gaacagcggg | gcgctgacca | gcggcgtgca | tacctttccg | 540 |
| gcggtgctgc | aaagcagcgg | cctgtatagc | ctgagcagcg | ttgtgaccgt | gccgagcagc | 600 |
| agcttaggca | ctcagaccta | tatttgcaac | gtgaaccata | aaccgagcaa | caccaaagtg | 660 |
| gataaaaaag | tggaaccgaa | aagc | | | | 684 |

<210> SEQ ID NO 281
<211> LENGTH: 660
<212> TYPE: DNA
<213> ORGANISM: Homo sapiens

<400> SEQUENCE: 281

| | | | | | |
|---|---|---|---|---|---|
| caggtgcaat | tggtggaaag | cggcggcggc | ctggtgcaac | cgggcggcag | cctgcgtctg | 60 |
| agctgcgcgg | cctccggatt | tacctttagc | agctatgcga | tgagctgggt | gcgccaagcc | 120 |
| cctgggaagg | gtctcgagtg | ggtgagcgcg | attagcggta | gcggcggcag | cacctattat | 180 |
| gcggatagcg | tgaaaggccg | ttttaccatt | tcacgtgata | attcgaaaaa | cacccctgtat | 240 |
| ctgcaaatga | acagcctgcg | tgcggaagat | acggccgtgt | attattgcgc | gcgttatggt | 300 |
| gcttattttg | gtcttgatta | ttggggccaa | ggcaccctgg | tgacggttag | ctcagcgtcg | 360 |
| accaaaggtc | caagcgtgtt | tccgctggct | ccgagcagca | aaagcaccag | cggcggcacg | 420 |
| gctgccctgg | gctgcctggt | taaagattat | ttcccggaac | cagtcaccgt | gagctggaac | 480 |
| agcggggcgc | tgaccagcgg | cgtgcatacc | tttccggcgg | tgctgcaaag | cagcggcctg | 540 |
| tatagcctga | gcagcgttgt | gaccgtgccg | agcagcagct | taggcactca | gacctatatt | 600 |
| tgcaacgtga | accataaacc | gagcaacacc | aaagtggata | aaaagtgga | accgaaaagc | 660 |

<210> SEQ ID NO 282
<211> LENGTH: 669
<212> TYPE: DNA
<213> ORGANISM: Homo sapiens

<400> SEQUENCE: 282

| | | | | | |
|---|---|---|---|---|---|
| caggtgcaat | tgcaacagtc | tggtccgggc | ctggtgaaac | cgagccaaac | cctgagcctg | 60 |
| acctgtgcga | tttccggaga | tagcgtgagc | agcaacagcg | cggcgtggaa | ctggattcgc | 120 |
| cagtctcctg | gcgtggcct | cgagtggctg | ggccgtacct | attatcgtag | caaatggtat | 180 |
| aacgattatg | cggtgagcgt | gaaaagccgg | attaccatca | acccgatac | ttcgaaaaac | 240 |

```
cagtttagcc tgcaactgaa cagcgtgacc ccggaagata cggccgtgta ttattgcgcg      300
cgtggttatg ctgatatttc ttttgattat tggggccaag gcaccctggt gacggttagc      360
tcagcgtcga ccaaaggtcc aagcgtgttt ccgctggctc cgagcagcaa aagcaccagc      420
ggcggcacgg ctgccctggg ctgcctggtt aaagattatt tcccggaacc agtcaccgtg      480
agctggaaca gcggggcgct gaccagcggc gtgcatacct ttccggcggt gctgcaaagc      540
agcggcctgt atagcctgag cagcgttgtg accgtgccga gcagcagctt aggcactcag      600
acctatattt gcaacgtgaa ccataaaccg agcaacacca agtggataa aaaagtggaa      660 ccgaaaagc                                                             669
```

<210> SEQ ID NO 283
<211> LENGTH: 654
<212> TYPE: DNA
<213> ORGANISM: Homo sapiens

<400> SEQUENCE: 283

```
caggtgcaat tggtggaaag cggcggcggc ctggtgcaac cgggcggcag cctgcgtctg       60
agctgcgcgg cctccggatt tacctttagc agctatgcga tgagctgggt gcgccaagcc      120
cctgggaagg gtctcgagtg ggtgagcgcg attagcggta gcggcggcag cacctattat      180
gcggatagcg tgaaaggccg ttttaccatt tcacgtgata attcgaaaaa cacccctgtat     240 ctgcaaatga acagcctgcg tgcggaagat acggccgtgt attattgcgc gcgttattat      300
cttcttcttg attattgggg ccaaggcacc ctggtgacgg ttagctcagc gtcgaccaaa      360
ggtccaagcg tgtttccgct ggctccgagc agcaaaagca ccagcggcgg cacggctgcc      420
ctgggctgcc tggttaaaga ttatttcccg gaaccagtca ccgtgagctg gaacagcggg      480
gcgctgacca gcggcgtgca tacctttccg gcggtgctgc aaagcagcgg cctgtatagc      540
ctgagcagcg ttgtgaccgt gccgagcagc agcttaggca ctcagaccta tatttgcaac      600
gtgaaccata aaccgagcaa caccaaagtg gataaaaaag tggaaccgaa aagc            654
```

<210> SEQ ID NO 284
<211> LENGTH: 681
<212> TYPE: DNA
<213> ORGANISM: Homo sapiens

<400> SEQUENCE: 284

```
caggtgcaat tggttcagtc tggcgcggaa gtgaaaaaac cgggcagcag cgtgaaagtg       60
agctgcaaag cctccggagg cactttagc agctatgcga ttagctgggt gcgccaagcc      120
cctgggcagg gtctcgagtg gatgggcggc attattccga tttttggcac ggcgaactac      180
gcgcagaagt ttcagggccg ggtgaccatt accgcggatg aaagcaccag caccgcgtat      240
atggaactga gcagcctgcg tagcgaagat acggccgtgt attattgcgc gcgttggtct      300
gatcagtctt atcattatta ttggcatcct tattttgatg tttggggcca aggcaccctg      360
gtgacggtta gctcagcgtc gaccaaaggt ccaagcgtgt ttccgctggc tccgagcagc      420
aaaagcacca gcggcggcac ggctgccctg ggctgcctgg ttaaagatta tttcccggaa      480
ccagtcaccg tgagctggaa cagcggggcg ctgaccagcg cgtgcatac ctttccggcg      540 gtgctgcaaa gcagcggcct gtatagcctg agcagcgttg tgaccgtgcc gagcagcagc      600
ttaggcactc agacctatat ttgcaacgtg aaccataaac cgagcaacac caaagtggat      660
aaaaaagtgg aaccgaaaag c                                               681
```

-continued

<210> SEQ ID NO 285
<211> LENGTH: 654
<212> TYPE: DNA
<213> ORGANISM: Homo sapiens

<400> SEQUENCE: 285

| | | | | | |
|---|---|---|---|---|---|
| caggtgcaat | tggtggaaag | cggcggcggc | ctggtgcaac | cgggcggcag | cctgcgtctg | 60 |
| agctgcgcgg | cctccggatt | tacctttagc | agctatgcga | tgagctgggt | gcgccaagcc | 120 |
| cctgggaagg | gtctcgagtg | ggtgagcgcg | attagcggta | gcggcggcag | cacctattat | 180 |
| gcggatagcg | tgaaaggccg | ttttaccatt | tcacgtgata | attcgaaaaa | caccctgtat | 240 |
| ctgcaaatga | acagcctgcg | tgcggaagat | acggccgtgt | attattgcgc | gcgtcttatt | 300 |
| ggttattttg | atctttgggg | ccaaggcacc | ctggtgacgg | ttagctcagc | gtcgaccaaa | 360 |
| ggtccaagcg | tgtttccgct | ggctccgagc | agcaaaagca | ccagcggcgg | cacggctgcc | 420 |
| ctgggctgcc | tggttaaaga | ttatttcccg | gaaccagtca | ccgtgagctg | gaacagcggg | 480 |
| gcgctgacca | gcggcgtgca | tacctttccg | gcggtgctgc | aaagcagcgg | cctgtatagc | 540 |
| ctgagcagcg | ttgtgaccgt | gccgagcagc | agcttaggca | ctcagaccta | tatttgcaac | 600 |
| gtgaaccata | aaccgagcaa | caccaaagtg | gataaaaaag | tggaaccgaa | aagc | 654 |

<210> SEQ ID NO 286
<211> LENGTH: 669
<212> TYPE: DNA
<213> ORGANISM: Homo sapiens

<400> SEQUENCE: 286

| | | | | | |
|---|---|---|---|---|---|
| caggtgcaat | tggttcagag | cggcgcggaa | gtgaaaaaac | cgggcgaaag | cctgaaaatt | 60 |
| agctgcaaag | gttccggata | ttcctttacg | agctattgga | ttggctgggt | gcgccagatg | 120 |
| cctgggaagg | gtctcgagtg | gatgggcatt | atttatccgg | gcgatagcga | tacccgttat | 180 |
| tctccgagct | ttcagggcca | ggtgaccatt | agcgcgggata | aaagcattag | caccgcgtat | 240 |
| cttcaatgga | gcagcctgaa | agcgagcgat | acggccatgt | attattgcgc | gcgtcttact | 300 |
| aattattttg | attctattta | ttatgatcat | tggggccaag | gcaccctggt | gacggttagc | 360 |
| tcagcgtcga | ccaaaggtcc | aagcgtgttt | ccgctggctc | cgagcagcaa | agcaccagc | 420 |
| ggcggcacgg | ctgccctggg | ctgcctggtt | aaagattatt | tcccggaacc | agtcaccgtg | 480 |
| agctggaaca | gcggggcgct | gaccagcggc | gtgcatacct | ttccggcggt | gctgcaaagc | 540 |
| agcggcctgt | atagcctgag | cagcgttgtg | accgtgccga | gcagcagctt | aggcactcag | 600 |
| acctatattt | gcaacgtgaa | ccataaaccg | agcaacacca | aagtggataa | aaaagtggaa | 660 |
| ccgaaaagc | | | | | | 669 |

<210> SEQ ID NO 287
<211> LENGTH: 669
<212> TYPE: DNA
<213> ORGANISM: Homo sapiens

<400> SEQUENCE: 287

| | | | | | |
|---|---|---|---|---|---|
| caggtgcaat | tggttcagag | cggcgcggaa | gtgaaaaaac | cgggcgaaag | cctgaaaatt | 60 |
| agctgcaaag | gttccggata | ttcctttacg | agctattgga | ttggctgggt | gcgccagatg | 120 |
| cctgggaagg | gtctcgagtg | gatgggcatt | atttatccgg | gcgatagcga | tacccgttat | 180 |
| tctccgagct | ttcagggcca | ggtgaccatt | agcgcgggata | aaagcattag | caccgcgtat | 240 |
| cttcaatgga | gcagcctgaa | agcgagcgat | acggccatgt | attattgcgc | gcgtcttgtt | 300 |

```
ggtggtggtt atgatcttat gtttgattct tggggccaag gcaccctggt gacggttagc      360
tcagcgtcga ccaaaggtcc aagcgtgttt ccgctggctc cgagcagcaa aagcaccagc      420
ggcggcacgg ctgccctggg ctgcctggtt aaagattatt tcccggaacc agtcaccgtg      480
agctggaaca gcggggcgct gaccagcggc gtgcatacct ttccggcggt gctgcaaagc      540
agcggcctgt atagcctgag cagcgttgtg accgtgccga gcagcagctt aggcactcag      600
acctatattt gcaacgtgaa ccataaaccg agcaacacca agtggataaa aaagtggaa       660 ccgaaaagc                                                              669
```

<210> SEQ ID NO 288
<211> LENGTH: 672
<212> TYPE: DNA
<213> ORGANISM: Homo sapiens

<400> SEQUENCE: 288

```
caggtgcaat tggttcagag cggcgcggaa gtgaaaaaac cgggcgaaag cctgaaaatt       60
agctgcaaag gttccggata ttcctttacg agctattgga ttggctgggt cgccagatg      120 cctgggaagg tctcgagtg gatgggcatt atttatccgg gcgatagcga tacccgttat      180
tctccgagct ttcagggcca ggtgaccatt agcgcggata aaagcattag caccgcgtat      240
cttcaatgga gcagcctgaa agcgagcgat acggccatgt attattgcgc gcgttatgtt      300
acttatggtt atgatgatta tcattttgat tattggggcc aaggcaccct ggtgacggtt      360
agctcagcgt cgaccaaagg tccaagcgtg tttccgctgg ctccgagcag caaaagcacc      420
agcggcggca cggctgccct gggctgcctg gttaaagatt atttcccgga accagtcacc      480
gtgagctgga cagcggggc gctgaccagc ggcgtgcata cctttccggc ggtgctgcaa      540
agcagcggcc tgtatagcct gagcagcgtt gtgaccgtgc cgagcagcag cttaggcact      600
cagacctata tttgcaacgt gaaccataaa ccgagcaaca ccaaagtgga taaaaaagtg      660
gaaccgaaaa gc                                                         672
```

<210> SEQ ID NO 289
<211> LENGTH: 651
<212> TYPE: DNA
<213> ORGANISM: Homo sapiens

<400> SEQUENCE: 289

```
caggtgcaat tggttcagtc tggcgcggaa gtgaaaaaac cgggcagcag cgtgaaagtg       60
agctgcaaag cctccggagg cacttttagc agctatgcga ttagctgggt cgccaagcc      120 cctgggcagg tctcgagtg gatgggcggc attattccga ttttggcac ggcgaactac       180 gcgcagaagt ttcagggccg ggtgaccatt accgcggatg aaagcaccag caccgcgtat      240
atggaactga gcagcctgcg tagcgaagat acggccgtgt attattgcgc gcgttctggt      300
tatcttgatt attggggcca aggcaccctg gtgacggtta gctcagcgtc gaccaaaggt      360
ccaagcgtgt ttccgctggc tccgagcagc aaaagcacca gcggcggcac ggctgccctg      420
ggctgcctgg ttaaagatta tttcccggaa ccagtcaccg tgagctggaa cagcggggcg      480
ctgaccagcg gcgtgcatac ctttccggcg gtgctgcaaa gcagcggcct gtatagcctg      540
agcagcgttg tgaccgtgcc gagcagcagc ttaggcactc agacctatat ttgcaacgtg      600
aaccataaac cgagcaacac caaagtggat aaaaaagtgg aaccgaaaag c              651
```

<210> SEQ ID NO 290
<211> LENGTH: 687

<212> TYPE: DNA
<213> ORGANISM: Homo sapiens

<400> SEQUENCE: 290

| | | | | | |
|---|---|---|---|---|---|
| caggtgcaat | tggttcagtc | tggcgcggaa | gtgaaaaaac | cgggcagcag | cgtgaaagtg | 60 |
| agctgcaaag | cctccggagg | cacttttagc | agctatgcga | ttagctgggt | gcgccaagcc | 120 |
| cctgggcagg | gtctcgagtg | gatgggcggc | attattccga | tttttggcac | ggcgaactac | 180 |
| gcgcagaagt | ttcagggccg | ggtgaccatt | accgcggatg | aaagcaccag | caccgcgtat | 240 |
| atggaactga | gcagcctgcg | tagcgaagat | acggccgtgt | attattgcgc | gcgttatatt | 300 |
| ggttatacta | atgttatgga | tattcgtcct | ggttttttatc | ttgattattg | gggccaaggc | 360 |
| accctggtga | cggttagctc | agcgtcgacc | aaaggtccaa | gcgtgtttcc | gctggctccg | 420 |
| agcagcaaaa | gcaccagcgg | cggcacggct | gccctgggct | gcctggttaa | agattatttc | 480 |
| ccggaaccag | tcaccgtgag | ctggaacagc | ggggcgctga | ccagcggcgt | gcataccttt | 540 |
| ccggcggtgc | tgcaaagcag | cggcctgtat | agcctgagca | gcgttgtgac | cgtgccgagc | 600 |
| agcagcttag | gcactcagac | ctatatttgc | aacgtgaacc | ataaaccgag | caacaccaaa | 660 |
| gtggataaaa | aagtggaacc | gaaaagc | | | | 687 |

<210> SEQ ID NO 291
<211> LENGTH: 669
<212> TYPE: DNA
<213> ORGANISM: Homo sapiens

<400> SEQUENCE: 291

| | | | | | |
|---|---|---|---|---|---|
| caggtgcaat | tggttcagag | cggcgcggaa | gtgaaaaaac | cgggcgaaag | cctgaaaatt | 60 |
| agctgcaaag | gttccggata | ttcctttacg | agctattgga | ttggctgggt | gcgccagatg | 120 |
| cctgggaagg | gtctcgagtg | gatgggcatt | atttatccgg | gcgatagcga | tacccgttat | 180 |
| tctccgagct | ttcagggcca | ggtgaccatt | agcgcgcgata | aaagcattag | caccgcgtat | 240 |
| cttcaatgga | gcagcctgaa | agcgagcgat | acggccatgt | attattgcgc | gcgttttcgt | 300 |
| gcttatggtg | atgatttttta | ttttgatgtt | tggggccaag | gcaccctggt | gacggttagc | 360 |
| tcagcgtcga | ccaaaggtcc | aagcgtgttt | ccgctggctc | cgagcagcaa | aagcaccagc | 420 |
| ggcggcacgg | ctgccctggg | ctgcctggtt | aaagattatt | tcccggaacc | agtcaccgtg | 480 |
| agctggaaca | gcggggcgct | gaccagcggc | gtgcatacct | ttccggcggt | gctgcaaagc | 540 |
| agcggcctgt | atagcctgag | cagcgttgtg | accgtgccga | gcagcagctt | aggcactcag | 600 |
| acctatatttt | gcaacgtgaa | ccataaaccg | agcaacacca | aagtggataa | aaagtggaa | 660 |
| ccgaaaagc | | | | | | 669 |

<210> SEQ ID NO 292
<211> LENGTH: 678
<212> TYPE: DNA
<213> ORGANISM: Homo sapiens

<400> SEQUENCE: 292

| | | | | | |
|---|---|---|---|---|---|
| caggtgcaat | tggttcagag | cggcgcggaa | gtgaaaaaac | cgggcgcgag | cgtgaaagtg | 60 |
| agctgcaaag | cctccggata | tacctttacc | agctattata | tgcactgggt | ccgccaagcc | 120 |
| cctgggcagg | gtctcgagtg | gatgggctgg | attaacccga | atagcggcgg | cacgaactac | 180 |
| gcgcagaagt | ttcagggccg | ggtgaccatg | accgtgata | ccagcattag | caccgcgtat | 240 |
| atggaactga | gcagcctgcg | tagcgaagat | acggccgtgt | attattgcgc | gcgtattatg | 300 |

```
tggtctgatt atggtcagct tgttaagggt ggtgatattt ggggccaagg caccctggtg    360
acggttagct cagcgtcgac caaaggtcca agcgtgtttc cgctggctcc gagcagcaaa    420
agcaccagcg gcggcacggc tgccctgggc tgcctggtta agattatttt cccggaacca    480
gtcaccgtga gctggaacag cggggcgctg accagcggcg tgcataccttt ccggcggtg    540 ctgcaaagca gcggcctgta tagcctgagc agcgttgtga ccgtgccgag cagcagctta    600
ggcactcaga cctatatttg caacgtgaac cataaaccga gcaacaccaa agtggataaa    660
aaagtggaac cgaaaagc                                                  678

<210> SEQ ID NO 293
<211> LENGTH: 666
<212> TYPE: DNA
<213> ORGANISM: Homo sapiens

<400> SEQUENCE: 293
caggtgcaat tggttcagag cggcgcggaa gtgaaaaaac cgggcgaaag cctgaaaatt     60
agctgcaaag gttccggata ttcctttacg agctattgga ttggctgggt cgccagatg    120 cctgggaagg gtctcgagtg gatgggcatt atttatccgg gcgatagcga tacccgttat   180
tctccgagct ttcagggcca ggtgaccatt agcgcggata aaagcattag caccgcgtat   240
cttcaatgga gcagcctgaa agcgagcgat acggccatgt attattgcgc gcgttattat   300
gttactgata ctgcttattt tgattattgg ggccaaggca ccctggtgac ggttagctca   360
gcgtcgacca aggtccaag cgtgtttccg ctggctccga gcagcaaaag caccagcggc   420
ggcacggctg ccctgggctg cctggttaaa gattatttcc cggaaccagt caccgtgagc   480
tggaacagcg gggcgctgac cagcggcgtg catacctttc ggcggtgct gcaaagcagc   540 ggcctgtata gcctgagcag cgttgtgacc gtgccgagca gcagcttagg cactcagacc   600
tatatttgca acgtgaacca taaaccgagc aacaccaaag tggataaaaa agtggaaccg   660
aaaagc                                                              666

<210> SEQ ID NO 294
<211> LENGTH: 666
<212> TYPE: DNA
<213> ORGANISM: Homo sapiens

<400> SEQUENCE: 294
caggtgcaat tggttcagag cggcgcggaa gtgaaaaaac cgggcgaaag cctgaaaatt     60
agctgcaaag gttccggata ttcctttacg agctattgga ttggctgggt cgccagatg    120 cctgggaagg gtctcgagtg gatgggcatt atttatccgg gcgatagcga tacccgttat   180
tctccgagct ttcagggcca ggtgaccatt agcgcggata aaagcattag caccgcgtat   240
cttcaatgga gcagcctgaa agcgagcgat acggccatgt attattgcgc gcgtcatgat   300
tttgatggtt ctattttat ggattttggg gccaaggca ccctggtgac ggttagctca    360
gcgtcgacca aggtccaag cgtgtttccg ctggctccga gcagcaaaag caccagcggc   420
ggcacggctg ccctgggctg cctggttaaa gattatttcc cggaaccagt caccgtgagc   480
tggaacagcg gggcgctgac cagcggcgtg catacctttc ggcggtgct gcaaagcagc   540 ggcctgtata gcctgagcag cgttgtgacc gtgccgagca gcagcttagg cactcagacc   600
tatatttgca acgtgaacca taaaccgagc aacaccaaag tggataaaaa agtggaaccg   660
aaaagc                                                              666
```

<210> SEQ ID NO 295
<211> LENGTH: 669
<212> TYPE: DNA
<213> ORGANISM: Homo sapiens

<400> SEQUENCE: 295

| | | | | | |
|---|---|---|---|---|---|
| caggtgcaat | tggttcagag | cggcgcggaa | gtgaaaaaac | cgggcgaaag | cctgaaaatt | 60 |
| agctgcaaag | gttccggata | ttcctttacg | agctattgga | ttggctgggt | gcgccagatg | 120 |
| cctgggaagg | gtctcgagtg | gatgggcatt | atttatccgg | gcgatagcga | tacccgttat | 180 |
| tctccgagct | ttcagggcca | ggtgaccatt | agcgcggata | aaagcattag | caccgcgtat | 240 |
| cttcaatgga | gcagcctgaa | agcgagcgat | acggccatgt | attattgcgc | gcgttatgct | 300 |
| ggtcatcagt | atgagttttt | ttttgatttt | tggggccaag | gcaccctggt | gacggttagc | 360 |
| tcagcgtcga | ccaaaggtcc | aagcgtgttt | ccgctggctc | cgagcagcaa | aagcaccagc | 420 |
| ggcggcacgg | ctgccctggg | ctgcctggtt | aaagattatt | tcccggaacc | agtcaccgtg | 480 |
| agctggaaca | gcggggcgct | gaccagcggc | gtgcatacct | ttccggcggt | gctgcaaagc | 540 |
| agcggcctgt | atagcctgag | cagcgttgtg | accgtgccga | gcagcagctt | aggcactcag | 600 |
| acctatattt | gcaacgtgaa | ccataaaccg | agcaacacca | agtggataaa | aaagtggaa | 660 |
| ccgaaaagc | | | | | | 669 |

<210> SEQ ID NO 296
<211> LENGTH: 614
<212> TYPE: DNA
<213> ORGANISM: Homo sapiens

<400> SEQUENCE: 296

| | | | | | |
|---|---|---|---|---|---|
| tgaaaattag | ctgcaaaggt | tccggatatt | cctttacgag | ctattggatt | ggctgggtgc | 60 |
| gccagatgcc | tgggaagggt | ctcgagtgga | tgggcattat | ttatccgggc | gatagcgata | 120 |
| cccgttattc | tccgagcttt | cagggccagg | tgaccattag | cgcggataaa | agcattagca | 180 |
| ccgcgtatct | tcaatggagc | agcctgaaag | cgagcgatac | ggccatgtat | tattgcgcgc | 240 |
| gtctttatgc | tgatgctgat | atttattttg | attattgggg | ccaaggcacc | ctggtgacgg | 300 |
| ttagctcagc | gtcgaccaaa | ggtccaagcg | tgtttccgct | ggctccgagc | agcaaaagca | 360 |
| ccagcggcgg | cacggctgcc | ctgggctgcc | tggttaaaga | ttatttcccg | gaaccagtca | 420 |
| ccgtgagctg | gaacagcggg | gcgctgacca | gcggcgtgca | tacctttccg | gcggtgctgc | 480 |
| aaagcagcgg | cctgtatagc | ctgagcagcg | ttgtgaccgt | gccgagcagc | agcttaggca | 540 |
| ctcagaccta | tatttgcaac | gtgaaccata | aaccgagcaa | caccaaagtg | gataaaaaag | 600 |
| tggaaccgaa | aagc | | | | | 614 |

<210> SEQ ID NO 297
<211> LENGTH: 660
<212> TYPE: DNA
<213> ORGANISM: Homo sapiens

<400> SEQUENCE: 297

| | | | | | |
|---|---|---|---|---|---|
| caggtgcaat | tggttcagtc | tggcgcggaa | gtgaaaaaac | cgggcagcag | cgtgaaagtg | 60 |
| agctgcaaag | cctccggagg | cacttttagc | agctatgcga | ttagctgggt | gcgccaagcc | 120 |
| cctgggcagg | gtctcgagtg | gatgggcggc | attattccga | ttttggcac | ggcgaactac | 180 |
| gcgcagaagt | tcagggccg | ggtgaccatt | accgcggatg | aaagcaccag | caccgcgtat | 240 |
| atggaactga | gcagcctgcg | tagcgaagat | acggccgtgt | attattgcgc | gcgtactaag | 300 |

```
tatgttggtt ctgaggatgt ttggggccaa ggcaccctgg tgacggttag ctcagcgtcg      360
accaaaggtc caagcgtgtt ccgctggct ccgagcagca aaagcaccag cggcggcacg      420
gctgccctgg gctgcctggt taaagattat ttccccggaac cagtcaccgt gagctggaac    480
agcggggcgc tgaccagcgg cgtgcatacc tttccggcgg tgctgcaaag cagcggcctg    540
tatagcctga gcagcgttgt gaccgtgccg agcagcagct taggcactca gacctatatt    600
tgcaacgtga accataaacc gagcaacacc aaagtggata aaaagtgga accgaaaagc     660

<210> SEQ ID NO 298
<211> LENGTH: 660
<212> TYPE: DNA
<213> ORGANISM: Homo sapiens

<400> SEQUENCE: 298
caggtgcaat tggttcagag cggcgcggaa gtgaaaaaac cgggcgaaag cctgaaaatt     60
agctgcaaag gttccggata ttcctttacg agctattgga ttggctgggt gcgccagatg   120
cctgggaagg gtctcgagtg gatgggcatt atttatccgg gcgatagcga tacccgttat    180
tctccgagct ttcagggcca ggtgaccatt agcgcgcgata aaagcattag caccgcgtat  240
cttcaatgga gcagcctgaa agcgagcgat acggccatgt attattgcgc gcgttatcgt   300
tatcctcata tgtttgattt ttggggccaa ggcaccctgg tgacggttag ctcagcgtcg    360
accaaaggtc caagcgtgtt ccgctggct ccgagcagca aaagcaccag cggcggcacg      420
gctgccctgg gctgcctggt taaagattat ttccccggaac cagtcaccgt gagctggaac    480
agcggggcgc tgaccagcgg cgtgcatacc tttccggcgg tgctgcaaag cagcggcctg    540
tatagcctga gcagcgttgt gaccgtgccg agcagcagct taggcactca gacctatatt    600
tgcaacgtga accataaacc gagcaacacc aaagtggata aaaagtgga accgaaaagc     660

<210> SEQ ID NO 299
<211> LENGTH: 666
<212> TYPE: DNA
<213> ORGANISM: Homo sapiens

<400> SEQUENCE: 299
caggtgcaat tggttcagag cggcgcggaa gtgaaaaaac cgggcgaaag cctgaaaatt     60
agctgcaaag gttccggata ttcctttacg agctattgga ttggctgggt gcgccagatg   120
cctgggaagg gtctcgagtg gatgggcatt atttatccgg gcgatagcga tacccgttat    180
tctccgagct ttcagggcca ggtgaccatt agcgcgcgata aaagcattag caccgcgtat  240
cttcaatgga gcagcctgaa agcgagcgat acggccatgt attattgcgc gcgtcttttt   300
gctggtcttg agctttattt tgattattgg ggccaaggca ccctggtgac ggttagctca    360
gcgtcgacca aaggtccaag cgtgtttccg ctggctccga gcagcaaaag caccagcggc    420
ggcacggctg ccctgggctg cctggttaaa gattatttcc cggaaccagt caccgtgagc    480
tggaacagcg gggcgctgac cagcggcgtg catacctttc cggcggtgct gcaaagcagc    540
ggcctgtata gcctgagcag cgttgtgacc gtgccgagca gcagcttagg cactcagacc    600
tatatttgca acgtgaacca taaaccgagc aacaccaaag tggataaaaa agtggaaccg   660
aaaagc                                                               666

<210> SEQ ID NO 300
<211> LENGTH: 657
<212> TYPE: DNA
<213> ORGANISM: Homo sapiens
```

```
<400> SEQUENCE: 300
caggtgcaat tggtggaaag cggcggcggc ctggtgcaac cgggcggcag cctgcgtctg    60
agctgcgcgg cctccggatt tacctttagc agctatgcga tgagctgggt gcgccaagcc   120
cctgggaagg gtctcgagtg ggtgagcgcg attagcggta gcggcggcag cacctattat   180
gcggatagcg tgaaaggccg ttttaccatt tcacgtgata attcgaaaaa caccctgtat   240
ctgcaaatga acagcctgcg tgcggaagat acggccgtgt attattgcgc gcgtggtggt   300
ttttttaata tggattattg ggccaaggca cccctggtga cggttagctc agcgtcgacc   360
aaaggtccaa gcgtgtttcc gctggctccg agcagcaaaa gcaccagcgg cggcacggct   420
gccctgggct gcctggttaa agattatttc ccggaaccag tcaccgtgag ctggaacagc   480
ggggcgctga ccagcggcgt gcataccttt ccggcggtgc tgcaaagcag cggcctgtat   540
agcctgagca gcgttgtgac cgtgccgagc agcagcttag gcactcagac ctatatttgc   600
aacgtgaacc ataaaccgag caacaccaaa gtggataaaa agtggaacc gaaaagc      657

<210> SEQ ID NO 301
<211> LENGTH: 663
<212> TYPE: DNA
<213> ORGANISM: Homo sapiens

<400> SEQUENCE: 301
caggtgcaat tggttcagtc tggcgcggaa gtgaaaaaac cgggcagcag cgtgaaagtg    60
agctgcaaag cctccggagg cacttttagc agctatgcga ttagctgggt gcgccaagcc   120
cctgggcagg gtctcgagtg gatgggcggc attattccga tttttggcac ggcgaactac   180
gcgcagaagt ttcagggccg ggtgaccatt accgcggatg aaagcaccag caccgcgtat   240
atggaactga gcagcctgcg tagcgaagat acggccgtgt attattgcgc gcgtggttat   300
attccttatc atcttttga ttattgggc caaggcaccc tggtgacggt tagctcagcg   360
tcgaccaaag gtccaagcgt gtttccgctg gctccgagca gcaaaagcac cagcggcggc   420
acggctgccc tgggctgcct ggttaaagat tatttcccgg aaccagtcac cgtgagctgg   480
aacagcgggg cgctgaccag cggcgtgcat acctttccgg cggtgctgca aagcagcggc   540
ctgtatagcc tgagcagcgt tgtgaccgtg ccgagcagca gcttaggcac tcagacctat   600
atttgcaacg tgaaccataa accgagcaac accaaagtgg ataaaaagt ggaaccgaaa   660 agc                                                                 663

<210> SEQ ID NO 302
<211> LENGTH: 669
<212> TYPE: DNA
<213> ORGANISM: Homo sapiens

<400> SEQUENCE: 302
caggtgcaat tggttcagag cggcgcggaa gtgaaaaaac cgggcgaaag cctgaaaatt    60
agctgcaaag gttccggata ttcctttacg agctattgga ttggctgggt gcgccagatg   120
cctgggaagg gtctcgagtg gatgggcatt atttatccgg gcgatagcga tacccgttat   180
tctccgagct ttcagggcca ggtgaccatt agcgcggata aaagcattag caccgcgtat   240
cttcaatgga gcagcctgaa agcgagcgat acggccatgt attattgcgc gcgttattat   300
ggttttgagt atgatcttct ttttgataat tggggccaag gcaccctggt gacggttagc   360
tcagcgtcga ccaaaggtcc aagcgtgttt ccgctggctc cgagcagcaa aagcaccagc   420
```

```
ggcggcacgg ctgccctggg ctgcctggtt aaagattatt tcccggaacc agtcaccgtg      480
agctggaaca gcgggcgct gaccagcggc gtgcatacct ttccggcggt gctgcaaagc        540
agcggcctgt atagcctgag cagcgttgtg accgtgccga gcagcagctt aggcactcag      600
acctatattt gcaacgtgaa ccataaaccg agcaacacca agtggataaa aaagtggaa       660 ccgaaaagc                                                              669
```

<210> SEQ ID NO 303
<211> LENGTH: 657
<212> TYPE: DNA
<213> ORGANISM: Homo sapiens

<400> SEQUENCE: 303

```
caggtgcaat tggttcagtc tggcgcggaa gtgaaaaaac cgggcagcag cgtgaaagtg       60
agctgcaaag cctccggagg cacttttagc agctatgcga ttagctgggt gcgccaagcc      120
cctgggcagg gtctcgagtg gatgggctgg attaacccga atagcggcgg cacgaactac      180
gcgcagaagt tcagggccg ggtgaccatg acccgtgata ccagcattag caccgcgtat       240
atggaactga gcagcctgcg tagcgaagat acggccgtgt attattgcgc gcgtattact      300
tatattggtt atgatttttg gggccaaggc accctggtga cggttagctc agcgtcgacc      360
aaaggtccaa gcgtgtttcc gctggctccg agcagcaaaa gcaccagcgg cggcacggct      420
gccctgggct gcctggttaa agattatttc ccggaaccag tcaccgtgag ctggaacagc      480
ggggcgctga ccagcggcgt gcatacctt ccggcggtgc tgcaaagcag cggcctgtat      540
agcctgagca gcgttgtgac cgtgccgagc agcagcttag gcactcagac ctatatttgc     600
aacgtgaacc ataaaccgag caacaccaaa gtggataaaa agtggaaccc gaaaagc         657
```

<210> SEQ ID NO 304
<211> LENGTH: 654
<212> TYPE: DNA
<213> ORGANISM: Homo sapiens

<400> SEQUENCE: 304

```
caggtgcaat tggttcagtc tggcgcggaa gtgaaaaaac cgggcagcag cgtgaaagtg       60
agctgcaaag cctccggagg cacttttagc agctatgcga ttagctgggt gcgccaagcc      120
cctgggcagg gtctcgagtg gatgggcggc attattccga tttttggcac ggcgaactac      180
gcgcagaagt tcagggccg ggtgaccatt accgcggatg aaagcaccag caccgcgtat       240
atggaactga gcagcctgcg tagcgaagat acggccgtgt attattgcgc gcgtcaggag      300
tggtatatgg attattgggg ccaaggcacc ctggtgacgg ttagctcagc gtcgaccaaa      360
ggtccaagcg tgtttccgct ggctccgagc agcaaaagca ccagcggcgg cacggctgcc      420
ctgggctgcc tggttaaaga ttatttcccg gaaccagtca ccgtgagctg gaacagcggg      480
gcgctgacca gcgcgtgca tacctttccg gcggtgctgc aaagcagcgg cctgtatagc       540
ctgagcagcg ttgtgaccgt gccgagcagc agcttaggca ctcagaccta tatttgcaac      600
gtgaaccata aaccgagcaa caccaaagtg gataaaaaag tggaaccgaa aagc            654
```

<210> SEQ ID NO 305
<211> LENGTH: 666
<212> TYPE: DNA
<213> ORGANISM: Homo sapiens

<400> SEQUENCE: 305

```
caggtgcaat tggttcagag cggcgcggaa gtgaaaaaac cgggcgaaag cctgaaaatt       60
```

```
agctgcaaag gttccggata ttcctttacg agctattgga ttggctgggt gcgccagatg    120
cctgggaagg gtctcgagtg gatgggcatt atttatccgg gcgatagcga tacccgttat    180
tctccgagct ttcagggcca ggtgaccatt agcgcggata aaagcattag caccgcgtat    240
cttcaatgga gcagcctgaa agcgagcgat acggccatgt attattgcgc gcgtctttat    300
cctgaggatc ttatttattt tgattattgg ggccaaggca ccctggtgac ggttagctca    360
gcgtcgacca aggtccaag cgtgtttccg ctggctccga gcagcaaaag caccagcggc    420
ggcacggctg ccctgggctg cctggttaaa gattatttcc cggaaccagt caccgtgagc    480
tggaacagcg gggcgctgac cagcggcgtg catacctttc cggcggtgct gcaaagcagc    540
ggcctgtata gcctgagcag cgttgtgacc gtgccgagca gcagcttagg cactcagacc    600
tatatttgca acgtgaacca taaaccgagc aacaccaaag tggataaaaa agtggaaccg    660
aaaagc                                                               666

<210> SEQ ID NO 306
<211> LENGTH: 687
<212> TYPE: DNA
<213> ORGANISM: Homo sapiens

<400> SEQUENCE: 306
caggtgcaat tgcaacagtc tggtccgggc ctggtgaaac cgagccaaac cctgagcctg     60
acctgtgcga tttccggaga tagcgtgagc agcaacagcg cggcgtggaa ctggattcgc    120
cagtctcctg ggcgtggcct cgagtggctg ggccgtacct attatcgtag caaatggtat    180
aacgattatg cggtgagcgt gaaaagccgg attaccatca acccggatac ttcgaaaaac    240
cagtttagcc tgcaactgaa cagcgtgacc ccggaagata cggccgtgta ttattgcgcg    300
cgttggatga ctcctcctgg tcattattat ggttatactt ttgatgtttg gggccaaggc    360
accctggtga cggttagctc agcgtcgacc aaaggtccaa gcgtgtttcc gctggctccg    420
agcagcaaaa gcaccagcgg cggcacggct gccctgggct gcctggttaa agattatttc    480
ccggaaccag tcaccgtgag ctggaacagc ggggcgctga ccagcggcgt gcatacctttt   540 ccggcggtgc tgcaaagcag cggcctgtat agcctgagca gcgttgtgac cgtgccgagc    600
agcagcttag gcactcagac ctatatttgc aacgtgaacc ataaaccgag caacaccaaa    660
gtggataaaa aagtggaacc gaaaagc                                        687

<210> SEQ ID NO 307
<211> LENGTH: 669
<212> TYPE: DNA
<213> ORGANISM: Homo sapiens

<400> SEQUENCE: 307
caggtgcaat tggttcagag cggcgcggaa gtgaaaaaac cgggcgaaag cctgaaaatt     60
agctgcaaag gttccggata ttcctttacg agctattgga ttggctgggt gcgccagatg    120
cctgggaagg gtctcgagtg gatgggcatt atttatccgg gcgatagcga tacccgttat    180
tctccgagct ttcagggcca ggtgaccatt agcgcggata aaagcattag caccgcgtat    240
cttcaatgga gcagcctgaa agcgagcgat acggccatgt attattgcgc gcgtcttcgt    300
gttcatgatt atgctatgta ttttgatctt tggggccaag gcaccctggt gacggttagc    360
tcagcgtcga ccaaaggtcc aagcgtgttt ccgctggctc cgagcagcaa agcaccagc    420 ggcggcacgg ctgccctggg ctgcctggtt aaagattatt tcccggaacc agtcaccgtg    480
```

```
agctggaaca gcggggcgct gaccagcggc gtgcatacct ttccggcggt gctgcaaagc        540
agcggcctgt atagcctgag cagcgttgtg accgtgccga gcagcagctt aggcactcag        600
acctatattt gcaacgtgaa ccataaaccg agcaacacca agtggataa aaaagtggaa        660 ccgaaaagc                                                                669
```

<210> SEQ ID NO 308
<211> LENGTH: 672
<212> TYPE: DNA
<213> ORGANISM: Homo sapiens

<400> SEQUENCE: 308

```
caggtgcaat tggttcagag cggcgcggaa gtgaaaaaac cgggcgaaag cctgaaaatt        60
agctgcaaag gttccggata ttcctttacg agctattgga ttggctgggt gcgccagatg        120
cctgggaagg gtctcgagtg gatgggcatt atttatccgg gcgatagcga tacccgttat        180
tctccgagct ttcagggcca ggtgaccatt agcgcggata aaagcattag caccgcgtat        240
cttcaatgga gcagcctgaa agcgagcgat acggccatgt attattgcgc gcgttttgtt        300
tcttataatg gttctgttcc ttattttgat tattggggcc aaggcaccct ggtgacggtt        360
agctcagcgt cgaccaaagg tccaagcgtg tttccgctgg ctccgagcag caaaagcacc        420
agcggcggca cggctgccct gggctgcctg gttaaagatt atttcccgga accagtcacc        480
gtgagctgga acagcggggc gctgaccagc ggcgtgcata cctttccggc ggtgctgcaa        540
agcagcggcc tgtatagcct gagcagcgtt gtgaccgtgc cgagcagcag cttaggcact        600
cagacctata tttgcaacgt gaaccataaa ccgagcaaca ccaaagtgga taaaaaagtg        660
gaaccgaaaa gc                                                            672
```

<210> SEQ ID NO 309
<211> LENGTH: 666
<212> TYPE: DNA
<213> ORGANISM: Homo sapiens

<400> SEQUENCE: 309

```
caggtgcaat tggttcagag cggcgcggaa gtgaaaaaac cgggcgaaag cctgaaaatt        60
agctgcaaag gttccggata ttcctttacg agctattgga ttggctgggt gcgccagatg        120
cctgggaagg gtctcgagtg gatgggcatt atttatccgg gcgatagcga tacccgttat        180
tctccgagct ttcagggcca ggtgaccatt agcgcggata aaagcattag caccgcgtat        240
cttcaatgga gcagcctgaa agcgagcgat acggccatgt attattgcgc gcgtattatt        300
ggtgattatg ttatttttttt tgatgtttgg ggccaaggca ccctggtgac ggttagctca        360
gcgtcgacca aaggtccaag cgtgtttccg ctggctccga gcagcaaaag caccagcggc        420
ggcacggctg ccctgggctg cctggttaaa gattatttcc cggaaccagt caccgtgagc        480
tggaacagcg gggcgctgac cagcggcgtg catacctttc cggcggtgct gcaaagcagc        540
ggcctgtata gcctgagcag cgttgtgacc gtgccgagca gcagcttagg cactcagacc        600
tatatttgca acgtgaacca taaaccgagc aacaccaaag tggataaaaa agtggaaccg        660
aaaagc                                                                   666
```

<210> SEQ ID NO 310
<211> LENGTH: 609
<212> TYPE: DNA
<213> ORGANISM: Homo sapiens

<400> SEQUENCE: 310

```
attagctgca aaggttccgg atattccttt acgagctatt ggattggctg ggtgcgccag    60
atgcctggga agggtctcga gtggatgggc attatttatc cgggcgatag cgatacccgt   120
tattctccga gctttcaggg ccaggtgacc attagcgcgg ataaaagcat tagcaccgcg   180
tatcttcaat ggagcagcct gaaagcgagc gatacggcca tgtattattg cgcgcgtctt   240
tttacttatc ctttctttta ttttgatgtt tggggccaag caccctggt gacggttagc    300 tcagcgtcga ccaaaggtcc aagcgtgttt ccgctggctc cgagcagcaa agcaccagc   360 ggcggcacgg ctgccctggg ctgcctggtt aaagattatt tcccggaacc agtcaccgtg   420
agctggaaca gcggggcgct gaccagcggc gtgcatacct ttccggcggt gctgcaaagc   480
agcggcctgt atagcctgag cagcgttgtg accgtgccga gcagcagctt aggcactcag   540
acctatattt gcaacgtgaa ccataaaccg agcaacacca agtggataa aaaagtggaa    600 ccgaaaagc                                                           609
```

<210> SEQ ID NO 311
<211> LENGTH: 666
<212> TYPE: DNA
<213> ORGANISM: Homo sapiens

<400> SEQUENCE: 311

```
caggtgcaat tggttcagag cggcgcggaa gtgaaaaaac cgggcgaaag cctgaaaatt    60
agctgcaaag gttccggata ttcctttacg agctattgga ttggctgggt gcgccagatg   120
cctgggaagg gtctcgagtg gatgggcatt atttatccgg gcgatagcga tacccgttat   180
tctccgagct ttcagggcca ggtgaccatt agcgcggata aaagcattag caccgcgtat   240
cttcaatgga gcagcctgaa agcgagcgat acggccatgt attattgcgc gcgtattctt   300
actggtcacg ttcttctttt tgattattgg ggccaaggca ccctggtgac ggttagctca   360
gcgtcgacca aaggtccaag cgtgtttccg ctggctccga gcagcaaaag caccagcggc   420
ggcacggctg ccctgggctg cctggttaaa gattatttcc cggaaccagt caccgtgagc   480
tggaacagcg gggcgctgac cagcggcgtg catacctttc cggcggtgct gcaaagcagc   540
ggcctgtata gcctgagcag cgttgtgacc gtgccgagca gcagcttagg cactcagacc   600
tatatttgca acgtgaacca taaaccgagc aacaccaaag tggataaaaa agtggaaccg   660
aaaagc                                                              666
```

<210> SEQ ID NO 312
<211> LENGTH: 645
<212> TYPE: DNA
<213> ORGANISM: Homo sapiens

<400> SEQUENCE: 312

```
gatatcgcac tgacccagcc agcttcagtg agcggctcac caggtcagag cattaccatc    60
tcgtgtacgg gtactagcag cgatgtgggc ggctataact atgtgagctg gtaccagcag   120
catcccggga aggcgccgaa actgatgatt tatgatgtga gcaaccgtcc ctcaggcgtg   180
agcaaccgtt ttagcggatc caaaagcggc aacaccgcga gcctgaccat tagcggcctg   240
caagcggaag acgaagcgga ttattattgc cagagctatg actatcagca gtttactgtg   300
tttggcggcg gcacgaagtt aaccgttctt ggccagccga agccgcacc gagtgtgacg   360 ctgtttccgc cgagcagcga agaattgcag gcgaacaaag cgaccctggt gtgcctgatt   420 agcgacttttt atccgggagc cgtgacagtg gcctggaagg cagatagcag ccccgtcaag   480
```

```
gcgggagtgg agaccaccac accctccaaa caaagcaaca acaagtacgc ggccagcagc      540
tatctgagcc tgacgcctga gcagtggaag tcccacagaa gctacagctg ccaggtcacg      600
catgagggga gcaccgtgga aaaaaccgtt gcgccgactg aggcc                     645
```

<210> SEQ ID NO 313
<211> LENGTH: 645
<212> TYPE: DNA
<213> ORGANISM: Homo sapiens

<400> SEQUENCE: 313

```
gatatcgcac tgacccagcc agcttcagtg agcggctcac caggtcagag cattaccatc       60
tcgtgtacgg gtactagcag cgatgtgggc ggctataact atgtgagctg gtaccagcag      120
catcccggga aggcgccgaa actgatgatt tatgatgtga gcaaccgtcc ctcaggcgtg      180
agcaaccgtt ttagcggatc caaaagcggc aacaccgcga gcctgaccat tagcggcctg      240
caagcggaag acgaagcgga ttattattgc cagagctatg actttaagac ttatcttgtg      300
tttggcggcg gcacgaagtt aaccgttctt ggccagccga agccgcacc gagtgtgacg       360 ctgtttccgc cgagcagcga agaattgcag gcgaacaaag cgaccctggt gtgcctgatt      420
agcgactttt atccgggagc cgtgacagtg gcctggaagg cagatagcag ccccgtcaag      480
gcgggagtgg agaccaccac accctccaaa caaagcaaca acaagtacgc ggccagcagc      540
tatctgagcc tgacgcctga gcagtggaag tcccacagaa gctacagctg ccaggtcacg      600
catgagggga gcaccgtgga aaaaaccgtt gcgccgactg aggcc                     645
```

<210> SEQ ID NO 314
<211> LENGTH: 645
<212> TYPE: DNA
<213> ORGANISM: Homo sapiens

<400> SEQUENCE: 314

```
gatatcgcac tgacccagcc agcttcagtg agcggctcac caggtcagag cattaccatc       60
tcgtgtacgg gtactagcag cgatgtgggc ggctataact atgtgagctg gtaccagcag      120
catcccggga aggcgccgaa actgatgatt tatgatgtga gcaaccgtcc ctcaggcgtg      180
agcaaccgtt ttagcggatc caaaagcggc aacaccgcga gcctgaccat tagcggcctg      240
caagcggaag acgaagcgga ttattattgc cagagctatg actttcttcg tttttctgtg      300
tttggcggcg gcacgaagtt aaccgttctt ggccagccga agccgcacc gagtgtgacg       360 ctgtttccgc cgagcagcga agaattgcag gcgaacaaag cgaccctggt gtgcctgatt      420
agcgactttt atccgggagc cgtgacagtg gcctggaagg cagatagcag ccccgtcaag      480
gcgggagtgg agaccaccac accctccaaa caaagcaaca acaagtacgc ggccagcagc      540
tatctgagcc tgacgcctga gcagtggaag tcccacagaa gctacagctg ccaggtcacg      600
catgagggga gcaccgtgga aaaaaccgtt gcgccgactg aggcc                     645
```

<210> SEQ ID NO 315
<211> LENGTH: 638
<212> TYPE: DNA
<213> ORGANISM: Homo sapiens

<400> SEQUENCE: 315

```
gatatcgcac tgacccagcc agcttcagtg agcggctcac caggtcagag cattaccatc       60
tcgtgtacgg gtactagcag cgatgtgggc ggctataact atgtgagctg gtaccagcag      120
catcccggga aggcgccgaa actgatgatt tatgatgtga gcaaccgtcc ctcaggcgtg      180
```

```
agcaaccgtt ttagcggatc caaaagcggc aacaccgcga gcctgaccat tagcggcctg    240
caagcggaag acgaagcgga ttattattgc cagagctatg actttattaa tgttattgtg    300
tttggcggcg gcacgaagtt aaccgttctt ggccagccga agccgcacc gagtgtgacg    360 ctgtttccgc cgagcagcga agaattgcag gcgaacaaag cgaccctggt gtgcctgatt    420
agcgactttt atccgggagc cgtgacagtg gcctggaagg cagatagcag ccccgtcaag    480
gcgggagtgg agaccaccac accctccaaa caaagcaaca caagtacgc ggccagcagc    540 tatctgagcc tgacgcctga gcagtggaag tcccacagaa gctacagctg ccaggtcacg    600
catgagggga gcaccgtgga aaaaaccgtt gcgccgac                           638
```

<210> SEQ ID NO 316
<211> LENGTH: 645
<212> TYPE: DNA
<213> ORGANISM: Homo sapiens

<400> SEQUENCE: 316

```
gatatcgcac tgacccagcc agcttcagtg agcggctcac caggtcagag cattaccatc    60
tcgtgtacgg gtactagcag cgatgtgggc ggctataact atgtgagctg gtaccagcag   120
catcccggga aggcgccgaa actgatgatt tatgatgtga gcaaccgtcc ctcaggcgtg   180
agcaaccgtt ttagcggatc caaaagcggc aacaccgcga gcctgaccat tagcggcctg   240
caagcggaag acgaagcgga ttattattgc cagagctatg actttgttcg ttttatggtg   300
tttggcggcg gcacgaagtt aaccgttctt ggccagccga agccgcacc gagtgtgacg   360 ctgtttccgc cgagcagcga agaattgcag gcgaacaaag cgaccctggt gtgcctgatt   420
agcgactttt atccgggagc cgtgacagtg gcctggaagg cagatagcag ccccgtcaag   480
gcgggagtgg agaccaccac accctccaaa caaagcaaca caagtacgc ggccagcagc   540 tatctgagcc tgacgcctga gcagtggaag tcccacagaa gctacagctg ccaggtcacg   600
catgagggga gcaccgtgga aaaaaccgtt gcgccgactg aggcc                   645
```

<210> SEQ ID NO 317
<211> LENGTH: 638
<212> TYPE: DNA
<213> ORGANISM: Homo sapiens

<400> SEQUENCE: 317

```
gatatcgcac tgacccagcc agcttcagtg agcggctcac caggtcagag cattaccatc    60
tcgtgtacgg gtactagcag cgatgtgggc ggctataact atgtgagctg gtaccagcag   120
catcccggga aggcgccgaa actgatgatt tatgatgtga gcaaccgtcc ctcaggcgtg   180
agcaaccgtt ttagcggatc caaaagcggc aacaccgcga gcctgaccat tagcggcctg   240
caagcggaag acgaagcgga ttattattgc cagagctatg acttttataa gtttaatgtg   300
tttggcggcg gcacgaagtt aaccgttctt ggccagccga agccgcacc gagtgtgacg   360 ctgtttccgc cgagcagcga agaattgcag gcgaacaaag cgaccctggt gtgcctgatt   420
agcgactttt atccgggagc cgtgacagtg gcctggaagg cagatagcag ccccgtcaag   480
gcgggagtgg agaccaccac accctccaaa caaagcaaca caagtacgc ggccagcagc   540 tatctgagcc tgacgcctga gcagtggaag tcccacagaa gctacagctg ccaggtcacg   600
catgagggga gcaccgtgga aaaaaccgtt gcgccgac                           638
```

<210> SEQ ID NO 318

<211> LENGTH: 638
<212> TYPE: DNA
<213> ORGANISM: Homo sapiens

<400> SEQUENCE: 318

| | | | | | |
|---|---|---|---|---|---|
| gatatcgcac | tgacccagcc | agcttcagtg | agcggctcac | caggtcagag | cattaccatc | 60 |
| tcgtgtacgg | gtactagcag | cgatgtgggc | ggctataact | atgtgagctg | gtaccagcag | 120 |
| catcccggga | aggcgccgaa | actgatgatt | tatgatgtga | gcaaccgtcc | ctcaggcgtg | 180 |
| agcaaccgtt | ttagcggatc | caaaagcggc | aacaccgcga | gcctgaccat | tagcggcctg | 240 |
| caagcggaag | acgaagcgga | ttattattgc | cagagctatg | actttcgtcg | ttttctgtg | 300 |
| tttggcggcg | gcacgaagtt | aaccgttctt | ggccagccga | agccgcacc | gagtgtgacg | 360 |
| ctgtttccgc | cgagcagcga | agaattgcag | gcgaacaaag | cgaccctggt | gtgcctgatt | 420 |
| agcgactttt | atccgggagc | cgtgacagtg | gcctggaagg | cagatagcag | ccccgtcaag | 480 |
| gcgggagtgg | agaccaccac | accctccaaa | caaagcaaca | caagtacgc | ggccagcagc | 540 |
| tatctgagcc | tgacgcctga | gcagtggaag | tcccacagaa | gctacagctg | ccaggtcacg | 600 |
| catgagggga | gcaccgtgga | aaaaaccgtt | gcgccgac | | | 638 |

<210> SEQ ID NO 319
<211> LENGTH: 642
<212> TYPE: DNA
<213> ORGANISM: Homo sapiens

<400> SEQUENCE: 319

| | | | | | |
|---|---|---|---|---|---|
| gatatcgtgc | tgacccagcc | gccttcagtg | agtggcgcac | caggtcagcg | tgtgaccatc | 60 |
| tcgtgtagcg | gcagcagcag | caacattggc | agcaactatg | tgagctggta | ccagcagttg | 120 |
| cccgggacgg | cgccgaaact | gctgatttat | gataacaacc | agcgtccctc | aggcgtgccg | 180 |
| gatcgtttta | gcggatccaa | aagcggcacc | agcgcgagcc | ttgcgattac | gggcctgcaa | 240 |
| agcgaagacg | aagcggatta | ttattgccag | agccgtgact | ttaatcgtgg | tcctgtgttt | 300 |
| ggcggcggca | cgaagttaac | cgttcttggc | cagccgaaag | ccgcaccgag | tgtgacgctg | 360 |
| tttccgccga | gcagcgaaga | attgcaggcg | aacaaagcga | ccctggtgtg | cctgattagc | 420 |
| gactttatc | cggagccgt | gacagtggcc | tggaaggcag | atagcagccc | cgtcaaggcg | 480 |
| ggagtggaga | ccaccacacc | ctccaaacaa | agcaacaaca | agtacgcggc | cagcagctat | 540 |
| ctgagcctga | cgcctgagca | gtggaagtcc | cacagaagct | acagctgcca | ggtcacgcat | 600 |
| gagggagca | ccgtggaaaa | aaccgttgcg | ccgactgagg | cc | | 642 |

<210> SEQ ID NO 320
<211> LENGTH: 639
<212> TYPE: DNA
<213> ORGANISM: Homo sapiens

<400> SEQUENCE: 320

| | | | | | |
|---|---|---|---|---|---|
| gatatcgtgc | tgacccagcc | gccttcagtg | agtggcgcac | caggtcagcg | tgtgaccatc | 60 |
| tcgtgtagcg | gcagcagcag | caacattggc | agcaactatg | tgagctggta | ccagcagttg | 120 |
| cccgggacgg | cgccgaaact | gctgatttat | gataacaacc | agcgtccctc | aggcgtgccg | 180 |
| gatcgtttta | gcggatccaa | aagcggcacc | agcgcgagcc | ttgcgattac | gggcctgcaa | 240 |
| agcgaagacg | aagcggatta | ttattgccag | agctatgacc | agcgtaagtg | ggtgtttggc | 300 |
| ggcggcacga | agttaaccgt | tcttggccag | ccgaaagccg | caccgagtgt | gacgctgttt | 360 |
| ccgccgagca | gcgaagaatt | gcaggcgaac | aaagcgaccc | tggtgtgcct | gattagcgac | 420 |

```
tttatccgg gagccgtgac agtggcctgg aaggcagata gcagcccgt caaggcggga    480 gtggagacca ccacaccctc caaacaaagc aacaacaagt acgcggccag cagctatctg    540
agcctgacgc ctgagcagtg gaagtcccac agaagctaca gctgccaggt cacgcatgag    600
gggagcaccg tggaaaaaac cgttgcgccg actgaggcc                           639
```

<210> SEQ ID NO 321
<211> LENGTH: 672
<212> TYPE: DNA
<213> ORGANISM: Homo sapiens

<400> SEQUENCE: 321

```
gatatcgtgc tgacccagag cccggcgacc ctgagcctgt ctccgggcga acgtgcgacc     60
ctgagctgca gagcgagcca gagcgtgagc agcagctatc tggcgtggta ccagcagaaa    120
ccaggtcaag caccgcgtct attaatttat ggcgcgagca gccgtgcaac tggggtcccg    180
gcgcgtttta gcggctctgg atccggcacg gattttaccc tgaccattag cagcctggaa    240
cctgaagact ttgcgactta ttattgccag cagctttatg gtacttctgt tacctttggc    300
cagggtacga agttgaaat  taaacgtacg gtggctgctc cgagcgtgtt tattttccg    360 ccgagcgatg aacaactgaa agcggcacg  gcgagcgtgg tgtgcctgct gaacaacttt    420
tatccgcgtg aagcgaaagt tcagtggaaa gtagacaacg cgctgcaaag cggcaacagc    480
caggaaagcg tgaccgaaca ggatagcaaa gatagcacct attctctgag cagcaccctg    540
accctgagca aagcggatta tgaaaaacat aaagtgtatg cgtgcgaagt gacccatcaa    600
ggtctgagca gcccggtgac taaatctttt aatcgtggcg aggcctgata agcatgcgta    660
ggagaaaata aa                                                        672
```

<210> SEQ ID NO 322
<211> LENGTH: 642
<212> TYPE: DNA
<213> ORGANISM: Homo sapiens

<400> SEQUENCE: 322

```
gatatcgtgc tgacccagcc gccttcagtg agtggcgcac aggtcagcg  tgtgaccatc     60 tcgtgtagcg gcagcagcag caacattggc agcaactatg tgagctggta ccagcagttg    120
cccgggacgg cgccgaaact gctgatttat gataacaacc agcgtccctc aggcgtgccg    180 gatcgttta  gcggatccaa aagcggcacc agcgcgagcc ttgcgattac gggcctgcaa    240
agcgaagacg aagcggatta ttattgccag agctatgacg gttttaagac tcatgtgttt    300
ggcggcggca cgaagttaac cgttcttggc cagccgaaag ccgcaccgag tgtgacgctg    360
tttccgccga gcagcgaaga attgcaggcg aacaaagcga ccctggtgtg cctgattagc    420
gacttttatc cgggagccgt gacagtggcc tggaaggcag atagcagccc cgtcaaggcg    480
ggagtggaga ccaccacacc ctccaaacaa agcaacaaca agtacgcggc cagcagctat    540
ctgagcctga cgcctgagca gtggaagtcc cacagaagct acagctgcca ggtcacgcat    600 gagggagcg ccgtggaaaa aaccgttgcg ccgactgagg cc                        642
```

<210> SEQ ID NO 323
<211> LENGTH: 633
<212> TYPE: DNA
<213> ORGANISM: Homo sapiens

<400> SEQUENCE: 323

| gatatcgaac tgacccagcc gccttcagtg agcgttgcac caggtcagac cgcgcgtatc | 60 |
| tcgtgtagcg gcgatgcgct gggcgataaa tacgcgagct ggtaccagca gaaacccggg | 120 |
| caggcgccag ttctggtgat ttatgatgat tctgaccgtc cctcaggcat cccggaacgc | 180 |
| tttagcggat ccaacagcgg caacaccgcg accctgacca ttagcggcac tcaggcggaa | 240 |
| gacgaagcgg attattattg ccagagctat gactattctc ttcttgtgtt tggcggcggc | 300 |
| acgaagttaa ccgttcttgg ccagccgaaa gccgcaccga gtgtgacgct gtttccgccg | 360 |
| agcagcgaag aattgcaggc gaacaaagcg accctggtgt gcctgattag cgacttttat | 420 |
| ccgggagccg tgacagtggc ctggaaggca gatagcagcc ccgtcaaggc gggagtggag | 480 |
| accaccacac cctccaaaca aagcaacaac aagtacgcgg ccagcagcta tctgagcctg | 540 |
| acgcctgagc agtggaagtc ccacagaagc tacagctgcc aggtcacgca tgaggggagc | 600 |
| accgtggaaa aaaccgttgc gccgactgag gcc | 633 |

<210> SEQ ID NO 324
<211> LENGTH: 633
<212> TYPE: DNA
<213> ORGANISM: Homo sapiens

<400> SEQUENCE: 324

| gatatcgaac tgacccagcc gccttcagtg agcgttgcac caggtcagac cgcgcgtatc | 60 |
| tcgtgtagcg gcgatgcgct gggcgataaa tacgcgagct ggtaccagca gaaacccggg | 120 |
| caggcgccag ttctggtgat ttatgatgat tctgaccgtc cctcaggcat cccggaacgc | 180 |
| tttagcggat ccaacagcgg caacaccgcg accctgacca ttagcggcac tcaggcggaa | 240 |
| gacgaagcgg attattattg ccagagctat gactttaatt ttcatgtgtt tggcggcggc | 300 |
| acgaagttaa ccgttcttgg ccagccgaaa gccgcaccga gtgtgacgct gtttccgccg | 360 |
| agcagcgaag aattgcaggc gaacaaagcg accctggtgt gcctgattag cgacttttat | 420 |
| ccgggagccg tgacagtggc ctggaaggca gatagcagcc ccgtcaaggc gggagtggag | 480 |
| accaccacac cctccaaaca aagcaacaac aagtacgcgg ccagcagcta tctgagcctg | 540 |
| acgcctgagc agtggaagtc ccacagaagc tacagctgcc aggtcacgca tgaggggagc | 600 |
| accgtggaaa aaaccgttgc gccgactgag gcc | 633 |

<210> SEQ ID NO 325
<211> LENGTH: 648
<212> TYPE: DNA
<213> ORGANISM: Homo sapiens

<400> SEQUENCE: 325

| gatatcgcac tgacccagcc agcttcagtg agcggctcac caggtcagag cattaccatc | 60 |
| tcgtgtacgg gtactagcag cgatgtgggc ggctataact atgtgagctg gtaccagcag | 120 |
| catcccggga aggcgccgaa actgatgatt tatgatgtga caaccgtcc ctcaggcgtg | 180 |
| agcaaccgtt ttagcggatc caaaagcggc aacaccgcga gcctgaccat tagcggcctg | 240 |
| caagcggaag acgaagcgga ttattattgc cagagctatg acatgattgc tcgttatcct | 300 |
| gtgtttggcg gcggcacgaa gttaaccgtt cttggccagc cgaaagccgc accgagtgtg | 360 |
| acgctgtttc cgccgagcag cgaagaattg caggcgaaca aagcgaccct ggtgtgcctg | 420 |
| attagcgact ttatccgggg agccgtgaca gtggcctgga aggcagatag cagccccgtc | 480 |
| aaggcgggag tggagaccac cacaccctcc aaacaaagca acaacaagta cgcggccagc | 540 |
| agctatctga gcctgacgcc tgagcagtgg aagtcccaca gaagctacag ctgccaggtc | 600 |

-continued acgcatgagg ggagcaccgt ggaaaaaacc gttgcgccga ctgaggcc        648

<210> SEQ ID NO 326
<211> LENGTH: 639
<212> TYPE: DNA
<213> ORGANISM: Homo sapiens

<400> SEQUENCE: 326
gatatcgaac tgacccagcc gccttcagtg agcgttgcac caggtcagac cgcgcgtatc        60
tcgtgtagcg gcgatgcgct gggcgataaa tacgcgagct ggtaccagca gaaacccggg       120
caggcgccag ttctggtgat ttatgatgat tctgaccgtc cctcaggcat cccggaacgc       180
tttagcggat ccaacagcgg caacaccgcg accctgacca ttagcggcac tcaggcggaa       240
gacgaagcgg attattattg ccagagctgg gacattcatc cttttgatgt tgtgtttggc       300
ggcggcacga agttaaccgt tcttggccag ccgaaagccg caccgagtgt gacgctgttt       360
ccgccgagca gcgaagaatt gcaggcgaac aaagcgaccc tggtgtgcct gattagcgac       420
tttttatccgg gagccgtgac agtggcctgg aaggcagata gcagcccgt caaggcggga       480
gtggagacca ccacaccctc caaacaaagc aacaacaagt acgcggccag cagctatctg       540
agcctgacgc ctgagcagtg gaagtcccac agaagctaca gctgccaggt cacgcatgag       600
gggagcaccg tggaaaaaac cgttgcgccg actgaggcc                             639

<210> SEQ ID NO 327
<211> LENGTH: 639
<212> TYPE: DNA
<213> ORGANISM: Homo sapiens

<400> SEQUENCE: 327
gatatcgtgc tgacccagcc gccttcagtg agtggcgcac caggtcagcg tgtgaccatc        60
tcgtgtagcg gcagcagcag caacattggc agcaactatg tgagctggta ccagcagttg       120
cccgggacgg cgccgaaact gctgatttat gataacaacc agcgtccctc aggcgtgccg       180
gatcgtttta gcggatccaa aagcggcacc agcgcgagcc ttgcgattac gggcctgcaa       240
agcgaagacg aagcggatta ttattgccag agctgggacc ttgagcctta tgtgtttggc       300
ggcggcacga agttaaccgt tcttggccag ccgaaagccg caccgagtgt gacgctgttt       360
ccgccgagca gcgaagaatt gcaggcgaac aaagcgaccc tggtgtgcct gattagcgac       420
tttttatccgg gagccgtgac agtggcctgg aaggcagata gcagcccgt caaggcggga       480
gtggagacca ccacaccctc caaacaaagc aacaacaagt acgcggccag cagctatctg       540
agcctgacgc ctgagcagtg gaagtcccac agaagctaca gctgccaggt cacgcatgag       600
gggagcaccg tggaaaaaac cgttgcgccg actgaggcc                             639

<210> SEQ ID NO 328
<211> LENGTH: 645
<212> TYPE: DNA
<213> ORGANISM: Homo sapiens

<400> SEQUENCE: 328
gatatcgcac tgacccagcc agcttcagtg agcggctcac caggtcagag cattaccatc        60
tcgtgtacgg gtactagcag cgatgtgggc ggctataact atgtgagctg gtaccagcag       120
catcccggga aggcgccgaa actgatgatt tatgatgtga caacgtcc ctcaggcgtg       180
agcaaccgtt ttagcggatc caaaagcggc aacaccgcga gcctgaccat tagcggcctg       240

```
caagcggaag acgaagcgga ttattattgc cagagctatg acgttcttga ttctgaggtg      300
tttggcggcg gcacgaagtt aaccgttctt ggccagccaa agccgcacc gagtgtgacg       360 ctgtttccgc cgagcagcga agaattgcag gcgaacaaag cgaccctggt gtgcctgatt      420
agcgactttt atccgggagc cgtgacagtg gcctggaagg cagatagcag ccccgtcaag     480
gcgggagtgg agaccaccac accctccaaa caaagcaaca acaagtacgc ggccagcagc    540
tatctgagcc tgacgcctga gcagtggaag tcccacagaa gctacagctg ccaggtcacg    600
catgagggga gcaccgtgga aaaaaccgtt gcgccgactg aggcc                     645

<210> SEQ ID NO 329
<211> LENGTH: 648
<212> TYPE: DNA
<213> ORGANISM: Homo sapiens

<400> SEQUENCE: 329
gatatcgcac tgacccagcc agcttcagtg agcggctcac caggtcagag cattaccatc      60
tcgtgtacgg gtactagcag cgatgtgggc ggctataact atgtgagctg gtaccagcag     120
catcccggga aggcgccgaa actgatgatt tatgatgtga gcaaccgtcc ctcaggcgtg     180
agcaaccgtt ttagcggatc caaaagcggc aacaccgcga gcctgaccat tagcggcctg    240
caagcggaag acgaagcgga ttattattgc cagagctatg acccttctca tccttctaag    300
gtgtttggcg gcggcacgaa gttaaccgtt cttggccagc cgaaagccgc accgagtgtg    360
acgctgtttc cgccgagcag cgaagaattg caggcgaaca aagcgaccct ggtgtgcctg    420
attagcgact tttatccggg agccgtgaca gtggcctgga aggcagatag cagccccgtc    480
aaggcgggag tggagaccac cacaccctcc aaacaaagca acaacaagta cgcggccagc    540
agctatctga gcctgacgcc tgagcagtgg aagtcccaca gaagctacag ctgccaggtc    600
acgcatgagg ggagcaccgt ggaaaaaaacc gttgcgccga ctgaggcc                648

<210> SEQ ID NO 330
<211> LENGTH: 642
<212> TYPE: DNA
<213> ORGANISM: Homo sapiens

<400> SEQUENCE: 330
gatatcgcac tgacccagcc agcttcagtg agcggctcac caggtcagag cattaccatc      60
tcgtgtacgg gtactagcag cgatgtgggc ggctataact atgtgagctg gtaccagcag     120
catcccggga aggcgccgaa actgatgatt tatgatgtga gcaaccgtcc ctcaggcgtg     180
agcaaccgtt ttagcggatc caaaagcggc aacaccgcga gcctgaccat tagcggcctg    240
caagcggaag acgaagcgga ttattattgc cagagctatg acgatatgca gtttgtgttt    300
ggcggcggca cgaagttaac cgttcttggc cagccgaaag ccgcaccgag tgtgacgctg    360
tttccgccga gcgcgaaga attgcaggcg aacaaagcga ccctggtgtg cctgattagc    420 gactttttatc cgggagccgt gacagtggcc tggaaggcag atagcagccc cgtcaaggcg    480
ggagtggaga ccaccacacc ctccaaacaa agcaacaaca agtacgcggc cagcagctat    540
ctgagcctga cgcctgagca gtggaagtcc cacagaagct acagctgcca ggtcacgcat    600
gaggggagca ccgtggaaaa aaccgttgcg ccgactgagg cc                       642

<210> SEQ ID NO 331
<211> LENGTH: 645
<212> TYPE: DNA
<213> ORGANISM: Homo sapiens
```

<400> SEQUENCE: 331

```
gatatcgcac tgacccagcc agcttcagtg agcggctcac caggtcagag cattaccatc    60
tcgtgtacgg gtactagcag cgatgtgggc ggctataact atgtgagctg gtaccagcag   120
catcccggga aggcgccgaa actgatgatt tatgatgtga gcaaccgtcc ctcaggcgtg   180
agcaaccgtt ttagcggatc caaaagcggc aacaccgcga gcctgaccat tagcggcctg   240
caagcggaag acgaagcgga ttattattgc cagagctggg acattaatca tgctattgtg   300
tttggcggcg gcacgaagtt aaccgttctt ggccagccga agccgcacc gagtgtgacg    360
ctgtttccgc cgagcagcga agaattgcag gcgaacaaag cgaccctggt gtgcctgatt   420
agcgacttt atccgggagc cgtgacagtg gcctggaagg cagatagcag ccccgtcaag    480
gcgggagtgg agaccaccac accctccaaa caaagcaaca caagtacgc ggccagcagc    540
tatctgagcc tgacgcctga gcagtggaag tcccacagaa gctacagctg ccaggtcacg   600
catgagggga gcaccgtgga aaaaaccgtt gcgccgactg aggcc                   645
```

<210> SEQ ID NO 332
<211> LENGTH: 645
<212> TYPE: DNA
<213> ORGANISM: Homo sapiens

<400> SEQUENCE: 332

```
gatatcgcac tgacccagcc agcttcagtg agcggctcac caggtcagag cattaccatc    60
tcgtgtacgg gtactagcag cgatgtgggc ggctataact atgtgagctg gtaccagcag   120
catcccggga aggcgccgaa actgatgatt tatgatgtga gcaaccgtcc ctcaggcgtg   180
agcaaccgtt ttagcggatc caaaagcggc aacaccgcga gcctgaccat tagcggcctg   240
caagcggaag acgaagcgga ttattattgc cagagctatg actattatga ttatggtgtg   300
tttggcggcg gcacgaagtt aaccgttctt ggccagccga agccgcacc gagtgtgacg    360
ctgtttccgc cgagcagcga agaattgcag gcgaacaaag cgaccctggt gtgcctgatt   420
agcgacttt atccgggagc cgtgacagtg gcctggaagg cagatagcag ccccgtcaag    480
gcgggagtgg agaccaccac accctccaaa caaagcaaca caagtacgc ggccagcagc    540
tatctgagcc tgacgcctga gcagtggaag tcccacagaa gctacagctg ccaggtcacg   600
catgagggga gcaccgtgga aaaaaccgtt gcgccgactg aggcc                   645
```

<210> SEQ ID NO 333
<211> LENGTH: 645
<212> TYPE: DNA
<213> ORGANISM: Homo sapiens

<400> SEQUENCE: 333

```
gatatcgtgc tgacccagag cccggcgacc ctgagcctgt ctccgggcga acgtgcgacc    60
ctgagctgca gcgcgagcca gagcgtgagc agcagctatc tggcgtggta ccagcagaaa   120
ccaggtcaag caccgcgtct attaatttat ggcgcgagca gccgtgcaac tggggtcccg   180
gcgcgtttta gcggctctgg atccggcacg gattttaccc tgaccattag cagcctggaa   240
cctgaagact ttgcggttta ttattgccag caggctaatg attttcctat tacctttggc   300
cagggtacga aagttgaaat taaacgtacg gtggctgctc cgagcgtgtt tatttttccg   360
ccgagcgatg aacaactgaa aagcggcacg gcgagcgtgg tgtgcctgct gaacaacttt   420
tatccgcgtg aagcgaaagt tcagtggaaa gtagacaacg cgctgcaaag cggcaacagc   480
```

```
caggaaagcg tgaccgaaca ggatagcaaa gatagcacct attctctgag cagcaccctg    540
accctgagca aagcggatta tgaaaaacat aaagtgtatg cgtgcgaagt gacccatcaa    600
ggtctgagca gcccggtgac taaatctttt aatcgtggcg aggcc                    645

<210> SEQ ID NO 334
<211> LENGTH: 648
<212> TYPE: DNA
<213> ORGANISM: Homo sapiens

<400> SEQUENCE: 334
gatatcgcac tgacccagcc agcttcagtg agcggctcac caggtcagag cattaccatc     60
tcgtgtacgg gtactagcag cgatgtgggc ggctataact atgtgagctg gtaccagcag    120
catcccggga aggcgccgaa actgatgatt tatgatgtga gcaaccgtcc ctcaggcgtg    180
agcaaccgtt ttagcggatc caaaagcggc aacaccgcga gcctgaccat tagcggcctg    240
caagcggaag acgaagcgga ttattattgc cagagctggg acaatcttaa gatgcctgtt    300
gtgtttggcg gcggcacgaa gttaaccgtt cttggccagc cgaaagccgc accgagtgtg    360
acgctgtttc cgccgagcag cgaagaattg caggcgaaca aagcgaccct ggtgtgcctg    420
attagcgact tttatccggg agccgtgaca gtggcctgga aggcagatag cagccccgtc    480
aaggcgggag tggagaccac cacaccctcc aaacaaagca caacaagta cgcggccagc    540 agctatctga gcctgacgcc tgagcagtgg aagtcccaca gaagctacag ctgccaggtc    600
acgcatgagg ggagcaccgt ggaaaaaacc gttgcgccga ctgaggcc                 648

<210> SEQ ID NO 335
<211> LENGTH: 648
<212> TYPE: DNA
<213> ORGANISM: Homo sapiens

<400> SEQUENCE: 335
gatatcgcac tgacccagcc agcttcagtg agcggctcac caggtcagag cattaccatc     60
tcgtgtacgg gtactagcag cgatgtgggc ggctataact atgtgagctg gtaccagcag    120
catcccggga aggcgccgaa actgatgatt tatgatgtga gcaaccgtcc ctcaggcgtg    180
agcaaccgtt ttagcggatc caaaagcggc aacaccgcga gcctgaccat tagcggcctg    240
caagcggaag acgaagcgga ttattattgc cagagctatg acgttttcc tattaatcgt    300 gtgtttggcg gcggcacgaa gttaaccgtt cttggccagc cgaaagccgc accgagtgtg    360
acgctgtttc cgccgagcag cgaagaattg caggcgaaca aagcgaccct ggtgtgcctg    420
attagcgact tttatccggg agccgtgaca gtggcctgga aggcagatag cagccccgtc    480
aaggcgggag tggagaccac cacaccctcc aaacaaagca caacaagta cgcggccagc    540 agctatctga gcctgacgcc tgagcagtgg aagtcccaca gaagctacag ctgccaggtc    600
acgcatgagg ggagcaccgt ggaaaaaacc gttgcgccga ctgaggcc                 648

<210> SEQ ID NO 336
<211> LENGTH: 639
<212> TYPE: DNA
<213> ORGANISM: Homo sapiens

<400> SEQUENCE: 336
gatatcgcac tgacccagcc agcttcagtg agcggctcac caggtcagag cattaccatc     60
tcgtgtacgg gtactagcag cgatgtgggc ggctataact atgtgagctg gtaccagcag    120
catcccggga aggcgccgaa actgatgatt tatgatgtga gcaaccgtcc ctcaggcgtg    180
```

```
agcaaccgtt ttagcggatc caaaagcggc aacaccgcga gcctgaccat tagcggcctg    240
caagcggaag acgaagcgga ttattattgc cagagcgatc tttattttcc tgtgtttggc    300
ggcggcacga gttaaccgt tcttggccag ccgaaagccg caccgagtgt gacgctgttt     360
ccgccgagca gcgaagaatt gcaggcgaac aaagcgaccc tggtgtgcct gattagcgac    420
ttttatccgg gagccgtgac agtggcctgg aaggcagata gcagcccgt caaggcggga    480 gtggagacca ccacaccctc caaacaaagc aacaacaagt acgcggccag cagctatctg    540
agcctgacgc ctgagcagtg gaagtcccac agaagctaca gctgccaggt cacgcatgag    600
gggagcaccg tggaaaaaac cgttgcgccg actgaggcc                           639

<210> SEQ ID NO 337
<211> LENGTH: 642
<212> TYPE: DNA
<213> ORGANISM: Homo sapiens

<400> SEQUENCE: 337
gatatcgcac tgacccagcc agcttcagtg agcggctcac caggtcagag cattaccatc     60
tcgtgtacgg gtactagcag cgatgtgggc ggctataact atgtgagctg gtaccagcag    120
catcccggga aggcgccgaa actgatgatt tatgatgtga gcaaccgtcc ctcaggcgtg    180
agcaaccgtt tagcggatc caaaagcggc aacaccgcga gcctgaccat tagcggcctg     240
caagcggaag acgaagcgga ttattattgc cagagctatg acgttactcc tcgtgtgttt    300
ggcggcggca cgaagttaac cgttcttggc cagccgaaag ccgcaccgag tgtgacgctg    360
tttccgccga gcagcgaaga attgcaggcg aacaaagcga ccctggtgtg cctgattagc    420
gacttttatc cgggagccgt gacagtggcc tggaaggcag atagcagccc cgtcaaggcg    480
ggagtggaga ccaccacacc ctccaaacaa agcaacaaca gtacgcggc cagcagctat    540 ctgagcctga cgcctgagca gtggaagtcc cacagaagct acagctgcca ggtcacgcat    600 gagggagca ccgtggaaaa aaccgttgcg ccgactgagg cc                       642

<210> SEQ ID NO 338
<211> LENGTH: 636
<212> TYPE: DNA
<213> ORGANISM: Homo sapiens

<400> SEQUENCE: 338
gatatcgaac tgacccagcc gccttcagtg agcgttgcac caggtcagac cgcgcgtatc     60
tcgtgtagcg gcgatgcgct gggcgataaa tacgcgagct ggtaccagca gaaacccggg    120
caggcgccat tctggtgat ttatgatgat tctgaccgtc cctcaggcat cccggaacgc     180
tttagcggat ccaacagcgg caacaccgcg accctgacca ttagcggcac tcaggcggaa    240
gacgaagcgg attattattg ccagagccgt gaccctgttg gttttcctgt gtttggcggc    300
ggcacgaagt taaccgttct tggccagccg aaagccgcac gagtgtgac gctgtttccg    360 ccgagcagcg aagaattgca ggcgaacaaa gcgaccctgg tgtgcctgat tagcgacttt    420
tatccgggag ccgtgacagt ggcctggaag gcagatagca gccccgtcaa ggcgggagtg    480
gagaccacca caccctccaa acaaagcaac aacaagtacg cggccagcag ctatctgagc    540
ctgacgcctg agcagtggaa gtcccacaga agctacagct gccaggtcac gcatgagggg    600
agcaccgtgg aaaaaaccgt tgcgccgact gaggcc                             636

<210> SEQ ID NO 339
```

```
<211> LENGTH: 642
<212> TYPE: DNA
<213> ORGANISM: Homo sapiens

<400> SEQUENCE: 339
gatatcgcac tgacccagcc agcttcagtg agcggctcac caggtcagag cattaccatc      60
tcgtgtacgg gtactagcag cgatgtgggc ggctataact atgtgagctg gtaccagcag     120
catcccggga aggcgccgaa actgatgatt tatgatgtga gcaaccgtcc ctcaggcgtg     180
agcaaccgtt ttagcggatc caaaagcggc aacaccgcga gcctgaccat tagcggcctg     240
caagcggaag acgaagcgga ttattattgc cagagctatg acctttctcc tcgtgtgttt     300
ggcggcggca cgaagttaac cgttcttggc cagccgaaag ccgcaccgag tgtgacgctg     360
tttccgccga gcagcgaaga attgcaggcg aacaaagcga ccctggtgtg cctgattagc     420
gacttttatc cgggagccgt gacagtggcc tggaaggcag atagcagccc cgtcaaggcg     480
ggagtggaga ccaccacacc ctccaaacaa agcaacaaca gtacgcggc cagcagctat      540
ctgagcctga cgcctgagca gtggaagtcc cacagaagct acagctgcca ggtcacgcat     600
gaggggagca ccgtggaaaa aaccgttgcg ccgactgagg cc                        642

<210> SEQ ID NO 340
<211> LENGTH: 648
<212> TYPE: DNA
<213> ORGANISM: Homo sapiens

<400> SEQUENCE: 340
gatatcgcac tgacccagcc agcttcagtg agcggctcac caggtcagag cattaccatc      60
tcgtgtacgg gtactagcag cgatgtgggc ggctataact atgtgagctg gtaccagcag     120
catcccggga aggcgccgaa actgatgatt tatgatgtga gcaaccgtcc ctcaggcgtg     180
agcaaccgtt ttagcggatc caaaagcggc aacaccgcga gcctgaccat tagcggcctg     240
caagcggaag acgaagcgga ttattattgc cagagctatg acttttctca ttatttttt      300
gtgtttggcg gcggcacgaa gttaaccgtt cttggccagc cgaaagccgc accgagtgtg     360
acgctgtttc cgccgagcag cgaagaattg caggcgaaca aagcgaccct ggtgtgcctg     420
attagcgact tttatccggg agccgtgaca gtggcctgga aggcagatag cagccccgtc     480
aaggcgggag tggagaccac cacaccctcc aaacaaagca acaacaagta cgcggccagc     540
agctatctga gcctgacgcc tgagcagtgg aagtcccaca gaagctacag ctgccaggtc     600
acgcatgagg ggagcaccgt ggaaaaaacc gttgcgccga ctgaggcc                  648

<210> SEQ ID NO 341
<211> LENGTH: 636
<212> TYPE: DNA
<213> ORGANISM: Homo sapiens

<400> SEQUENCE: 341
gatatcgaac tgacccagcc gccttcagtg agcgttgcac caggtcagac cgcgcgtatc      60
tcgtgtagcg gcgatgcgct gggcgataaa tacgcgagct ggtaccagca gaaacccggg     120
caggcgccag ttctggtgat ttatgatgat tctgaccgtc cctcaggcat cccggaacgc     180
tttagcggat ccaacagcgg caacaccgcg accctgacca ttagcggcac tcaggcggaa     240
gacgaagcgg attattattg ccagagctat gaccttcgtt attctcatgt gtttggcggc     300
ggcacgaagt taaccgttct tggccagccg aaagccgcac cgagtgtgac gctgtttccg     360
ccgagcagcg aagaattgca ggcgaacaaa gcgaccctgg tgtgcctgat tagcgacttt     420
```

```
tatccgggag ccgtgacagt ggcctggaag gcagatagca gccccgtcaa ggcgggagtg    480
gagaccacca caccctccaa acaaagcaac aacaagtacg cggccagcag ctatctgagc    540
ctgacgcctg agcagtggaa gtcccacaga agctacagct gccaggtcac gcatgagggg    600
agcaccgtgg aaaaaaccgt tgcgccgact gaggcc                              636
```

<210> SEQ ID NO 342
<211> LENGTH: 642
<212> TYPE: DNA
<213> ORGANISM: Homo sapiens

<400> SEQUENCE: 342

```
gatatcgcac tgacccagcc agcttcagtg agcggctcac caggtcagag cattaccatc    60
tcgtgtacgg gtactagcag cgatgtgggc ggctataact atgtgagctg gtaccagcag    120
catcccggga aggcgccgaa actgatgatt tatgatgtga gcaaccgtcc ctcaggcgtg    180
agcaaccgtt ttagcggatc caaaagcggc aacaccgcga gcctgaccat tagcggcctg    240
caagcggaag acgaagcgga ttattattgc cagagctatg accttcgtaa tcgtgtgttt    300
ggcggcggca cgaagttaac cgttcttggc cagccgaaag ccgcaccgag tgtgacgctg    360
tttccgccga gcagcgaaga attgcaggca acaaagcga ccctggtgtg cctgattagc    420
gacttttatc cgggagccgt gacagtgccc tggaaggcag atagcagccc cgtcaaggcg    480
ggagtggaga ccaccacacc ctccaaacaa agcaacaaca gtacgcggc cagcagctat    540 ctgagcctga cgcctgagca gtggaagtcc cacagaagct acagctgcca ggtcacgcat    600
gaggggagca ccgtggaaaa aaccgttgcg ccgactgagg cc                      642
```

<210> SEQ ID NO 343
<211> LENGTH: 645
<212> TYPE: DNA
<213> ORGANISM: Homo sapiens

<400> SEQUENCE: 343

```
gatatcgcac tgacccagcc agcttcagtg agcggctcac caggtcagag cattaccatc    60
tcgtgtacgg gtactagcag cgatgtgggc ggctataact atgtgagctg gtaccagcag    120
catcccggga aggcgccgaa actgatgatt tatgatgtga gcaaccgtcc ctcaggcgtg    180
agcaaccgtt ttagcggatc caaaagcggc aacaccgcga gcctgaccat tagcggcctg    240
caagcggaag acgaagcgga ttattattgc cagagctatg actttactta tggttctgtg    300
tttggcggcg gcacgaagtt aaccgttctt ggccagccga agccgcacc gagtgtgacg    360 ctgtttccgc cgagcagcga agaattgcag gcgaacaaag cgaccctggt gtgcctgatt    420
agcgactttt atccgggagc cgtgacagtg gcctggaagg cagatagcag ccccgtcaag    480
gcgggagtgg agaccaccac accctccaaa caaagcaaca caagtacgc ggccagcagc    540 tatctgagcc tgacgcctga gcagtggaag tcccacagaa gctacagctg ccaggtcacg    600
catgagggga gcaccgtgga aaaaaccgtt gcgccgactg aggcc                   645
```

<210> SEQ ID NO 344
<211> LENGTH: 645
<212> TYPE: DNA
<213> ORGANISM: Homo sapiens

<400> SEQUENCE: 344

```
gatatcgtgc tgacccagag cccggcgacc ctgagcctgt ctccgggcga acgtgcgacc    60
```

```
ctgagctgca gagcgagcca gagcgtgagc agcagctatc tggcgtggta ccagcagaaa      120
ccaggtcaag caccgcgtct attaatttat ggcgcgagca gccgtgcaac tggggtcccg      180
gcgcgtttta gcggctctgg atccggcacg gattttaccc tgaccattag cagcctggaa      240
cctgaagact ttgcggttta ttattgccag cagtttaatg attctcctta tacctttggc      300
cagggtacga agttgaaat taaacgtacg gtggctgctc cgagcgtgtt tatttttccg       360
ccgagcgatg aacaactgaa aagcggcacg gcgagcgtgg tgtgcctgct gaacaacttt      420
tatccgcgtg aagcgaaagt tcagtggaaa gtagacaacg cgctgcaaag cggcaacagc      480
caggaaagcg tgaccgaaca ggatagcaaa gatagcacct attctctgag cagcacccctg     540 accctgagca agcggattta tgaaaaacat aaagtgtatg cgtgcgaagt gacccatcaa      600
ggtctgagca gcccggtgac taaatctttt aatcgtggcg aggcc                     645

<210> SEQ ID NO 345
<211> LENGTH: 649
<212> TYPE: DNA
<213> ORGANISM: Homo sapiens

<400> SEQUENCE: 345
ggccgatatc gcactgaccc agccagcttc agtgagcggc tcaccaggtc agagcattac       60
catctcgtgt acgggtacta gcagcgatgt gggcggctat aactatgtga gctggtacca      120
gcagcatccc gggaaggcgc cgaaactgat gatttatgat gtgagcaacc gtccctcagg      180
cgtgagcaac cgttttagcg gatccaaaag cggcaacacc gcgagcctga ccattagcgg      240
cctgcaagcg gaagacgaag cggattatta ttgccagagc tatgacattt ctggttatcc      300
tgtgtttggc ggcggcacga gttaaccgt tcttggccag ccgaaagccg caccgagtgt      360
gacgctgttt ccgccgagca gcgaagaatt gcaggcgaac aaagcgaccc tggtgtgcct      420
gattagcgac ttttatccgg gagccgtgac agtggcctgg aaggcagata gcagccccgt      480
caaggcggga gtggagacca ccacaccctc caaacaaagc aacaacaagt acgcggccag      540
cagctatctg agcctgacgc ctgagcagtg aagtcccac agaagctaca gctgccaggt      600
cacgcatgag gggagcaccg tggaaaaaac cgttgcgccg actgaggcc                  649

<210> SEQ ID NO 346
<211> LENGTH: 648
<212> TYPE: DNA
<213> ORGANISM: Homo sapiens

<400> SEQUENCE: 346
gatatcgcac tgacccagcc agcttcagtg agcggctcac caggtcagag cattaccatc       60
tcgtgtacgg gtactagcag cgatgtgggc ggctataact atgtgagctg gtaccagcag      120
catcccggga aggcgccgaa actgatgatt tatgatgtga gcaaccgtcc ctcaggcgtg      180
agcaaccgtt ttagcggatc caaaagcggc aacaccgcga gcctgaccat tagcggcctg      240
caagcggaag acgaagcgga ttattattgc cagagccgtg acctttatta tgtttattat      300
gtgtttggcg gcggcacgaa gttaaccgtt cttggccagc cgaaagccgc accgagtgtg      360
acgctgtttc cgccgagcag cgaagaattg caggcgaaca aagcgaccct ggtgtgcctg      420
attagcgact tttatccggg agccgtgaca gtggcctgga aggcagatag cagccccgtc      480
aaggcgggag tggagaccac cacaccctcc aaacaaagca acaacaagta cgcggccagc      540
agctatctga gcctgacgcc tgagcagtgg aagtcccaca gaagctacag ctgccaggtc      600
acgcatgagg ggagcaccgt ggaaaaaacc gttgcgccga ctgaggcc                   648
```

<210> SEQ ID NO 347
<211> LENGTH: 633
<212> TYPE: DNA
<213> ORGANISM: Homo sapiens

<400> SEQUENCE: 347

| gatatcgaac tgacccagcc gccttcagtg agcgttgcac caggtcagac cgcgcgtatc | 60 |
| tcgtgtagcg gcgatgcgct gggcgataaa tacgcgagct ggtaccagca gaaacccggg | 120 |
| caggcgccag ttctggtgat ttatgatgat tctgaccgtc cctcaggcat cccggaacgc | 180 |
| tttagcggat ccaacagcgg caacaccgcg accctgacca ttagcggcac tcaggcggaa | 240 |
| gacgaagcgg attattattg ccagagctat gaccgttcta tgtgggtgtt tggcggcggc | 300 |
| acgaagttaa ccgttcttgg ccagccgaaa gccgcaccga gtgtgacgct gtttccgccg | 360 |
| agcagcgaag aattgcaggc gaacaaagcg accctggtgt gcctgattag cgactttttat | 420 |
| ccgggagccg tgacagtggc ctggaaggca gatagcagcc cgtcaaggc gggagtggag | 480 |
| accaccacac cctccaaaca agcaacaac aagtacgcgg ccagcagcta tctgagcctg | 540 |
| acgcctgagc agtggaagtc ccacagaagc tacagctgcc aggtcacgca tgaggggagc | 600 |
| accgtggaaa aaccgttgc gccgactgag gcc | 633 |

<210> SEQ ID NO 348
<211> LENGTH: 645
<212> TYPE: DNA
<213> ORGANISM: Homo sapiens

<400> SEQUENCE: 348

| gatatcgcac tgacccagcc agcttcagtg agcggctcac caggtcagag cattaccatc | 60 |
| tcgtgtacgg gtactagcag cgatgtgggc ggctataact atgtgagctg gtaccagcag | 120 |
| catcccggga aggcgccgaa actgatgatt tatgatgtga gcaaccgtcc ctcaggcgtg | 180 |
| agcaaccgtt ttagcggatc caaaagcggc aacaccgcga gcctgaccat tagcggcctg | 240 |
| caagcggaag acgaagcgga ttattattgc cagagctggg acgttcagac tgataaggtg | 300 |
| tttggcggcg gcacgaagtt aaccgttctt ggccagccga agccgcacc gagtgtgacg | 360 |
| ctgtttccgc cgagcagcga agaattgcag gcgaacaaag cgaccctggt gtgcctgatt | 420 |
| agcgactttt atccgggagc cgtgacagtg gcctggaagg cagatagcag ccccgtcaag | 480 |
| gcgggagtgg agaccaccac accctccaaa caaagcaaca caagtacgc ggccagcagc | 540 |
| tatctgagcc tgacgcctga gcagtggaag tcccacagaa gctacagctg ccaggtcacg | 600 |
| catgagggga gcaccgtgga aaaaccgtt gcgccgactg aggcc | 645 |

<210> SEQ ID NO 349
<211> LENGTH: 636
<212> TYPE: DNA
<213> ORGANISM: Homo sapiens

<400> SEQUENCE: 349

| gatatcgaac tgacccagcc gccttcagtg agcgttgcac caggtcagac cgcgcgtatc | 60 |
| tcgtgtagcg gcgatgcgct gggcgataaa tacgcgagct ggtaccagca gaaacccggg | 120 |
| caggcgccag ttctggtgat ttatgatgat tctgaccgtc cctcaggcat cccggaacgc | 180 |
| tttagcggat ccaacagcgg caacaccgcg accctgacca ttagcggcac tcaggcggaa | 240 |
| gacgaagcgg attattattg ccagagctgg gacccttctc attattatgt gtttggcggc | 300 |

```
ggcacgaagt taaccgttct tggccagccg aaagccgcac cgagtgtgac gctgtttccg      360
ccgagcagcg aagaattgca ggcgaacaaa gcgaccctgg tgtgcctgat tagcgacttt      420
tatccgggag ccgtgacagt ggcctggaag gcagatagca gccccgtcaa ggcgggagtg      480
gagaccacca caccctccaa acaaagcaac aacaagtacg cggccagcag ctatctgagc      540
ctgacgcctg agcagtggaa gtcccacaga agctacagct gccaggtcac gcatgagggg      600
agcaccgtgg aaaaaaccgt tgcgccgact gaggcc                                636
```

<210> SEQ ID NO 350
<211> LENGTH: 645
<212> TYPE: DNA
<213> ORGANISM: Homo sapiens

<400> SEQUENCE: 350

```
gatatcgcac tgacccagcc agcttcagtg agcggctcac caggtcagag cattaccatc       60
tcgtgtacgg gtactagcag cgatgtgggc ggctataact atgtgagctg gtaccagcag      120
catcccggga aggcgccgaa actgatgatt tatgatgtga caaccgtcc ctcaggcgtg       180 agcaaccgtt ttagcggatc caaaagcggc aacaccgcga gcctgaccat tagcggcctg      240
caagcggaag acgaagcgga ttattattgc cagagctatg acattatgcc tgagcgtgtg      300
tttggcggcg gcacgaagtt aaccgttctt ggccagccga agccgcacc gagtgtgacg       360 ctgtttccgc cgagcagcga agaattgcag gcgaacaaag cgaccctggt gtgcctgatt      420
agcgactttt atccgggagc cgtgacagtg gcctggaagg cagatagcag ccccgtcaag      480
gcgggagtgg agaccaccac accctccaaa caaagcaaca acaagtacgc ggccagcagc      540
tatctgagcc tgacgcctga gcagtggaag tcccacagaa gctacagctg ccaggtcacg      600
catgagggga gcaccgtgga aaaaaccgtt gcgccgactg aggcc                      645
```

<210> SEQ ID NO 351
<211> LENGTH: 645
<212> TYPE: DNA
<213> ORGANISM: Homo sapiens

<400> SEQUENCE: 351

```
gatatcgcac tgacccagcc agcttcagtg agcggctcac caggtcagag cattaccatc       60
tcgtgtacgg gtactagcag cgatgtgggc ggctataact atgtgagctg gtaccagcag      120
catcccggga aggcgccgaa actgatgatt tatgatgtga caaccgtcc ctcaggcgtg       180 agcaaccgtt ttagcggatc caaaagcggc aacaccgcga gcctgaccat tagcggcctg      240
caagcggaag acgaagcgga ttattattgc cagagcatgg actttcgtct tatgcatgtg      300
tttggcggcg gcacgaagtt aaccgttctt ggccagccga agccgcacc gagtgtgacg       360 ctgtttccgc cgagcagcga agaattgcag gcgaacaaag cgaccctggt gtgcctgatt      420
agcgactttt atccgggagc cgtgacagtg gcctggaagg cagatagcag ccccgtcaag      480
gcgggagtgg agaccaccac accctccaaa caaagcaaca acaagtacgc ggccagcagc      540
tatctgagcc tgacgcctga gcagtggaag tcccacagaa gctacagctg ccaggtcacg      600
catgagggga gcaccgtgga aaaaaccgtt gcgccgactg aggcc                      645
```

<210> SEQ ID NO 352
<211> LENGTH: 645
<212> TYPE: DNA
<213> ORGANISM: Homo sapiens

<400> SEQUENCE: 352

```
gatatcgcac tgacccagcc agcttcagtg agcggctcac caggtcagag cattaccatc        60
tcgtgtacgg gtactagcag cgatgtgggc ggctataact atgtgagctg gtaccagcag       120
catcccggga aggcgccgaa actgatgatt tatgatgtga caaccgtcc ctcaggcgtg        180 agcaaccgtt ttagcggatc caaaagcggc aacaccgcga gcctgaccat tagcggcctg      240
caagcggaag acgaagcgga ttattattgc cagagctttg acatgattca tccttatgtg      300
tttggcggcg gcacgaagtt aaccgttctt ggccagccga agccgcacc gagtgtgacg        360 ctgtttccgc cgagcagcga agaattgcag gcgaacaaag cgaccctggt gtgcctgatt      420
agcgactttt atccgggagc cgtgacagtg gcctggaagg cagatagcag ccccgtcaag      480
gcgggagtgg agaccaccac accctccaaa caaagcaaca caagtacgc ggccagcagc        540 tatctgagcc tgacgcctga gcagtggaag tcccacagaa gctacagctg ccaggtcacg      600
catgagggga gcaccgtgga aaaaaccgtt gcgccgactg aggcc                       645

<210> SEQ ID NO 353
<211> LENGTH: 639
<212> TYPE: DNA
<213> ORGANISM: Homo sapiens

<400> SEQUENCE: 353
gatatcgcac tgacccagcc agcttcagtg agcggctcac caggtcagag cattaccatc        60
tcgtgtacgg gtactagcag cgatgtgggc ggctataact atgtgagctg gtaccagcag       120
catcccggga aggcgccgaa actgatgatt tatgatgtga caaccgtcc ctcaggcgtg        180 agcaaccgtt ttagcggatc caaaagcggc aacaccgcga gcctgaccat tagcggcctg      240
caagcggaag acgaagcgga ttattattgc cagagcgact ttcctgttat ggtgtttggc      300
ggcggcacga agttaaccgt tcttggccag ccgaaagccg caccgagtgt gacgctgttt      360
ccgccgagca gcgaagaatt gcaggcgaac aaagcgaccc tggtgtgcct gattagcgac      420
ttttatccgg gagccgtgac agtggcctgg aaggcagata gcagccccgt caaggcggga      480
gtggagacca ccacaccctc caaacaaagc aacaacaagt acgcggccag cagctatctg      540
agcctgacgc ctgagcagtg gaagtcccac agaagctaca gctgccaggt cacgcatgag      600 ggagcaccg tggaaaaaac cgttgcgccg actgaggcc                              639

<210> SEQ ID NO 354
<211> LENGTH: 639
<212> TYPE: DNA
<213> ORGANISM: Homo sapiens

<400> SEQUENCE: 354
gatatcgcac tgacccagcc agcttcagtg agcggctcac caggtcagag cattaccatc        60
tcgtgtacgg gtactagcag cgatgtgggc ggctataact atgtgagctg gtaccagcag       120
catcccggga aggcgccgaa actgatgatt tatgatgtga caaccgtcc ctcaggcgtg        180 agcaaccgtt ttagcggatc caaaagcggc aacaccgcga gcctgaccat tagcggcctg      240
caagcggaag acgaagcgga ttattattgc cagagcgaca tccttatct tgtgtttggc      300 ggcggcacga agttaaccgt tcttggccag ccgaaagccg caccgagtgt gacgctgttt      360
ccgccgagca gcgaagaatt gcaggcgaac aaagcgaccc tggtgtgcct gattagcgac      420
ttttatccgg gagccgtgac agtggcctgg aaggcagata gcagccccgt caaggcggga      480
gtggagacca ccacaccctc caaacaaagc aacaacaagt acgcggccag cagctatctg      540
```

-continued

```
agcctgacgc ctgagcagtg gaagtcccac agaagctaca gctgccaggt cacgcatgag    600
gggagcaccg tggaaaaaac cgttgcgccg actgaggcc                           639
```

<210> SEQ ID NO 355
<211> LENGTH: 10
<212> TYPE: PRT
<213> ORGANISM: Homo sapiens

<400> SEQUENCE: 355

Gly Phe Thr Phe Ser Ser Tyr Ala Met Ser
1               5                   10

<210> SEQ ID NO 356
<211> LENGTH: 10
<212> TYPE: PRT
<213> ORGANISM: Homo sapiens

<400> SEQUENCE: 356

Gly Phe Thr Phe Asn Ser Tyr Ala Met Ser
1               5                   10

<210> SEQ ID NO 357
<211> LENGTH: 17
<212> TYPE: PRT
<213> ORGANISM: Homo sapiens

<400> SEQUENCE: 357

Ala Ile Ser Gly Ser Gly Gly Ser Thr Tyr Tyr Ala Asp Ser Val Lys
1               5                   10                  15
Gly

<210> SEQ ID NO 358
<211> LENGTH: 17
<212> TYPE: PRT
<213> ORGANISM: Homo sapiens

<400> SEQUENCE: 358

Val Ile Ser Gly Asn Gly Ser Asn Thr Tyr Tyr Ala Asp Ser Val Lys
1               5                   10                  15
Gly

<210> SEQ ID NO 359
<211> LENGTH: 17
<212> TYPE: PRT
<213> ORGANISM: Homo sapiens

<400> SEQUENCE: 359

Gly Ile Ser Gly Asn Gly Val Leu Ile Phe Tyr Ala Asp Ser Val Lys
1               5                   10                  15
Gly

<210> SEQ ID NO 360
<211> LENGTH: 5
<212> TYPE: PRT
<213> ORGANISM: Homo sapiens

<400> SEQUENCE: 360

Gly Leu Met Asp Tyr
1               5

<210> SEQ ID NO 361
<211> LENGTH: 4

```
<212> TYPE: PRT
<213> ORGANISM: Homo sapiens

<400> SEQUENCE: 361

Trp Phe Asp His
  1

<210> SEQ ID NO 362
<211> LENGTH: 4
<212> TYPE: PRT
<213> ORGANISM: Homo sapiens

<400> SEQUENCE: 362

Trp Phe Asp Val
  1

<210> SEQ ID NO 363
<211> LENGTH: 14
<212> TYPE: PRT
<213> ORGANISM: Homo sapiens

<400> SEQUENCE: 363

Thr Gly Thr Ser Ser Asp Val Gly Gly Tyr Asn Tyr Val Ser
  1               5                  10

<210> SEQ ID NO 364
<211> LENGTH: 7
<212> TYPE: PRT
<213> ORGANISM: Homo sapiens

<400> SEQUENCE: 364

Asp Val Ser Asn Arg Pro Ser
  1               5

<210> SEQ ID NO 365
<211> LENGTH: 9
<212> TYPE: PRT
<213> ORGANISM: Homo sapiens

<400> SEQUENCE: 365

Gln Ser Tyr Asp Phe Ile Arg Phe Met
  1               5

<210> SEQ ID NO 366
<211> LENGTH: 10
<212> TYPE: PRT
<213> ORGANISM: Homo sapiens

<400> SEQUENCE: 366

Gly Gly Thr Phe Ser Ser Tyr Ala Ile Ser
  1               5                  10

<210> SEQ ID NO 367
<211> LENGTH: 10
<212> TYPE: PRT
<213> ORGANISM: Homo sapiens

<400> SEQUENCE: 367

Gly Tyr Ser Phe Thr Ser Tyr Trp Ile Gly
  1               5                  10

<210> SEQ ID NO 368
<211> LENGTH: 17
<212> TYPE: PRT
<213> ORGANISM: Homo sapiens
```

<400> SEQUENCE: 368

Gly Ile Ile Pro Ile Phe Gly Thr Ala Asn Tyr Ala Gln Lys Phe Gln
1               5                   10                  15
Gly

<210> SEQ ID NO 369
<211> LENGTH: 17
<212> TYPE: PRT
<213> ORGANISM: Homo sapiens

<400> SEQUENCE: 369

Ile Ile Tyr Pro Gly Asp Ser Asp Thr Arg Tyr Ser Pro Ser Phe Gln
1               5                   10                  15
Gly

<210> SEQ ID NO 370
<211> LENGTH: 16
<212> TYPE: PRT
<213> ORGANISM: Homo sapiens

<400> SEQUENCE: 370

Trp Ser Asp Gln Ser Tyr His Tyr Tyr Trp His Pro Tyr Phe Asp Val
1               5                   10                  15

<210> SEQ ID NO 371
<211> LENGTH: 13
<212> TYPE: PRT
<213> ORGANISM: Homo sapiens

<400> SEQUENCE: 371

Ser Gly Ser Ser Ser Asn Ile Gly Ser Asn Tyr Val Ser
1               5                   10

<210> SEQ ID NO 372
<211> LENGTH: 14
<212> TYPE: PRT
<213> ORGANISM: Homo sapiens

<400> SEQUENCE: 372

Thr Gly Thr Ser Ser Asp Leu Gly Gly Tyr Asn Tyr Val Ser
1               5                   10

<210> SEQ ID NO 373
<211> LENGTH: 11
<212> TYPE: PRT
<213> ORGANISM: Homo sapiens

<400> SEQUENCE: 373

Leu Met Ile Tyr Asp Asn Asn Gln Arg Pro Ser
1               5                   10

<210> SEQ ID NO 374
<211> LENGTH: 11
<212> TYPE: PRT
<213> ORGANISM: Homo sapiens

<400> SEQUENCE: 374

Leu Met Ile Tyr Asp Val Ser Asn Arg Pro Ser
1               5                   10

<210> SEQ ID NO 375
<211> LENGTH: 11

```
<212> TYPE: PRT
<213> ORGANISM: Homo sapiens

<400> SEQUENCE: 375

Leu Met Ile Tyr Ala Gly Asn Asn Arg Pro Ser
 1               5                  10

<210> SEQ ID NO 376
<211> LENGTH: 10
<212> TYPE: PRT
<213> ORGANISM: Homo sapiens

<400> SEQUENCE: 376

Gln Ala Phe Asp Val Ala Pro Asn Gly Lys
 1               5                  10

<210> SEQ ID NO 377
<211> LENGTH: 10
<212> TYPE: PRT
<213> ORGANISM: Homo sapiens

<400> SEQUENCE: 377

Gln Ala Phe Ala Val Met Pro Asn Val Glu
 1               5                  10

<210> SEQ ID NO 378
<211> LENGTH: 10
<212> TYPE: PRT
<213> ORGANISM: Homo sapiens

<400> SEQUENCE: 378

Gln Ser Phe Thr Val Ser Pro Gly Ala Asp
 1               5                  10

<210> SEQ ID NO 379
<211> LENGTH: 9
<212> TYPE: PRT
<213> ORGANISM: Homo sapiens

<400> SEQUENCE: 379

Gln Ala Tyr Asp Ser Ser Gly Tyr Pro
 1               5

<210> SEQ ID NO 380
<211> LENGTH: 17
<212> TYPE: DNA
<213> ORGANISM: Homo sapiens

<400> SEQUENCE: 380
gtggtggttc cgatatc                                              17

<210> SEQ ID NO 381
<211> LENGTH: 43
<212> TYPE: DNA
<213> ORGANISM: Homo sapiens

<400> SEQUENCE: 381
agcgtcacac tcggtgcggc tttcggctgg ccaagaacgg tta                 43
```

US 7,091,323 B2

HUMAN TIMP-1 ANTIBODIES

This application claims priority to and incorporates by reference co-pending provisional application Ser. No. 60/285,683 filed Apr. 24, 2001.

This application incorporates by reference the sequence listing contained on a compact disc, which is part of the application. The sequence listing is a 1.17 MB ASCII file named "Human TIMP-1 Antibodies sequence listing.txt," created on Apr. 23, 2002.

FIELD OF THE INVENTION

The invention relates to TIMP-1-binding human antibodies.

BACKGROUND OF THE INVENTION

Tissue inhibitors of metalloproteases (TIMPs) inhibit metalloproteases, a family of endopeptide hydrolases. Metalloproteases are secreted by connective tissue and hematopoietic cells, use $Zn^{2+}$ or $Ca^{2+}$ for catalysis, and may be inactivated by metal chelators as well as TIMP molecules. Matrix metalloproteases (MMPs) participate in a variety of biologically important processes, including the degradation of many structural components of tissues, particularly the extracellular matrix (ECM).

Degradation of extracellular matrix tissue is desirable in processes where destruction of existing tissues is necessary, e.g., in embryo implantation (Reponen et al., *Dev. Dyn.* 202, 388–96, 1995), embryogenesis, and tissue remodeling. Imbalance between synthesis and degradation of matrix proteins, however, can result in diseases such as liver fibrosis (Iredale et al., *Hepatology* 24, 176–84, 1996). This imbalance can occur, for example, if levels of TIMPs are increased. Disorders in which TIMP-1 levels of increased include, for example, liver fibrosis, alcoholic liver disease, cardiac fibrosis, acute coronary syndrome, lupus nephritis, glomerulosclerotic renal disease, idiopathic pulmonary fibrosis, benign prostate hypertrophy, lung cancer, and colon cancer. See, e.g., Inokubo et al., *Am. Heart J.* 141, 211–17, 2001; Ylisirnio et al., *Anticancer Res.* 20, 1311–16, 2000; Holten-Andersen et al., *Clin. Cancer Res.* 6, 4292–99, 2000; Holten-Andersen et al., *Br. J. Cancer* 80, 495–503, 1999; Peterson et al., *Cardiovascular Res.* 46, 307–15, 2000; Arthur et al., *Alcoholism: Clinical and Experimental Res.* 23, 840–43, 1999; Iredale et al., *Hepatol.* 24, 176–84, 1996.

There is a need in the art for reagents and methods of inhibiting TIMP-1 activity, which can be used to provide therapeutic effects.

BRIEF SUMMARY OF THE INVENTION

It is an object of the present invention to provide reagents and methods of inhibiting TIMP-1 activity. This and other objects of the invention are provided by one or more of the embodiments described below.

One embodiment of the invention is a purified preparation of a human antibody, wherein the antibody binds to a tissue inhibitor of metalloprotease-1 (TIMP-1) and neutralizes a matrix metalloprotease (MMP)-inhibiting activity of the TIMP-1.

Another embodiment of the invention is a purified preparation of a first human antibody which comprises a VHCDR3 region comprising an amino acid sequence selected from the group consisting of SEQ ID NOS:1–43 and 360.

Still another embodiment of the invention is a purified preparation of a first human antibody which comprises a VLCDR3 region comprising an amino acid sequence selected from the group consisting of SEQ ID NOS:44–86 and 365–379.

Yet another embodiment of the invention is a purified preparation of a first human antibody which has TIMP-1 binding and MMP-inhibiting activity characteristics of a second human antibody. The second antibody comprises a VHCDR3 and VLCDR3 amino acid sequence pair selected from the group consisting of SEQ ID NOS:1 and 44, SEQ ID NOS:2 and 45, SEQ ID NO:3 and 46, SEQ ID NOS:4 and 47, SEQ ID NOS:5 and 48, SEQ ID NOS:6 and 49, SEQ ID NOS:7 and 50, SEQ ID NOS:3 and 44, SEQ ID NOS:3 and 45, SEQ ID NOS:3 and 47, SEQ ID NOS:3 and 48, SEQ ID NOS:3 and 49, SEQ ID NOS:3 and 50, SEQ ID NOS:7 and 44, SEQ ID NOS:7 and 45, SEQ ID NOS:7 and 47, SEQ ID NOS:7 and 48, SEQ ID NOS:8 and 51, SEQ ID NOS:9 and 52, SEQ ID NOS:10 and 53, SEQ ID NOS:11 and 54, SEQ ID NOS:12 and 55, SEQ ID NOS:13 and 56, SEQ ID NOS:14 and 57, SEQ ID NOS:15 and 58, SEQ ID NOS:16 and 59, SEQ ID NOS:17 and 60, SEQ ID NOS:18 and 61, SEQ ID NOS:19 and 62, SEQ ID NOS:20 and 63, SEQ ID NOS:21 and 64, SEQ ID NOS:22 and 65, SEQ ID NOS:23 and 66, SEQ ID NOS:24 and 67, SEQ ID NOS:25 and 68, SEQ ID NOS:26 and 69, SEQ ID NOS: 27 and 70, SEQ ID NOS:28 and 71, SEQ ID NOS:29 and 72, SEQ ID NOS:30 and 73, SEQ ID NOS:31 and 74, SEQ ID NOS:32 and 75, SEQ ID NOS:33 and 76, SEQ ID NOS:34 and 77, SEQ ID NOS:35 and 78, SEQ ID NOS:36 and 79, SEQ ID NOS:37 and 80, SEQ ID NOS:38 and 81, SEQ ID NOS:39 and 82, SEQ ID NOS:40 and 83, SEQ ID NOS:41 and 84, SEQ ID NOS:42 and 85, SEQ ID NOS:43 and 86, SEQ ID NOS:3 and 48, SEQ ID NOS:360 and 48, SEQ ID NOS:3 and 365, SEQ ID NOS:16 and 59, SEQ ID NOS:18 and 61, SEQ ID NOS:34 and 77, SEQ ID NOS:34 and 379, SEQ ID NOS:18 and 376, SEQ ID NOS:18 and 377, and SEQ ID NOS:18 and 378.

Even another embodiment of the invention is a purified preparation of a human antibody comprising a VHCDR3 and VLCDR3 amino acid sequence pair selected from the group consisting of SEQ ID NOS:1 and 44, SEQ ID NOS:2 and 45, SEQ ID NO:3 and 46, SEQ ID NOS:4 and 47, SEQ ID NOS:5 and 48, SEQ ID NOS:6 and 49, SEQ ID NOS:7 and 50, SEQ ID NOS:3 and 44, SEQ ID NOS:3 and 45, SEQ ID NOS:3 and 47, SEQ ID NOS:3 and 48, SEQ ID NOS:3 and 49, SEQ ID NOS:3 and 50, SEQ ID NOS:7 and 44, SEQ ID NOS:7 and 45, SEQ ID NOS:7 and 47, SEQ ID NOS:7 and 48, SEQ ID NOS:8 and 51, SEQ ID NOS:9 and 52, SEQ ID NOS:10 and 53, SEQ ID NOS:11 and 54, SEQ ID NOS:12 and 55, SEQ ID NOS:13 and 56, SEQ ID NOS:14 and 57, SEQ ID NOS:15 and 58, SEQ ID NOS:16 and 59, SEQ ID NOS:17 and 60, SEQ ID NOS:18 and 61, SEQ ID NOS:19 and 62, SEQ ID NOS:20 and 63, SEQ ID NOS:21 and 64, SEQ ID NOS:22 and 65, SEQ ID NOS:23 and 66, SEQ ID NOS:24 and 67, SEQ ID NOS:25 and 68, SEQ ID NOS:26 and 69, SEQ ID NOS: 27 and 70, SEQ ID NOS:28 and 71, SEQ ID NOS:29 and 72, SEQ ID NOS:30 and 73, SEQ ID NOS:31 and 74, SEQ ID NOS:32 and 75, SEQ ID NOS:33 and 76, SEQ ID NOS:34 and 77, SEQ ID NOS:35 and 78, SEQ ID NOS:36 and 79, SEQ ID NOS:37 and 80, SEQ ID NOS:38 and 81, SEQ ID NOS:39 and 82, SEQ ID NOS:40 and 83, SEQ ID NOS:41 and 84, SEQ ID NOS:42 and 85, SEQ ID NOS:43 and 86, SEQ ID NOS:3 and 48, SEQ ID NOS:360 and 48, SEQ ID NOS:3 and 365, SEQ ID NOS:16 and 59, SEQ ID NOS:18 and 61, SEQ ID NOS:34 and 77, SEQ ID NOS:34 and 379, SEQ ID NOS:18 and 376, SEQ ID NOS:18 and 377, and SEQ ID NOS:18 and 378.

A further embodiment of the invention is a purified preparation of a human antibody which comprises a heavy chain and a light chain amino acid pair selected from the group consisting of SEQ ID NOS:140 and 97, SEQ ID NOS:141 and 98, SEQ ID NOS:142 and 99, SEQ ID NOS:143 and 100, SEQ ID NOS:144 and 101, SEQ ID NOS:145 and 102, SEQ ID NOS:146 and 103, SEQ ID NOS:142 and 97, SEQ ID NOS:142 and 98, SEQ ID NOS:142 and 100, SEQ ID NOS:142 and 101, SEQ ID NOS:142 and 102, SEQ ID NOS:142 and 103, SEQ ID NOS:146 and 97, SEQ ID NOS:146 and 98, SEQ ID NO:146 and 100, SEQ ID NOS:146 and 101, SEQ ID NOS:148 and 104, SEQ ID NOS:148 an 105, SEQ ID NOS:149 and 106, SEQ ID NOS:150 and 107, SEQ ID NOS:151 and 108, SEQ ID NOS:152 and 109, SEQ ID NOS:153 and 110, SEQ ID NOS:154 and 111, SEQ ID NOS:155 and 112, SEQ ID NOS:156 and 113, SEQ ID NOS:157 and 114, SEQ ID NOS:158 and 115, SEQ ID NOS:159 and 116, SEQ ID NOS:160 and 117, SEQ ID NOS:161 and 118, SEQ ID NOS:162 and 119, SEQ ID NOS:163 and 120, SEQ ID NOS:164 and 121, SEQ ID NOS:165 and 122, SEQ ID NOS:166 and 123, SEQ ID NOS:167 and 124, SEQ ID NOS:168 and 125, SEQ ID NOS:169 and 126, SEQ ID NOS:170 and 127, SEQ ID NOS:171 and 128, SEQ ID NOS:172 and 129, SEQ ID NOS:173 and 130, SEQ ID NOS:174 and 131, SEQ ID NOS:175 and 132, SEQ ID NOS:176 and 133, SEQ ID NOS:177 and 134, SEQ ID NOS:178 and 135, SEQ ID NOS:179 and 136, SEQ ID NOS:180 and 137, SEQ ID NOS:181 and 138, and SEQ ID NOS:182 and 139.

Another embodiment of the invention is a pharmaceutical composition comprising a human antibody and a pharmaceutically acceptable carrier. The human antibody (1) binds to a TIMP-1 and (2) neutralizes an MMP-inhibiting activity of the TIMP-1.

Yet another embodiment of the invention is a purified polynucleotide which encodes a human antibody comprising a VHCDR3 region which comprises an amino acid sequence selected from the group consisting of SEQ ID NOS:1–43 and 360. The human antibody (1) binds to a TIMP-1 and (2) neutralizes an MMP-inhibiting activity of the TIMP-1.

Even another embodiment of the invention is a purified polynucleotide which encodes a human antibody comprising a VLCDR3 region which comprises an amino acid sequence selected from the group consisting of SEQ ID NOS:44–86 and 365–379. The human antibody (1) binds to a TIMP-1 and (2) neutralizes an MMP-inhibiting activity of the TIMP-1.

Still another embodiment of the invention is an expression vector comprising a polynucleotide which encodes a human antibody comprising a VHCDR3 region which comprises an amino acid sequence selected from the group consisting of SEQ ID NOS:1–43 and 360. The human antibody (1) binds to a TIMP-1 and (2) neutralizes an MMP-inhibiting activity of the TIMP-1.

A further embodiment of the invention is an expression vector comprising a polynucleotide which encodes a human antibody comprising a VHCDR3 region which comprises an amino acid sequence selected from the group consisting of SEQ ID NOS:1–43 and 360. The human antibody (1) binds to a TIMP-1 and (2) neutralizes an MMP-inhibiting activity of the TIMP-1. The VHCDR3 region is encoded by a nucleotide sequence selected from the group consisting of SEQ ID NOS:227–269.

Another embodiment of the invention is an expression vector comprising a polynucleotide which encodes a human antibody comprising a VLCDR3 region which comprises an amino acid sequence selected from the group consisting of SEQ ID NOS:44–86 and 365–379. The human antibody (1) binds to a TIMP-1 and (2) neutralizes an MMP-inhibiting activity of the TIMP-1.

Yet another embodiment of the invention is an expression vector comprising a polynucleotide which encodes a human antibody comprising a VLCDR3 region which comprises an amino acid sequence selected from the group consisting of SEQ ID NOS:44–86 and 365–379. The human antibody (1) binds to a TIMP-1 and (2) neutralizes an MMP-inhibiting activity of the TIMP-1. The VLCDR3 region is encoded by a nucleotide sequence selected from the group consisting of SEQ ID NOS:184–226.

Still another embodiment of the invention is an expression vector comprising a polynucleotide which encodes a human antibody comprising a VHCDR3 region which comprises an amino acid sequence selected from the group consisting of SEQ ID NOS: 1–43 and 360. The human antibody (1) binds to a TIMP-1 and (2) neutralizes an MMP-inhibiting activity of the TIMP-1. The human antibody comprises a heavy chain having an amino acid sequence selected from the group consisting of SEQ ID NOS:140–182.

Even another embodiment of the invention is an expression vector comprising a polynucleotide which encodes a human antibody comprising a VHCDR3 region which comprises an amino acid sequence selected from the group consisting of SEQ ID NOS:1–43 and 360. The human antibody (1) binds to a TIMP-1 and (2) neutralizes an MMP-inhibiting activity of the TIMP-1. The human antibody comprises a heavy chain having an amino acid sequence selected from the group consisting of SEQ ID NOS:140–182. The heavy chain is encoded by a nucleotide sequence selected from the group consisting of SEQ ID NOS:269–311.

A further embodiment of the invention is an expression vector comprising a polynucleotide which encodes a human antibody comprising a VLCDR3 region which comprises an amino acid sequence selected from the group consisting of SEQ ID NOS:44–86 and 365–379. The human antibody (1) binds to a TIMP-1 and (2) neutralizes an MMP-inhibiting activity of the TIMP-1. The human antibody comprises a light chain having an amino acid sequence selected from the group consisting of SEQ ID NOS:97–139.

Another embodiment of the invention is an expression vector comprising a polynucleotide which encodes a human antibody comprising a VLCDR3 region which comprises an amino acid sequence selected from the group consisting of SEQ ID NOS:44–86 and 365–379. The human antibody (1) binds to a TIMP-1 and (2) neutralizes an MMP-inhibiting activity of the TIMP-1. The human antibody comprises a light chain having an amino acid sequence selected from the group consisting of SEQ ID NOS:97–139. The light chain is encoded by a nucleotide sequence selected from the group consisting of SEQ ID NOS:312–354.

Yet another embodiment of the invention is a host cell comprising an expression vector. The expression vector comprises a polynucleotide which encodes a human antibody comprising a VHCDR3 region which comprises an amino acid sequence selected from the group consisting of SEQ ID NOS:1–43 and 360, wherein the human antibody (1) binds to a TIMP-1 and (2) neutralizes an MMP-inhibiting activity of the TIMP-1.

Yet another embodiment of the invention is a host cell comprising an expression vector. The expression vector comprises a polynucleotide which encodes a human antibody comprising a VHCDR3 region which comprises an amino acid sequence selected from the group consisting of SEQ ID NOS:1–43 and 360, wherein the human antibody (1) binds to a TIMP-1 and (2) neutralizes an MMP-inhibiting activity of the TIMP-1. The VHCDR3 region is encoded by a nucleotide sequence selected from the group consisting of SEQ ID NOS:227–269.

Still another embodiment of the invention is a host cell comprising an expression vector. The expression vector comprises a polynucleotide which encodes a human antibody comprising a VLCDR3 region which comprises an amino acid sequence selected from the group consisting of SEQ ID NOS:44–86 and 365–379. The human antibody (1) binds to a TIMP-1 and (2) neutralizes an MMP-inhibiting activity of the TIMP-1.

A further embodiment of the invention is a host cell comprising an expression vector. The expression vector comprises a polynucleotide which encodes a human antibody comprising a VLCDR3 region which comprises an amino acid sequence selected from the group consisting of SEQ ID NOS:44–86 and 365–379. The human antibody (1) binds to a TIMP-1 and (2) neutralizes an MMP-inhibiting activity of the TIMP-1. The VLCDR3 region is encoded by a nucleotide sequence selected from the group consisting of SEQ ID NOS: 184–226.

Another embodiment of the invention is a host cell comprising an expression vector. The expression vector comprises a polynucleotide which encodes a human antibody comprising a VHCDR3 region which comprises an amino acid sequence selected from the group consisting of SEQ ID NOS:1–43 and 360, wherein the human antibody (1) binds to a TIMP-1 and (2) neutralizes an MMP-inhibiting activity of the TIMP-1. The human antibody comprises a heavy chain having an amino acid sequence selected from the group consisting of SEQ ID NOS:140–182.

Still another embodiment of the invention is a host cell comprising an expression vector. The expression vector comprises a polynucleotide which encodes a human antibody comprising a VHCDR3 region which comprises an amino acid sequence selected from the group consisting of SEQ ID NOS:1–43 and 360, wherein the human antibody (1) binds to a TIMP-1 and (2) neutralizes an MMP-inhibiting activity of the TIMP-1. The human antibody comprises a heavy chain having an amino acid sequence selected from the group consisting of SEQ ID NOS:140–182. The heavy chain is encoded by a nucleotide sequence selected from the group consisting of SEQ ID NOS:269–311.

Yet another embodiment of the invention is a host cell comprising an expression vector. The expression vector comprises a polynucleotide which encodes a human antibody comprising a VLCDR3 region which comprises an amino acid sequence selected from the group consisting of SEQ ID NOS:44–86 and 365–379. The human antibody (1) binds to a TIMP-1 and (2) neutralizes an MMP-inhibiting activity of the TIMP-1. The human antibody comprises a light chain having an amino acid sequence selected from the group consisting of SEQ ID NOS:97–139.

Even another embodiment of the invention is a host cell comprising an expression vector. The expression vector comprises a polynucleotide which encodes a human antibody comprising a VLCDR3 region which comprises an amino acid sequence selected from the group consisting of SEQ ID NOS:44–86 and 365–379. The human antibody (1) binds to a TIMP-1 and (2) neutralizes an MMP-inhibiting activity of the TIMP-1. The human antibody comprises a light chain having an amino acid sequence selected from the group consisting of SEQ ID NOS:97–139. The light chain is encoded by a nucleotide sequence selected from the group consisting of SEQ ID NOS:312–354.

A further embodiment of the invention is a method of making a human antibody. The host cell of claim 43 is cultured under conditions whereby the antibody is expressed. The human antibody is purified from the host cell culture.

Another embodiment of the invention is a method of decreasing an MMP-inhibiting activity of a TIMP-1. The TIMP-1 is contacted with a human antibody that binds to the TIMP-1. The MMP-inhibiting activity of the TIMP-1 is decreased relative to MMP-inhibiting activity of the TIMP-1 in the absence of the antibody.

Still another embodiment of the invention is a method of ameliorating symptoms of a disorder in which TIMP-1 is elevated. An effective amount of a human antibody which neutralizes an MMP-inhibiting activity of the TIMP-1 is administered to a patient having the disorder. Symptoms of the disorder are thereby ameliorated.

A further embodiment of the invention is a method of detecting a TIMP-1 in a test preparation. The test preparation is contacted with a human antibody that specifically binds to the TIMP-1. The test preparation is assayed for the presence of an antibody-TIMP-1 complex.

Even another embodiment of the invention is a method to aid in diagnosing a disorder in which a TIMP-1 level is elevated. A sample from a patient suspected of having the disorder is contacted with a human antibody that binds to TIMP-1. The sample is assayed for the presence of an antibody-TIMP-1 complex. Detection of an amount of the complex which is greater than an amount of the complex in a normal sample identifies the patient as likely to have the disorder.

The invention thus provides human antibodies which bind to TIMP-1 and neutralize MMP-inhibiting activity of TIMP-1. These antibodies can be used, inter alia, in diagnostic and therapeutic methods.

BRIEF DESCRIPTION OF THE FIGURES

Figure 1:
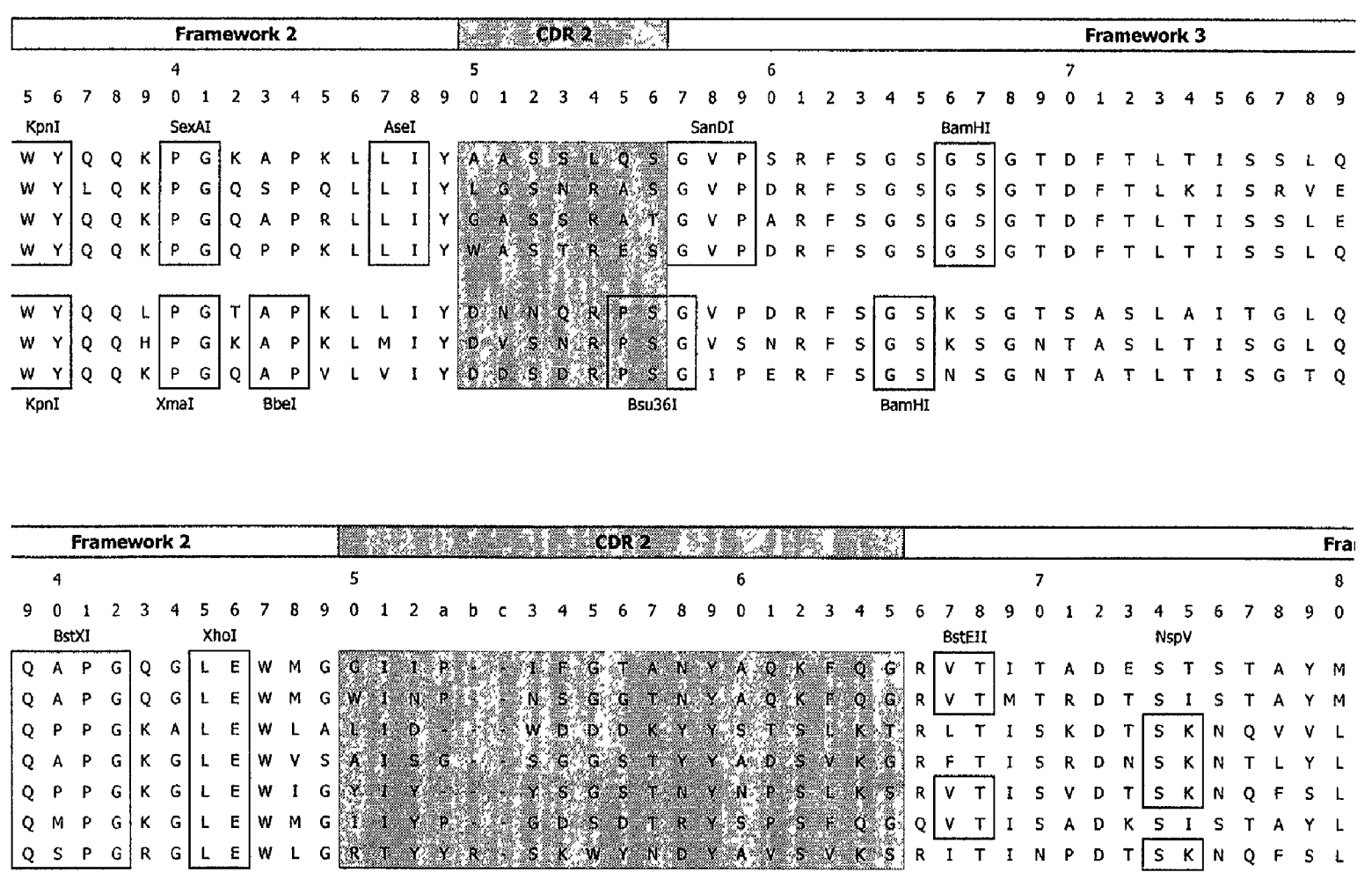
Figure 1:
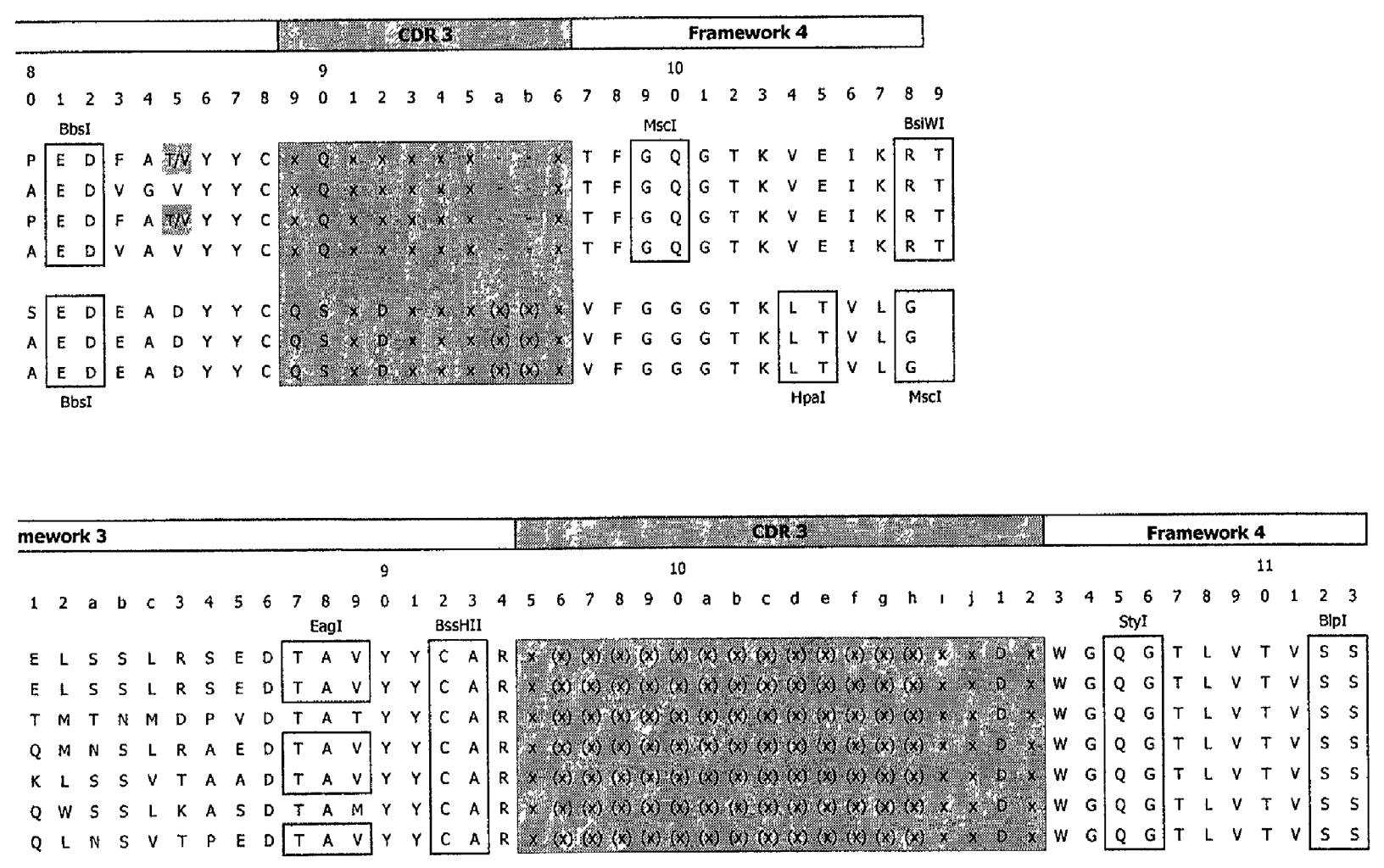

FIG. 1. Protein sequences encoded by the HuCAL® $V_H$ and $V_L$ Fab master genes. Seven $V_H$ and $V_L$ sequences are aligned, and the approximate location of restriction endonuclease sites introduced into the corresponding DNA sequences are indicated. The numbering is according to VBASE except for the gap in V1 position 9. In VBASE the gap is set at position 10. See also Chothia et al. (1992) *J. Mol. Biol.* 227, 776–798, Tomlinson et al. (1995) *EMBO J.* 14, 4628–4638 and Williams et al. (1996) *J. Mol. Biol.* 264, 220–232).

Figure 2:
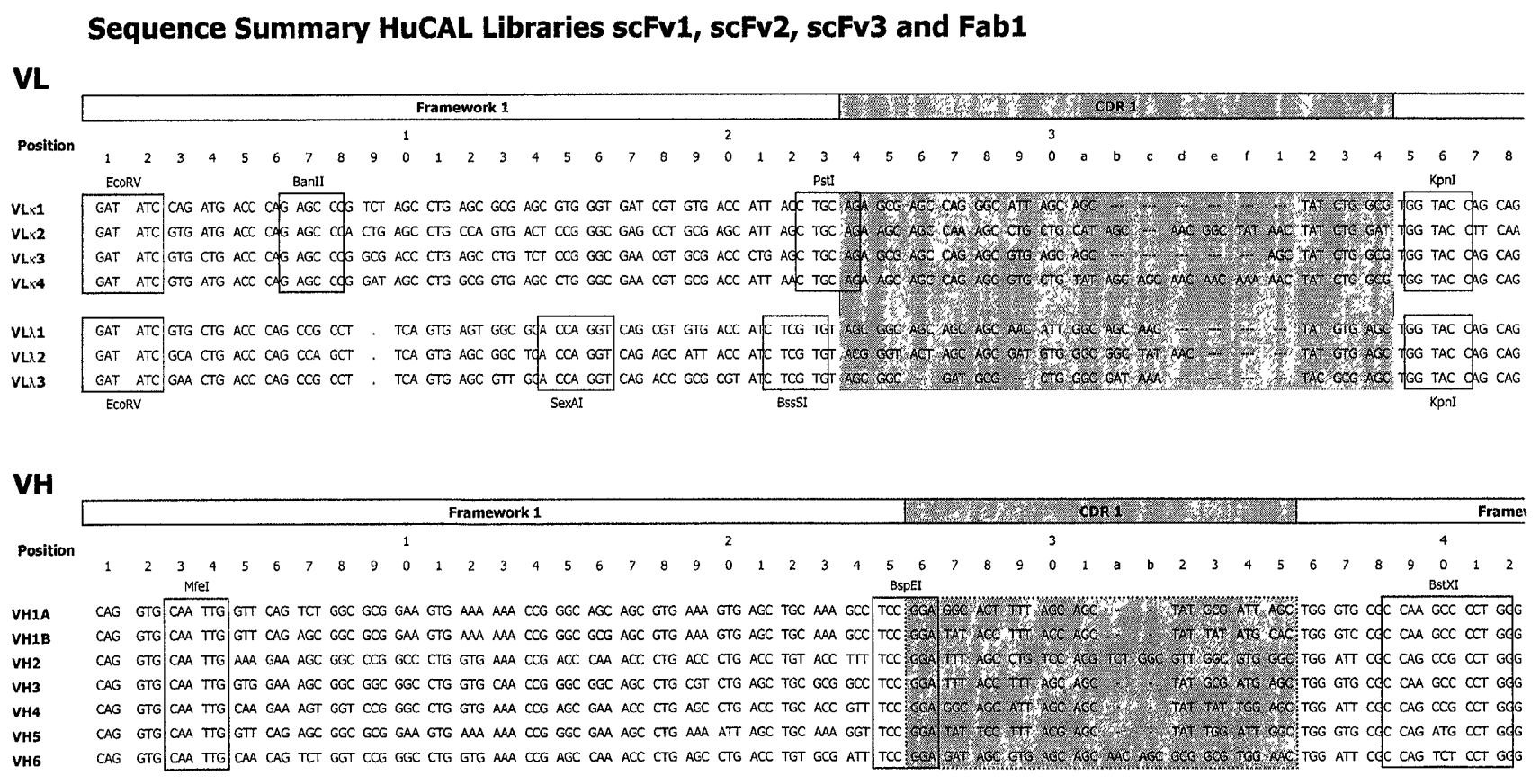
Figure 2:
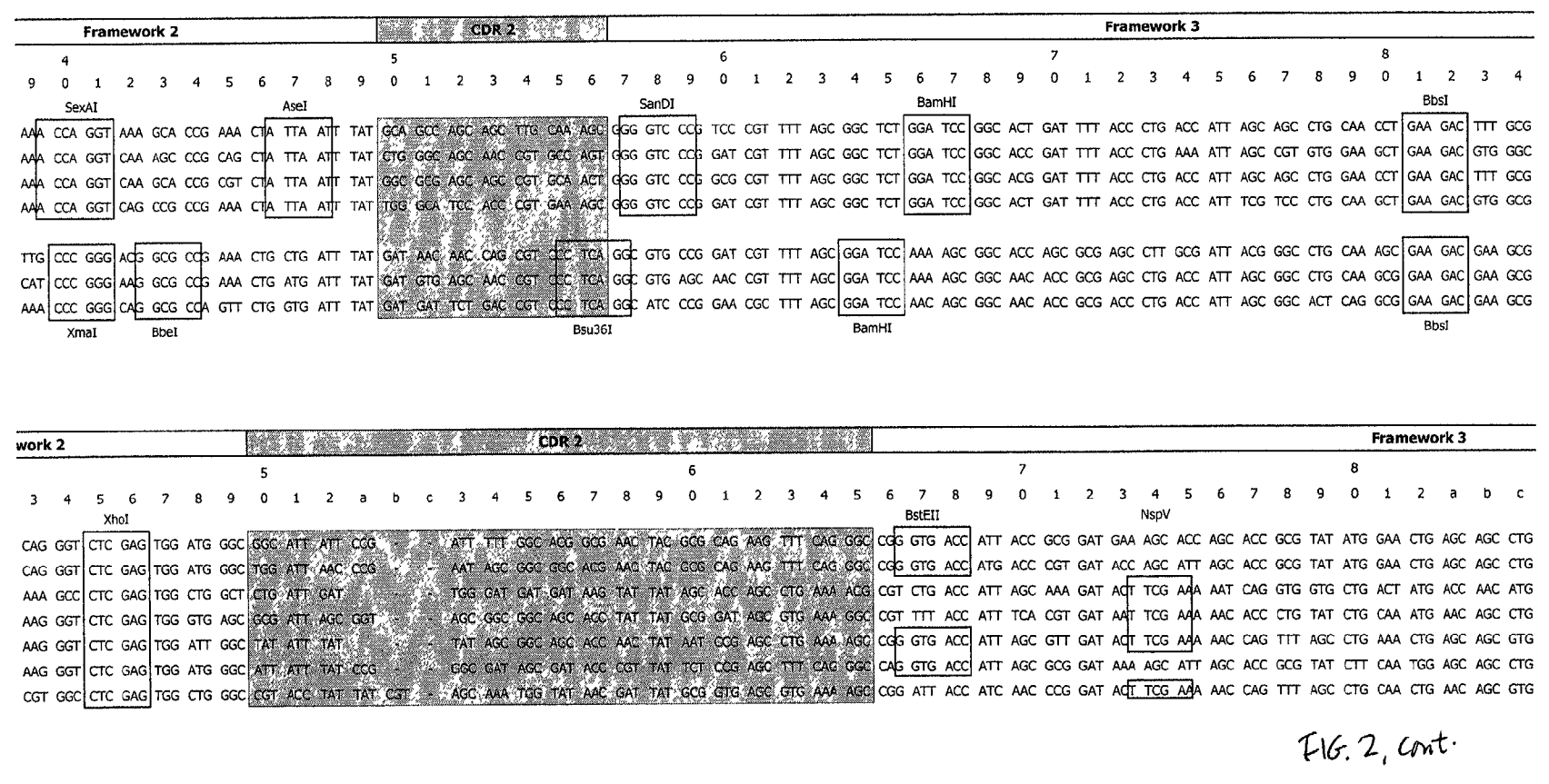

FIG. 2. Nucleotide sequences of the HuCAL® $V_H$ and $V_L$ Fab master genes.

FIG. 5. Sequence comparison between human and rat TIMP-1. Sequence regions in bold were used for peptide synthesis. Residues that make stronger direct contacts with MMP-3 are italicized, and residues that make weaker direct contacts with MMP-3 are underlined (Gomis-Ruth et al., 1997).

DETAILED DESCRIPTION OF THE INVENTION

Figure 3:
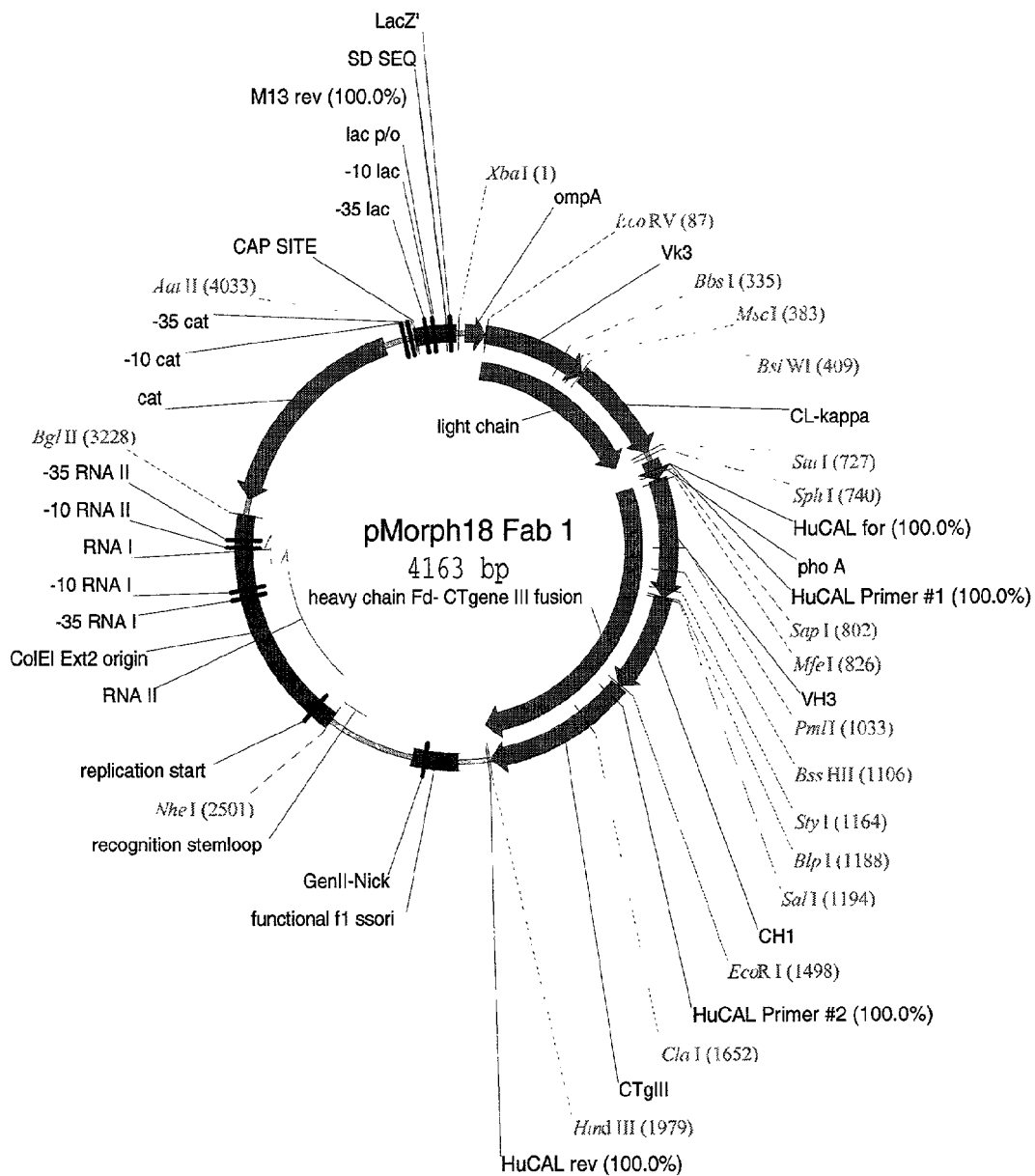
FIG. 3. Fab display vector pMORPH® 18 Fab 1.

The invention provides human antibodies that bind to TIMP-1. These antibodies are useful for a variety of therapeutic and diagnostic purposes.

Characteristics of Human TIMP-1 Antibodies

"Antibody" as used herein includes intact immunoglobulin molecules (e.g., IgG$_1$, IgG$_{2a}$, IgG$_{2b}$, IgG$_3$, IgM, IgD, IgE, IgA), as well as fragments thereof, such as Fab, F(ab')2, scFv, and Fv, which are capable of specific binding to an epitope of a human and/or rat TIMP-1 protein. Antibodies that specifically bind to TIMP-1 provide a detection signal at least 5-, 10-, or 20-fold higher than a detection signal provided with other proteins when used in an immunochemical assay. Preferably, antibodies that specifically bind to human and/or rat TIMP-1 do not detect other proteins in immunochemical assays and can immunoprecipitate the TIMP-1 from solution.

The K$_d$ of human antibody binding to TIMP-1 can be assayed using any method known in the art, including technologies such as real-time Bimolecular Interaction Analysis (BIA) (Sjolander & Urbaniczky, Anal. Chem. 63, 2338–45, 1991, and Szabo et al., Curr. Opin. Struct. Biol. 5, 699–705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In a BIAcore™ assay, some human antibodies of the invention specifically bind to human TIMP-1 with a K$_d$ of about 0.1 nM to about 10 μM, about 2 nM to about 1 μM, about 2 nM to about 200 nM, about 2 nM to about 150 nM, about 50 nM to about 100 nM, about 0.2 nM to about 13 nM, about 0.2 nM to about 0.5 nM, about 2 nM to about 13 nM, and about 0.5 nM to about 2 nM. More preferred human antibodies specifically bind to human TIMP-1 with a K$_d$ selected from the group consisting of about 0.2 nM, about 0.3 nM, about 0.5 M, about 0.6 nM, about 2 nM, about 7 nM, about 10 nM, about 11 nM, and about 13 nM.

Other human antibodies of the invention specifically bind to rat TIMP-1 with a K$_d$ of about 0.1 nM to about 10 μM, about 2 nM to about 1 μM, about 2 nM to about 200 nM, about 2 nM to about 150 nM, about 50 nM to about 100 nM, about 1.3 nM to about 13 nM, about 1.8 nM to about 10 nM, about 2 nM to about 9 nM, about 1.3 nM to about 9 nM, and about 2 nM to about 10 nM. Preferred $K_d$s range from about 0.8 nM, about 1 nM, about 1.3 nM, about 1.9 nM, about 2 nM, about 3 nM, about 9 nM, about 10 nM, about 13 nM, about 14 nM, and about 15 nM.

Preferably, antibodies of the invention neutralize an MMP-inhibiting activity of the TIMP-1. The MMP can be, for example, MMP-1, MMP-2, MMP-3, MMP-7, MMP-8, MMP-9, MMP-10, MMP-11, MMP-12, MMP-13, MMP-19, MMP-20 or MMP-23.

$IC_{50}$ for neutralizing MMP-inhibiting activity of TIMP-1 can be measured by any means known in the art. Preferably, $IC_{50}$ is determined using the high throughput fluorogenic assay described in Bickett et al., *Anal. Biochem.* 212, 58–64, 1993. In a typical fluorogenic assay, the $IC_{50}$ of a human antibody for neutralizing human TIMP-1 MMP-inhibiting activity ranges from about 0.1 nM to about 200 nM, about 1 nM to about 100 nM, about 2 nM to about 50 nM, about 5 nM to about 25 nM, about 10 nM to about 15 nM, about 0.2 nM to about 11 nM, about 0.2 nM to about 4 nM, and about 4 nM to about 11 nM. The $IC_{50}$ for neutralizing human TIMP-1 MMP-inhibiting activity of some human antibodies is about 0.2 nM, about 0.3 nM, about 0.4 nM, about 4 nM, about 7 nM, about 9 nM, and about 11 nM.

A typical $IC_{50}$ for neutralizing rat TIMP-1 MMP-inhibiting activity ranges from about 0.1 nM to about 300 nM, about 1 nM to about 100 nM, about 2 nM to about 50 nM, about 5 nM to about 25 nM, about 10 nM to about 15 nM, about 1.1 nM to about 14 nM, about 1.6 nM to about 11 nM, about 3 nM to about 7 nM, about 1.1 nM to about 7 nM, about 1.1 nM to about 11 nM, about 3 nM to about 11 nM, and about 3 nM to about 14 nM. The $IC_{50}$ for neutralizing rat TIMP-1 MMP-inhibiting activity of some human antibodies is about 1.1 nM, about 1.6 nM, about 3 nM, about 7 nM, about 11 nM, about 14 nM, about 19 nM, about 20 nM, about 30 nM, and about 100 nM.

Preferred human antibodies of the invention are those for which the $K_d$ for binding to TIMP-1 and the $IC_{50}$ for neutralizing the MMP-inhibiting activity of the TIMP-1 are approximately equal.

A number of human antibodies having the TIMP-1 binding and MMP-inhibiting activity neutralizing characteristics described above have been identified by screening the MorphoSys HuCAL® Fab 1 library. The CDR cassettes assembled for the HuCAL® library were designed to achieve a length distribution ranging from 5 to 28 amino acid residues, covering the stretch from position 95 to 102. Knappik et al., *J Mol. Biol.* 296, 57–86, 2000. Some clones, however, had shorter VHCDR3 regions. In fact, it is a striking feature of anti-human TIMP-1 human antibodies identified from this library that they all exhibit the combination VH312 and a relatively short VHCDR3 region, typically four amino acids.

In some embodiments of the invention, the VHCDR3 region of a human antibody has an amino acid sequence shown in SEQ ID NOS:1–43. In other embodiments of the invention, the VLCDR3 region of a human antibody has an amino acid sequence shown in SEQ ID NOS:44–86. See Tables 2, 3, and 7. Human antibodies which have TIMP-1 binding and MMP-inhibiting activity neutralizing characteristics of antibodies such as those described above and in Tables 2, 3, and 7 also are human antibodies of the invention.

Obtaining Human Antibodies

Human antibodies with the TIMP-1 binding and MMP-activity neutralizing characteristics described above can be identified from the MorphoSys HuCAL® library as follows. Human or rat TIMP-1, for example, is coated on a microtiter plate and incubated with the MorphoSys HuCAL® Fab phage library (see Example 1, below). Those phage-linked Fabs not binding to TIMP-1 can be washed away from the plate, leaving only phage which tightly bind to TIMP-1. The bound phage can be eluted, for example, by a change in pH or by elution with *E. coli* and amplified by infection of *E. coli* hosts. This panning process can be repeated once or twice to enrich for a population of antibodies that tightly bind to TIMP-1. The Fabs from the enriched pool are then expressed, purified, and screened in an ELISA assay. The identified hits are then screened in the enzymatic assay described in Bickett et al., 1993, and Bodden et al., 1994. Those Fabs that lead to the degradation of the peptide are likely the ones which bind to TIMP-1, thereby blocking its interaction to MMP-1.

The initial panning of the HuCAL® Fab 1 library also can be performed with TIMP-1 as the antigen in round one, followed in round 2 by TIMP-1 peptides fused to carrier proteins, such as BSA or transferrin, and in round 3 by TIMP-1 again. Human TIMP-1 peptides which can be used for panning include human TIMP-1 residues 2–12 (TCVPPHPQTAF, SEQ ID NO:87; CTSVPPHPQTAF, SEQ ID NO:88; STCVPPHPQTAF, SEQ ID NO:89; STSVPPHPQTAFC, SEQ ID NO:90), 28–36 (CEVNQTTLYQ, SEQ ID NO:91), 64–75 (PAMESVCGYFHR, SEQ ID NO:92), 64–79 (PAMESVCGYFHRSHNR, SEQ ID NO:93; CPAMESVSGYFHRSHNR, SEQ ID NO:94; PAMESVSGYFHRSHNRC, SEQ ID NO:95), and 145–157 (CLWTDQLLQGSE, SEQ ID NO:96). These peptide sequences are selected from regions of human TIMP-1 that are predicted to interact with MMPs. See Gomis-Ruth et al., *Nature* 389, 77–81, 1997. Directing Fabs toward the MMP-interacting region of human TIMP-1 in round 2 should increase the chance of identifying Fabs that can block the ability of human TIMP-1 to inhibit human MMP-1 activity.

Another method that can be used to improve the likelihood of isolating neutralizing Fabs is the panning on human TIMP-1 and eluting the binding Fabs with human MMP-1. This strategy should yield higher affinity antibodies than would otherwise be obtained.

Details of the screening process are described in the specific examples, below. Other selection methods for highly active specific antibodies or antibody fragments can be envisioned by those skilled in the art and used to identify human TIMP-1 antibodies.

Human antibodies with the characteristics described above also can be purified from any cell that expresses the antibodies, including host cells that have been transfected with antibody-encoding expression constructs. The host cells are cultured under conditions whereby the human antibodies are expressed. A purified human antibody is separated from other compounds that normally associate with the antibody in the cell, such as certain proteins, carbohydrates, or lipids, using methods well known in the art. Such methods include, but are not limited to, size exclusion chromatography, ammonium sulfate fractionation, ion exchange chromatography, affinity chromatography, and preparative gel electrophoresis. A preparation of purified human antibodies is at least 80% pure; preferably, the preparations are 90%, 95%, or 99% pure. Purity of the preparations can be assessed by any means known in the art, such as SDS-polyacrylamide gel electrophoresis. A preparation of purified human antibodies of the invention can contain more than one type of human antibody with the TIMP-1 binding and neutralizing characteristics described above.

Alternatively, human antibodies can be produced using chemical methods to synthesize its amino acid sequence, such as by direct peptide synthesis using solid-phase techniques (Merrifield, *J. Am. Chem. Soc.* 85, 2149–54, 1963; Roberge et al., *Science* 269, 202–04, 1995). Protein synthesis can be performed using manual techniques or by automation. Automated synthesis can be achieved, for example, using Applied Biosystems 431A Peptide Synthesizer (Perkin Elmer). Optionally, fragments of human antibodies can be separately synthesized and combined using chemical methods to produce a full-length molecule.

The newly synthesized molecules can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic polypeptide can be confirmed by amino acid analysis or sequencing (e.g., using Edman degradation).

Assessment of Therapeutic Utility of Human Antibodies

To assess the ability of a particular antibody to be therapeutically useful to treat, liver fibrosis, for example, the antibody can be tested in vivo in a rat liver fibrosis model. Thus, preferred human antibodies of the invention are able to block both human and rat TIMP-1 activity. If desired, human Fab TIMP-1 antibodies can be converted into full immunoglobulins, for example $IgG_1$ antibodies, before therapeutic assessment. This conversion is described in Example 5, below.

To identify antibodies that cross-react with human and rat TIMP-1, an ELISA can be carried out using rat TIMP-1. Functional cross-reactivity can be confirmed in an enzymatic assay, as described in Bickett et al., *Anal. Biochem.* 212, 58–64, 1993. The assay uses human or rat TIMP-1, human MMP-1 or rat MMP-13 (the rat counterpart of human MMP-1), and a synthetic fluorogenic peptide substrate. Enzyme activity of uncomplexed MMP-1 (or MMP-13) is assessed by observing an increase in a fluorescence signal.

Antibodies that block human and/or rat TIMP-1 activity can be screened in an ELISA assay that detects the decrease of TIMP-1/MMP-1 complex formation in cultures of HepG2 cells. Antibodies that meet this criteria can then be tested in a rat liver fibrosis model to assess therapeutic efficacy and correlate this efficacy with the ability of the antibodies to block TIMP-1 inhibition of MMP-1 in vitro.

Antibodies that demonstrate therapeutic efficacy in the rat liver fibrosis model can then be tested for binding to and blockade of TIMP-2,-3, and -4 in an in vitro enzymatic assay. Blocking the minimum number of TIMPs necessary for efficacy in liver fibrosis or other TIMP-associated pathology is preferable to minimize potential side effects.

Polynucleotides Encoding Human TIMP-1 Antibodies

The invention also provides polynucleotides encoding human TIMP-1 antibodies. These polynucleotides can be used, for example, to produce quantities of the antibodies for therapeutic or diagnostic use.

Polynucleotides that can be used to encode the VHCDR3 regions shown in SEQ ID NOS: 1–43 are shown in SEQ ID NOS:226–268, respectively. Polynucleotides that can be used to encode the VLCDR3 region shown in SEQ ID NOS:44–86 are shown in SEQ ID NOS: 183–225, respectively. Polynucleotides that encode heavy chains (SEQ ID NOS:140–182) and light chains (SEQ ID NOS:97–139) of human antibodies of the invention that have been isolated from the MorphoSys HuCAL® library are shown in SEQ ID NOS:269–311 and SEQ ID NOS:312–354, respectively.

Polynucleotides of the invention present in a host cell can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated polynucleotides encoding antibodies of the invention. For example, restriction enzymes and probes can be used to isolate polynucleotides which encode the antibodies. Isolated polynucleotides are in preparations that are free or at least 70, 80, or 90% free of other molecules.

Human antibody-encoding DNA molecules of the invention can be made with standard molecular biology techniques, using mRNA as a template. Thereafter, DNA molecules can be replicated using molecular biology techniques known in the art and disclosed in manuals such as Sambrook et al. (1989). An amplification technique, such as PCR, can be used to obtain additional copies of the polynucleotides.

Alternatively, synthetic chemistry techniques can be used to synthesize polynucleotides encoding antibodies of the invention. The degeneracy of the genetic code allows alternate nucleotide sequences to be synthesized that will encode an antibody having, for example, one of the VHCDR3, VLCDR3, light chain, or heavy chain amino acid sequences shown in SEQ ID NOS:1–43, 44–86, 97–139, or 140–182, respectively.

Expression of Polynucleotides

To express a polynucleotide encoding a human antibody of the invention, the polynucleotide can be inserted into an expression vector that contains the necessary elements for the transcription and translation of the inserted coding sequence. Methods that are well known to those skilled in the art can be used to construct expression vectors containing sequences encoding human antibodies and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1995. See also Examples 1–3, below.

A variety of expression vector/host systems can be utilized to contain and express sequences encoding a human antibody of the invention. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUE- SCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a human antibody, vectors based on SV40 or EBV can be used with an appropriate selectable marker.

Large scale production of human TIMP-1 antibodies can be carried out using methods such as those described in Wurm et al., *Ann. N.Y. Acad. Sci.* 782, 70–78, 1996, and Kim et al., *Biotechnol. Bioengineer.* 58, 73–84, 1998.

Pharmaceutical Compositions

Any of the human TIMP-1 antibodies described above can be provided in a pharmaceutical composition comprising a pharmaceutically acceptable carrier. The pharmaceutically acceptable carrier preferably is non-pyrogenic. The compositions can be administered alone or in combination with at least one other agent, such as stabilizing compound, which can be administered in any sterile, biocompatible pharmaceutical carrier, including, but not limited to, saline, buffered saline, dextrose, and water. A variety of aqueous carriers may be employed, e.g., 0.4% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected. See U.S. Pat. No. 5,851,525. If desired, more than one type of human antibody, for example with different $K_d$ for TIMP-1 binding or with different $IC_{50}$s for MMP-inhibiting activity neutralization, can be included in a pharmaceutical composition.

The compositions can be administered to a patient alone, or in combination with other agents, drugs or hormones. In addition to the active ingredients, these pharmaceutical compositions can contain suitable pharmaceutically-acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means.

After pharmaceutical compositions have been prepared, they can be placed in an appropriate container and labeled for treatment of an indicated condition. Such labeling would include amount, frequency, and method of administration.

Methods of Decreasing MMP-Inhibiting Activity of Human TIMP-1

The invention provides methods of decreasing an MMP-inhibiting activity of human or rat TIMP-1. Such methods can be used therapeutically, as described below, or in a research setting. Thus, the methods can be carried out in a cell-free system, in a cell culture system, or in vivo. In vivo methods of decreasing MMP-inhibiting activity of human or rat TIMP-1 are described below.

Human TIMP-1 is contacted with a human antibody that binds to the human TIMP-1, thereby decreasing the MMP-inhibiting activity of the human TIMP-1 relative to human TIMP-1 activity in the absence of the antibody. The antibody can be added directly to the cell-free system, cell culture system, or to an animal subject or patient, or can be provided by means of an expression vector encoding the antibody.

Diagnostic Methods

The invention also provides diagnostic methods, with which human or rat TIMP-1 can be detected in a test preparation, including without limitation a sample of serum, lung, liver, heart, kidney, colon, a cell culture system, or a cell-free system (e.g., a tissue homogenate). Such diagnostic methods can be used, for example, to diagnose disorders in which TIMP-1 is elevated. Such disorders include, but are not limited to, liver fibrosis, alcoholic liver disease, cardiac fibrosis, acute cardiac syndrome, lupus nephritis, glomerulosclerotic renal disease, benign prostate hypertrophy, lung cancer, colon cancer, and idiopathic pulmonary fibrosis. When used for diagnosis, detection of an amount of the antibody-TIMP-1 complex in a test sample from a patient which is greater than an amount of the complex in a normal sample identifies the patient as likely to have the disorder.

The test preparation is contacted with a human antibody of the invention, and the test preparation is then assayed for the presence of an antibody-TIMP-1 complex. If desired, the human antibody can comprise a detectable label, such as a fluorescent, radioisotopic, chemiluminescent, or enzymatic label, such as horseradish peroxidase, alkaline phosphatase, or luciferase.

Optionally, the antibody can be bound to a solid support, which can accommodate automation of the assay. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the antibody to the solid support, including use of covalent and non-covalent linkages, passive absorption, or pairs of binding moieties attached to the antibody and the solid support. Binding of TIMP-1 and the antibody can be accomplished in any vessel suitable for containing the reactants. Examples of such vessels include microtiter plates, test tubes, and microcentrifuge tubes.

Therapeutic Methods

The invention also provides methods of ameliorating symptoms of a disorder in which TIMP-1 is elevated. These disorders include, without limitation, liver fibrosis alcoholic liver disease, cardiac fibrosis, acute coronary syndrome, lupus nephritis, glomerulosclerotic renal disease, idiopathic pulmonary fibrosis, benign prostate hypertrophy, lung cancer, colon cancer, and scarring. See, e.g., Inokubo et al., *Am. Heart J.* 141, 211–17, 2001; Ylisirnio et al., *Anticancer Res.* 20, 1311–16, 2000; Holten-Andersen et al., *Clin. Cancer Res.* 6, 4292–99, 2000; Holten-Andersen et al., *Br. J. Cancer* 80, 495–503, 1999; Peterson et al., *Cardiovascular Res.* 46, 307–15, 2000; Arthur et al., *Alcoholism: Clinical and Experimental Res.* 23, 840–43, 1999; Iredale et al., *Hepatol.* 24, 176–84, 1996.

Human antibodies of the invention are particularly useful for treating liver fibrosis. All chronic liver diseases cause the development of fibrosis in the liver. Fibrosis is a programmed uniform wound healing response. Toxic damage or injury caused by foreign proteins cause the deposition of extracellular matrix such as collagen, fibronectin, and laminin. Liver fibrosis and cirrhosis can be caused by chronic degenerative diseases of the liver such as viral hepatitis, alcohol hepatitis, autoimmune hepatitis, primary biliary cirrhosis, cystic fibrosis, hemochromatosis, Wilson's disease, and non-alcoholic steato-hepatitis, as well as chemical damage.

Altered degradation and synthesis of extracellular matrix (particularly collagens) play central roles in pathogenesis of liver fibrosis. In the early phases, hepatic stellate cells (HSC) are initially activated and release matrix metalloproteases with the ability to degrade the normal liver matrix. When HSC are fully activated, there is a net down-regulation of matrix degradation mediated by increased synthesis and extracellular release of tissue inhibitors of metalloprotease (TIMP)-1 and -2. The dynamic regulation of activity of metalloproteases during liver fibrosis makes them and their inhibitors targets for therapeutic intervention.

Human antibodies of the invention are also particularly useful for treating lung fibrosis. Lung airway fibrosis is a hallmark of airway remodeling in patients with chronic asthma, so human antibodies of the invention are also particularly useful for chronic asthma. Airway remodeling is a well-recognized feature in patients with chronic asthma. TIMP-1 but not TIMP-2 levels were significantly higher in untreated asthmatic subjects than in glucocorticoid-treated subjects or controls (p<0.0001), and were far greater than those of MMP-1, MMP-2, MMP-3, and MMP-9 combined (Mautino et al., Am J Respir Crit Care Med 1999 160: 324–330). TIMP-1 mRNA and protein expression are selectively and markedly increased in a murine model of bleomycin-induced pulmonary fibrosis (Am. J. Respir. Cell Mol. Biol. 24:599–607, 2001). This specific elevation of TIMP-1 without increase in MMPs in asthma patients suggests that inhibition of TIMP-1 by an antibody can restore normal collagen degradation in the lung.

Human antibodies of the invention are also particularly useful for treating cancer. TIMP-1 protein has been found to be elevated in plasma of colon (Holten-Andersen et al., Br J Cancer 1999, 80:495–503) and prostate (Jung et al., Int J Cancer, 1997, 74:220–223) cancer patients, and high TIMP-1 plasma level correlates with poor clinical outcome of colon cancer (Holten-Andersen et al., Clin Cancer Res 2000 6:4292–4299). TIMP-1 induces dose-dependent proliferation of breast tumorigenic clonal cell line and tyrosine phosphorylation (Luparello et al, Breast Cancer Res Treat, 1999, 54:235–244). Therefore, the use of antibody against TIMP-1 may block its ability to induce cancer.

Human TIMP-1 antibodies can be used to prevent or diminish scar formation, such as scar formation after surgery (particularly ophthalmic surgery) or injury (such as a burn, scrape, crush, cut or tear injury).

In one embodiment of the invention, a therapeutically effective dose of a human antibody of the invention is administered to a patient having a disorder in which TIMP-1 is elevated, such as those disorders described above. Symptoms of the disorder, including deposition of extracellular matrix, as well as loss of tissue or organ function, are thereby ameliorated.

Determination of a Therapeutically Effective Dose

The determination of a therapeutically effective dose is well within the capability of those skilled in the art. A therapeutically effective dose refers to that amount of human antibody that reduces MMP-inhibiting activity of the TIMP-1 relative to the activity which occurs in the absence of the therapeutically effective dose.

The therapeutically effective dose can be estimated initially either in cell culture assays or in animal models, usually rats, mice, rabbits, dogs, or pigs. The animal model also can be used to determine the appropriate concentration range and route of administration. Such information can then be used to determine useful doses and routes for administration in humans. A rat liver fibrosis model is described in Example 6.

Therapeutic efficacy and toxicity, e.g., $ED_{50}$ (the dose therapeutically effective in 50% of the population) and $LD_{50}$ (the dose lethal to 50% of the population) of a human antibody, can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the patient who requires treatment. Dosage and administration are adjusted to provide sufficient levels of the human antibody or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Polynucleotides encoding human antibodies of the invention can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 mg to about 50 mg/kg, about 50 mg to about 5 mg/kg, about 100 mg to about 500 mg/kg of patient body weight, and about 200 to about 250 mg/kg of patient body weight. For administration of polynucleotides encoding the antibodies, effective in vivo dosages are in the range of about 100 ng to about 200 ng, 500 ng to about 50 mg, about 1 mg to about 2 mg, about 5 mg to about 500 mg, and about 20 mg to about 100 mg of DNA.

The mode of administration of human antibody-containing pharmaceutical compositions of the invention can be any suitable route which delivers the antibody to the host. Pharmaceutical compositions of the invention are particularly useful for parenteral administration, i.e., subcutaneous, intramuscular, intravenous, or intranasal administration.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Construction of a Human Combinatorial Antibody Library (HuCAL® Fab 1)

Cloning of HuCAL® Fab 1. HuCAL® Fab 1 is a fully synthetic, modular human antibody library in the Fab antibody fragment format. HuCAL® Fab 1 was assembled starting from an antibody library in the single-chain format (HuCAL® -scFv; Knappik et al., *J. Mol Biol.* 296, 55, 2000). HuCAL® Fab 1 was cloned into a phagemid expression vector pMORPH® 18 Fab1 (FIG. 3). This vector comprises the Fd fragment with a phoA signal sequence fused at the C-terminus to a truncated gene III protein of filamentous phage, and further comprises the light chain VL-CL with an ompA signal sequence. Both chains are under the control of the lac operon. The constant domains Cλ, Cκ, and CH are synthetic genes fully compatible with the modular system of HuCAL® (Knappik et al., 2000).

First, the Vλ and Vκ libraries were isolated from HuCAL®-scFv. Vλ1 fragments were amplified by 15 PCR cycles (Pwo polymerase) with primers 5'-GTGGTGGTTC-CGATATC-3' (SEQ ID NO:380) and 5'-AGCGTCACA-CTCGGTGCGGCTTTCGGCTGGCCAAGAACGGTTA-3' (SEQ ID NO:381). PCR-products were digested with EcoRV/DraIII and gel-purified. VLκ-chains were obtained by restriction digest with EcoRV/BsiWI and gel-purified. These Vλ and Vκ libraries were cloned into pMORPH® 18 Fab1 cut with EcoRV/DraIII and EcoRV/BsiWI, respectively. After ligation and transformation in *E. coli* TG-1, library sizes of $4.14 \times 10^8$ and $1.6 \times 10^8$, respectively, were obtained, in both cases exceeding the Vλ diversity of HuCAL®-scFv.

Similarly, the VH library was isolated from HuCAL®-scFv by restriction digest using StyI/MunI. This VH library was cloned into the pMORPH® 18-Vλ and Vκ libraries cut with StyI/MunI. After ligation and transformation in *E. coli* TG-1, a total library size of $2.09 \times 10^{10}$ was obtained, with 67% correct clones (as identified by sequencing of 207 clones).

Phagemid rescue, phage amplification and purification. HuCAL® Fab was amplified in 2×TY medium containing 34 μg/ml chloramphenicol and 1% glucose (2×TY-CG). After helper phage infection (VCSM13) at 37° C. at an $OD_{600}$ of about 0.5, centrifugation and resuspension in 2×TY/ 34 μg/ml chloramphenicol/50 μg/ml kanamycin, cells were grown overnight at 30° C. Phage were PEG-precipitated from the supernatant (Ausubel et al., 1998), resuspended in PBS/20% glycerol, and stored at −80° C. Phage amplification between two panning rounds was conducted as follows: mid-log phase TG1-cells were infected with eluted phage and plated onto LB-agar supplemented with 1% of glucose and 34 μg/ml of chloramphenicol. After overnight incubation at 30° C., colonies were scraped off and adjusted to an $OD_{600}$ of 0.5. Helper phage were added as described above.

EXAMPLE 2

Solid Phase Panning

Wells of MaxiSorp™ microtiter plates (Nunc) were coated with rat- or human TIMP protein diluted to 50 μg/ml dissolved in PBS (2 μg/well). After blocking with 5% non-fat dried milk in PBS, $1–5 \times 10^{12}$ HuCAL® Fab phage purified as above were added for 1 h at 20° C. After several washing steps, bound phage were eluted by pH-elution with 100 mM triethylamine and subsequent neutralization with 1M TRIS-Cl pH 7.0. See Krebs et al., *J. Immunol. Meth.* 254, 67, 2001. Two to three rounds of panning were performed with phage amplification conducted between each round as described above.

EXAMPLE 3

Solution Panning

Biotinylated antigen was diluted to 40 nM in PBS, 1013 HuCAL®-Fab 1 phage were added and incubated for 1 h at 20° C. Phage-antigen complexes were captured on Neutravidin plates (Pierce). After several washing steps, bound phages were eluted by different methods (Krebs et al., 2001). Two rounds of panning were routinely performed.

EXAMPLE 4

Subcloning of Selected Fab Fragments for Expression

Figure 4:
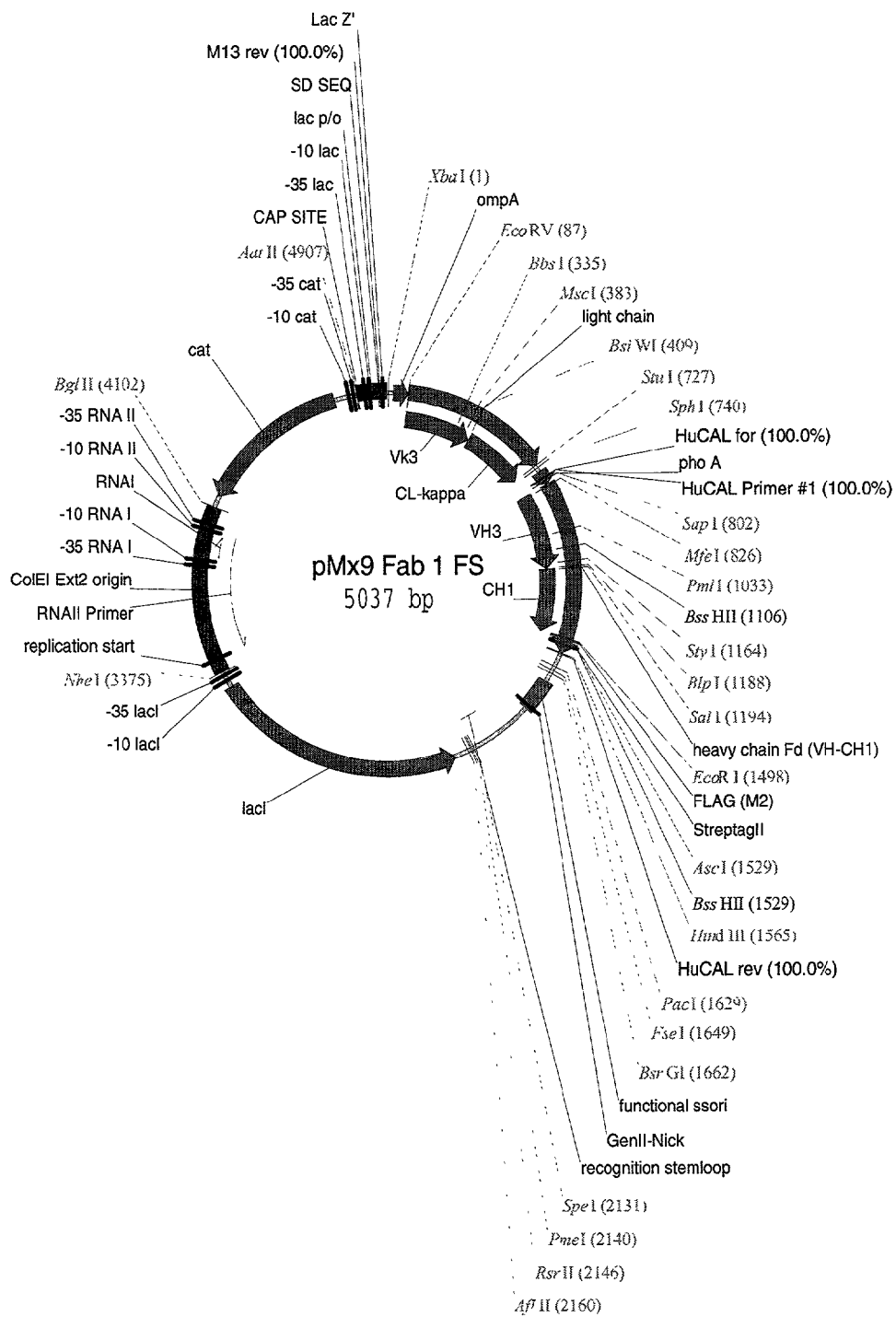
FIG. 4. Vector map of pMORPH® x9Fab1_FS.
Figure 6:
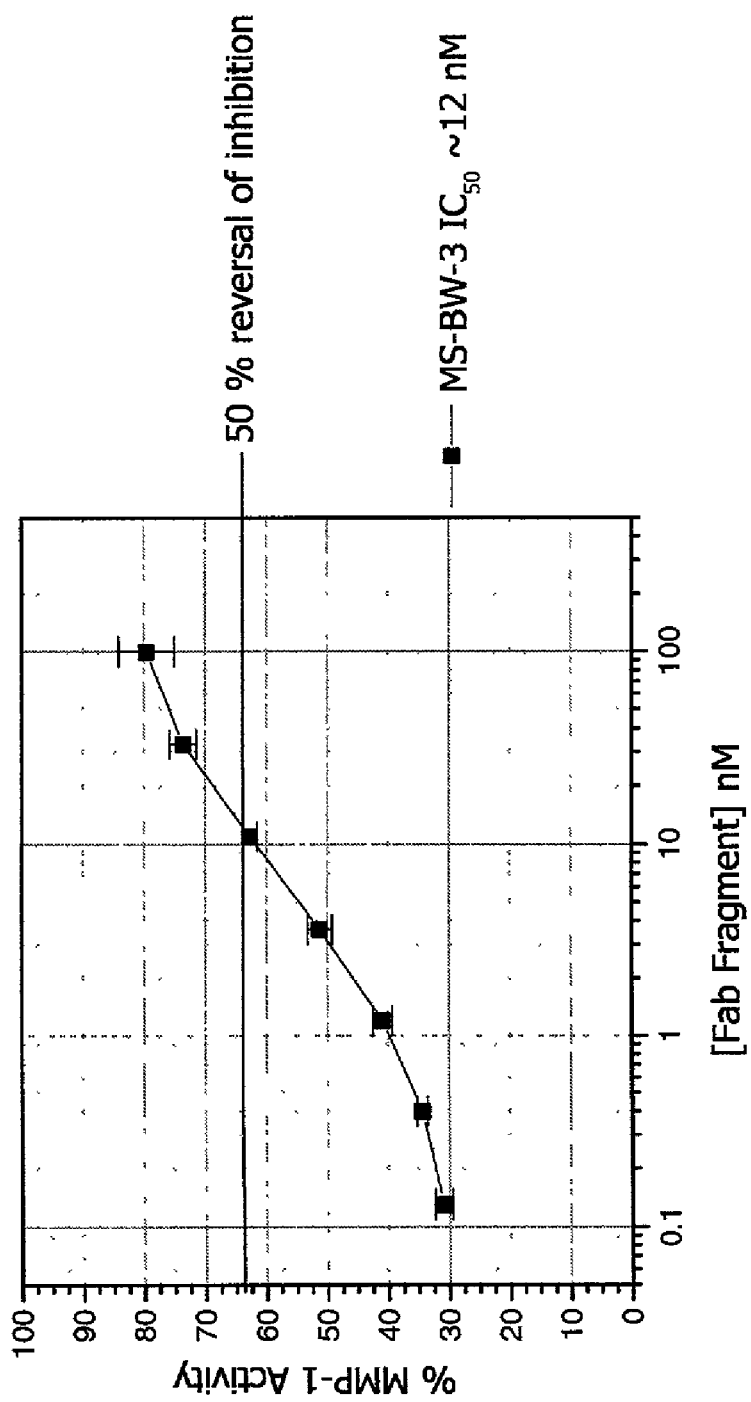
FIG. 6. Activity of MS-BW-3 in human TIMP-1/MMP-1 assay. Antibody Fab fragments were diluted in triplicate to the indicated concentrations in assay buffer containing 0.05% BSA. After addition of TIMP (final conc. 1.2 nM), MMP (final conc. 1.2 nM), and peptide substrate (final conc. 50 µM) and incubation for 1–3 h at 37° C. fluorescence at Ex320 nm/Em 430 nm was measured. IC$_{50}$ was calculated as outlined in material and methods section, using 100% MMP-1 activity (in absence of TIMP-1) and 27% MMP-1 activity (in absence of antibody) as reference values.

The Fab-encoding inserts of the selected HuCAL® Fab 1 fragments were subcloned into the expression vector pMORPH® x7_FS (Knappik et al., *J. Mol. Biol.* 296, 55, 2000) to facilitate rapid expression of soluble Fab. The DNA preparation of the selected HuCAL® Fab 1 clones was digested with XbaI/EcoRI, thus cutting out the Fab encoding insert (ompA-VL and phoA-Fd). Subcloning of the purified inserts into the XbaI/EcoRI cut vector PMORPH® x7, previously carrying a scFv insert, produces a Fab expression vector designated pMORPH® x9_Fab1_FS (FIG. 4). Fabs expressed in this vector carry two C-terminal tags (FLAG™ and Strep-tagII) for detection and purification.

EXAMPLE 5

Identification of TIMP-Binding Fab Fragments by ELISA

The wells of 384-well Maxisorp ELISA plates were coated with 20 μl/well solutions of rat TIMP or human TIMP at a concentration of 5 μg/ml diluted in coating buffer. Expression of individual Fab in *E. coli* TG-1 from expression vector pMORPH® x9_FS was induced with 0.5 mM IPTG for 12 h at 30° C. Soluble Fab was extracted from the periplasm by osmotic shock (Ausubel et al., 1998) and used in an ELISA. The Fab fragment was detected after incubation with alkaline phosphatase-conjugated anti-Fab antibody (Dianova), followed by development with Attophos substrate (Roche) and measurement at Ex450 nm/Em535 nm. Values at 370 nm were read out after addition of horseradish peroxidase-conjugated anti-mouse IgG antibody and POD soluble substrate (Roche Diagnostics).

EXAMPLE 6

Expression and Purification of HuCAL®-Fab 1 Antibodies in *E. coli*

Expression of Fab fragments encoded by pMORPH® x9_FS in TG-1 cells was carried out in shaker flask cultures with 1 liter of 2×TY medium supplemented with 34 μg/ml chloramphenicol. After induction with 0.5 mM IPTG, cells were grown at 22° C. for 16 h. Periplasmic extracts of cell pellets were prepared, and Fab fragments were isolated by Strep-tactin® chromatography (IBA, Goettingen, Germany). The apparent molecular weights were determined by size exclusion chromatography (SEC) with calibration standards. Concentrations were determined by UV-spectrophotometry.

EXAMPLE 7

Construction of HuCAL® Immunoglobulin Expression Vectors

Heavy chain cloning. The multiple cloning site of pcDNA3.1+ (Invitrogen) was removed (NheI/ApaI), and a stuffer compatible with the restriction sites used for HuCAL® design was inserted for the ligation of the leader sequences (NheI/EcoRI), VH-domains (EcoRI/BlpI), and the immunoglobulin constant regions (BlpI/ApaI). The leader sequence (EMBL M83133) was equipped with a Kozak sequence (Kozak, 1987). The constant regions of human $IgG_1$ (PIR J00228), $IgG_4$ (EMBL K01316), and serum $IgA_1$ (EMBL J00220) were dissected into overlapping oligonucleotides with lengths of about 70 bases. Silent mutations were introduced to remove restriction sites non-compatible with the HuCAL® design. The oligonucleotides were spliced by overlap extension-PCR.

Light chain cloning. The multiple cloning site of pcDNA3.1/Zeo+ (Invitrogen) was replaced by two different stuffers. The κ-stuffer provided restriction sites for insertion of a κ-leader (NheI/EcoRV), HuCAL®-scFv Vκ-domains (EcoRV/BsiWI,) and the κ-chain constant region (BsiWI/ApaI). The corresponding restriction sites in the λ-stuffer were NheI/EcoRV (λ-leader), EcoRV/HpaI (Vλ-domains), and HpaI/ApaI (λ-chain constant region). The κ-leader (EMBL Z00022) as well as the λ-leader (EMBL L27692) were both equipped with Kozak sequences. The constant regions of the human κ-(EMBL J00241) and λ-chain (EMBL M18645) were assembled by overlap extension-PCR as described above.

Generation of IgG-expressing CHO-cells. CHO-K1 cells were co-transfected with an equimolar mixture of IgG heavy and light chain expression vectors. Double-resistant transfectants were selected with 600 μg/ml G418 and 300 μg/ml Zeocin (Invitrogen) followed by limiting dilution. The supernatant of single clones was assessed for IgG expression by capture-ELISA (see below). Positive clones were expanded in RPMI-1640 medium supplemented with 10% ultra-low IgG-FCS (Life Technologies). After adjusting the pH of the supernatant to 8.0 and sterile filtration, the solution was subjected to standard protein A column chromatography (Poros 20 A, PE Biosystems).

EXAMPLE 8

Design of the CDR3 Libraries

Vλ positions 1 and 2. The original HuCAL® master genes were constructed with their authentic N-termini: Vλ11: QS (CAGAGC), Vλ2: QS (CAGAGC), and Vλ13: SY (AGCTAT). Sequences containing these amino acids are shown in WO 97/08320. During HuCAL® library construction, the first two amino acids were changed to DI to facilitate library cloning (EcoRI site). All HuCAL® libraries contain Vλ1 genes with the EcoRV site GATATC (DI) at the 5'-end. All HuCAL® kappa genes (master genes and all genes in the library) contain DI at the 5'-end.

VH position 1. The original HuCAL® master genes were constructed with their authentic N-termini: VH1A, VH1B, VH2, VH4, and VH6 with Q (=CAG) as the first amino acid and VH3 and VH5 with E (=GAA) as the first amino acid. Sequences containing these amino acids are shown in WO 97/08320. In the HuCAL® Fab 1 library, all VH chains contain Q (=CAG) at the first position.

Vκ1/Vκ3 position 85. Because of the cassette mutagenesis procedure used to introduce the CDR3 library (Knappik et al., *J. Mol. Biol.* 296, 57–86, 2000), position 85 of Vκ1 and Vκ3 can be either T or V. Thus, during HuCAL® scFv 1 library construction, position 85 of Vκ1 and Vκ3 was varied as follows: Vκ1 original, 85T (codon ACC); Vκ1 library, 85T or 85V (TRIM codons ACT or GTT); Vκ3 original, 85V (codon GTG); Vκ3 library, 85T or 85V (TRIM codons ACT or GTT); the same applies to HuCAL® Fab 1.

CDR3 design. All CDR3 residues which were kept constant are indicated in FIG. 1.

CDR3 length. The designed CDR3 length distribution is as follows. Residues which were varied are shown in brackets (x) in FIG. 1. V kappa CDR3, 8 amino acid residues (position 89 to 96) (occasionally 7 residues), with Q90 fixed; V lambda CDR3, 8 to 10 amino acid residues (position 89 to 96) (occasionally 7–10 residues), with Q89, S90, and D92 fixed; and VH CDR3, 5 to 28 amino acid residues (position 95 to 102) (occasionally 4–28), with D101 fixed.

EXAMPLE 9

Chronic Carbon Tetrachloride-Induced Liver Fibrosis

Sprague Dawley rats (200–220 g) are used in an in vivo model of liver fibrosis. To maximally induce microsomal metabolism of carbon tetrachloride metabolism, animals receive 1 g/l isoniazid with their drinking water starting one week before the administration of carbon tetrachloride. Carbon tetrachloride (1:1 in mineral oil) is administered orally every fifth day at a dose of 0.2 ml/100 g body weight. A human TIMP-1 antibody is administered intravenously, either once or repeatedly, during the period of carbon tetrachloride treatment. Necropsy is performed after 5–7 weeks of treatment. McLean et al., *Br. J. Exp. Pathol.* 50, 502–06, 1969.

Transverse cylinders of liver tissue are cut from the right liver lobe, fixed in formaldehyde, and embedded in paraffin. The amount of fibrosis in the liver is indicated by the picrosirius red-stained fibrotic areas. Picrosirius-positive areas are determined in several centrilobular fields in each section. Parameters of color detection are standardized and kept constant throughout the experiment. The field are selected using a standardized grid which covers an area of 31 mm2. A Leica Quantimed 500 MC system is used for morphometry.

EXAMPLE 10

Hydroxyproline Determination

The method of Prockop & Udenfried, *Anal. Biochem.* 1, 228–39, 1960, can be used to determine hydroxyproline is liver tissues, with the following modifications. Liver specimens of 60–90 mg wet weight are dried and hydrolyzed in 6 N HCl at 100° C. for 17 h. The hydrolyzed material is dried and reconstituted in 5 ml of deionized water. Two hundred microliters of this hydrolysate are mixed with 200 ml of ethanol and 200 ml chloramin T solution (0.7% in citrate buffer [5.7 g sodium acetate, 3.75 g trisodium citrate, 0.55 g citric acid, 38.5 ml ethanol, made up to 100 ml with water]) and allowed to oxidize for 20 min at room temperature. Four hundred microliters of Ehrlich's reagent (12 g p-dimethylaminobenzldehyde in 40 ml ethanol and 2.7 ml $H_2SO_4$) are added. After incubation for 3 h at 35° C., absorbance at 573 nm is measured.

EXAMPLE 11

Affinity Determination by Surface Plasmon Resonance Measurements (BIAcore™)

For affinity determination, monomeric fractions of affinity and SEC purified Fab fragments or purified IgG1 molecules were used. All experiments were conducted in HBS buffer at a flow rate of 20 μl/min at 25° C. on a BIAcore™ instrument. Antigens in 100 mM sodium acetate pH 5.0 were coupled to a CM 5 sensor chip using standard EDC-NHS coupling chemistry. Applying 3–4 μl of 5 μg/ml TIMP-1 typically resulted in 500 resonance units for kinetic measurements. All sensograms were fitted globally using BIA evaluation software. For monovalent Fab fragments a monovalent fit (Langmuir binding) and for IgGs a bivalent fit was applied.

EXAMPLE 12

$IC_{50}$ Determination in Human TIMP-1/Human MMP-1 and Rat TIMP-1/Rat MMP-13 Assay Purified Fab fragments or IgGs were used for $IC_{50}$ determination. Antibodies were diluted in triplicate to the indicated concentrations in assay buffer containing 0.05% BSA. After addition of TIMP (final conc. 1.2 nM or 0.4 nM for modified in human TIMP-1/human MMP-1 assay), MMP (final conc. 1.2 nM or 0.4 nM for modified in human TIMP-1/human MMP-1 assay), and peptide substrate (final conc. 50 μM) and incubation for 1–3 h at 37° C., fluorescence at Ex320 nm/Em430 nm was measured.

The following controls were included in the assay and used as reference values for $IC_{50}$ determination:
A: MMP+substrate: this value was defined as 100% MMP activity in absence of antibody and TIMP.
B: MMP+TIMP+substrate: this value was defined as maximum inhibition achieved in the assay and calculated as a % of total MMP activity.

To define the concentration of antibody that resulted in 50% reversal of inhibition ($IC_{50}$), the following procedure was used:

The value for 50% reversal of inhibition (expressed as % activity MMP) was calculated as: $Y=[(A-B)/2]+B$.
MMP activity was plotted against concentration of antibody in the assay.
The concentration of antibody that results in 50% reversal of inhibition (Y) was read on the x-axis and defined as $IC_{50}$.
Error bars in the graphs were derived from triplicate wells in one assay.

Standard deviations for $IC_{50}$ values were calculated from 3 independent assays.

EXAMPLE 13

Affinity Maturation of Selected Fab by Stepwise Exchange of CDR Cassettes

To increase affinity and biological activity of selected antibody fragments, CDR regions were optimized by cassette mutagenesis using trinucleotide directed mutagenesis (Virnekäs et al., 1994). Fab fragments in expression vector pMORPH® x9 were cloned into phagemid vector pMORPH®_18 using EcoRI/XbaI restriction sites. CDR cassettes containing several diversified positions were synthesized and cloned into Fab fragments in pMORPH® _18 using unique restriction sites (Knappik et al., 2000). Affinity maturation libraries were generated by transformation into *E. coli* TOP10F, and phage were prepared as described above. Phage displaying Fab fragments with improved affinity were selected by 2–3 rounds solution panning using stringent washing conditions (e.g., competition with 1 μM non-biotinylated antigen or washing for up to 48 h with frequent buffer exchange) and limited amounts of antigen (0.04–4 nM). Seventeen human TIMP-1 antibodies were tested for affinity to human TIMP-1 (with some tested for affinity to rat TIMP-1) using a BIAcore™ assay. The $K_d$ of these antibodies for human TIMP-1 and rat TIMP-1 are shown in Table 1.

TABLE 1

Overview of species cross-reactive Fab

| Fab | Monovalent $K_D$ human TIMP-1 | Monovalent $K_D$ rat TIMP-1 | $IC_{50}$ in human protease assay | $IC_{50}$ in rat protease assay |
|---|---|---|---|---|
| MS-BW-25 | 25 +/− 16 nM* | 4517 +/− 2400 nM | 115 +/− 15 nM | >300 nM |
| MS-BW-27 | ~74 nM | ~3200 nM | Non blocking | |
| MS-BW-21 | 520 +/− 20 nM | 36 +/− 2 nM | >300 nM | 67 +/− 5 nM |
| MS-BW-38 | ~3 nM | ~353 nM | ~11 nM | >300 nM |
| MS-BW-39 | ~7500 nM | ~108 nM | >100 nM | >100 nM |

*In cases were standard deviations are given, three independent measurements were done with Fab from three different protein expressions/purifications.
~Indicates preliminary data, in cases where measurement was done only once.

EXAMPLE 14

Screening for Fab with Improved Off-Rates by Koff Ranking using Surface Plasmon Resonance Phage eluted after solution panning were used to infect *E. coli* TG-1 and plated on agar plates containing 34 μg/ml chloramphenicol. Clones were picked into 96 well plates and used to produce Fab fragments. On the same plate, parental clones were inoculated as controls. Soluble Fab was extracted from the periplasm by osmotic shock (Ausubel et al., 1998) and used for koff ranking in BIAcore™.

All measurements were conducted in HBS buffer at a flow rate of 20 μl/min at 25° C. on a BIAcore™ instrument. Antigens in 100 mM sodium acetate pH 4.5 were coupled to a CM 5 sensor chip using standard EDC-NHS coupling chemistry. Applying 10 μl of 25 μg/ml TIMP-1 typically resulted in 5000 resonance units for koff ranking. All sensograms were fitted using BIA evaluation software. Clones with improved off rate were selected by comparison to parental clones.

EXAMPLE 15

Generation of Species Cross-Reactive Antibodies

To maximize the likelihood of obtaining blocking antibodies that are cross-reactive between human and rat TIMP-1, alternating pannings were carried out on rat and human protein. Additionally, all antibodies selected by pannings on solely the human or rat TIMP-1 protein were analyzed for cross-reactivity in order to check for cross-reactive antibodies that might be selected by chance. Antibodies selected from these pannings were analyzed for cross-reactivity in ELISA using crude *E. coli* extracts. Cross-reactive antibodies in this assay were subjected to expression in 1-liter scale followed by purification. Purified antibodies were tested for cross-reactivity in BIAcore™ and protease assays (Table 1).

As shown in Table 1, a total of five different Fab cross-reactive with human and rat TIMP-1 were generated. BIA-Core™ measurements revealed that although these antibodies clearly bind to human and rat TIMP-1, affinities for both species differ by at least a factor of 50. An antibody used for human therapy or in an animal model should have an affinity to the target protein in the low nanomolar, preferably in the sub-nanomolar range. As none of the above-described antibodies had affinities in this range for both species, these antibodies were not considered useful for further experiments or development.

EXAMPLE 16

Generation of Blocking Antibodies Against Human TIMP-1

To generate blocking antibodies against human TIMP-1, the HuCAL®-Fab 1 library was used for antibody selection (AutoPan®) on purified TIMP-1 protein followed by subcloning and expression of the selected Fab fragments in *E. coli*. Crude antibody-containing *E. coil* extracts were used for primary antibody characterization in ELISA (Auto-Screen®). Purified Fab proteins were subjected to further characterization in ELISA, TIMP-1/MMP-1 assay and BIA-core™. A total of 6100 clones were analyzed in Auto-Screen®, 670 of them showed binding to human TIMP-1.

Sequence analysis revealed that in total seven unique antibody clones had been selected (Table 2). For these seven Fab clones, the affinities measured in BIAcore™ were in the range of 10–180 nM (Table 4). When tested in the human protease assay, five of them were able to block the interaction between human TIMP-1 and MMP-1. The concentration of monovalent Fab needed to reverse the inhibitory effect of human TIMP-1 on human MMP-1 activity by 50% ($IC_{50}$) was in the range of 11–100 nM (Table 2). The most active Fab clones are MS-BW-3 ($K_d$ 13 nM; $IC_{50}$ 11 nM) and MS-BW-28 ($K_d$ 10 nM; $IC_{50}$ 22 nM).

A striking feature of antibodies selected against human TIMP-1 is that they all exhibit the combination VH312 and a relatively short VH-CDR3 region, predominantly four amino acids (see Table 2). The HCDR3 cassettes assembled for the HuCAL®-Fab 1 library were designed to achieve a length distribution ranging from 5 to 28 amino acid residues. A four amino acid HCDR3 can occur in the library due to TRIM deletion, but is considered a very rare event. Another remarkable feature was the high degree of sequence homology among the selected LCDR3 sequences.

TABLE 2

Overview of anti-human TIMP-1 Fab

| Fab | VH | HCDR3 | VL | LCDR3 | Monovalent $K_D$ | $IC_{50}$ in human to human TIMP-1 protease assay |
|---|---|---|---|---|---|---|
| MS-BW-1 | H3 | FMDI, SEQ ID NO:1 | λ2 | QSYDYQQFT, SEQ ID NO:44 | 65 +/− 13 nM* | >100 nM |
| MS-BW-2 | H3 | GFDY, SEQ ID NO:2 | λ2 | QSYDFKTYL, SEQ ID NO:45 | 180 +/− 28 nM | >100 nM |
| MS-BW-3 | H3 | FLDI, SEQ ID NO:3 | λ2 | QSYDFLRFS, SEQ ID NO:46 | 13+/− 2 nM | 11 +/− 2 nM |
| MS-BW-25 | H3 | TFPIDADS, SEQ ID NO:4 | λ2 | QSYDFINVI, SEQ ID NO:47 | 25+/− 16 nM | 115 +/− 15 nM |
| MS-BW-26 | H3 | GHVDY, SEQ ID NO:5 | λ2 | QSYDFVRFM, SEQ ID NO:48 | ~100 nM | non blocking |
| MS-BW-27 | H3 | YWRGLSFDI, SEQ ID NO:6 | λ2 | QSYDFYKFN, SEQ ID NO:49 | ~74 | non blocking |
| MS-BW-28 | H3 | FFDY, SEQ ID NO:7 | λ2 | QSYDFRRFS, SEQ ID NO:50 | 10 +/− 1 nM | 22 +/− 2 nM |

*In cases were standard deviations are given, three independent measurements were done with Fab from three different protein expressions/purifications.
~Indicates preliminary data, in cases where measurement was done only once.

EXAMPLE 17

Increasing the Affinity of Selected Anti-Human TIMP-1 Antibodies

In order to increase the affinity of monovalent anti-human TIMP-1 Fab fragments to the sub-nanomolar range, a stepwise affinity maturation approach was applied, by optimizing CDR sequences and keeping framework regions constant.

Affinity Maturation by Light Chain Cloning

The CDR3 sequences of the two antibody fragments with highest affinity (MS-BW-3 and MS-BW-28) had the remarkable feature of an unusually short four amino acid HCDR3 sequence. Furthermore, each Fab had a very similar LCDR3 sequence. This indicates that MS-BW-3 and MS-BW-28 bind to the same epitope and that this epitope might tolerate only a very small subset of CDR3 sequences. As a four amino acid HCDR3 is a very rare event in the library, it can be anticipated that in the initial library not all possible combinations of the short HCDR3 and the preferred LCDR3 are present. Therefore, it was considered that another combination of the selected HCDR3 and LCDR3 sequences might increase the affinity. For this approach, the heavy chain of MS-BW-3 and MS-BW-28 were paired with the light chains of MS-BW-1,-2,-3,-25,-26,-27, and -28 by cloning.

Figure 7:
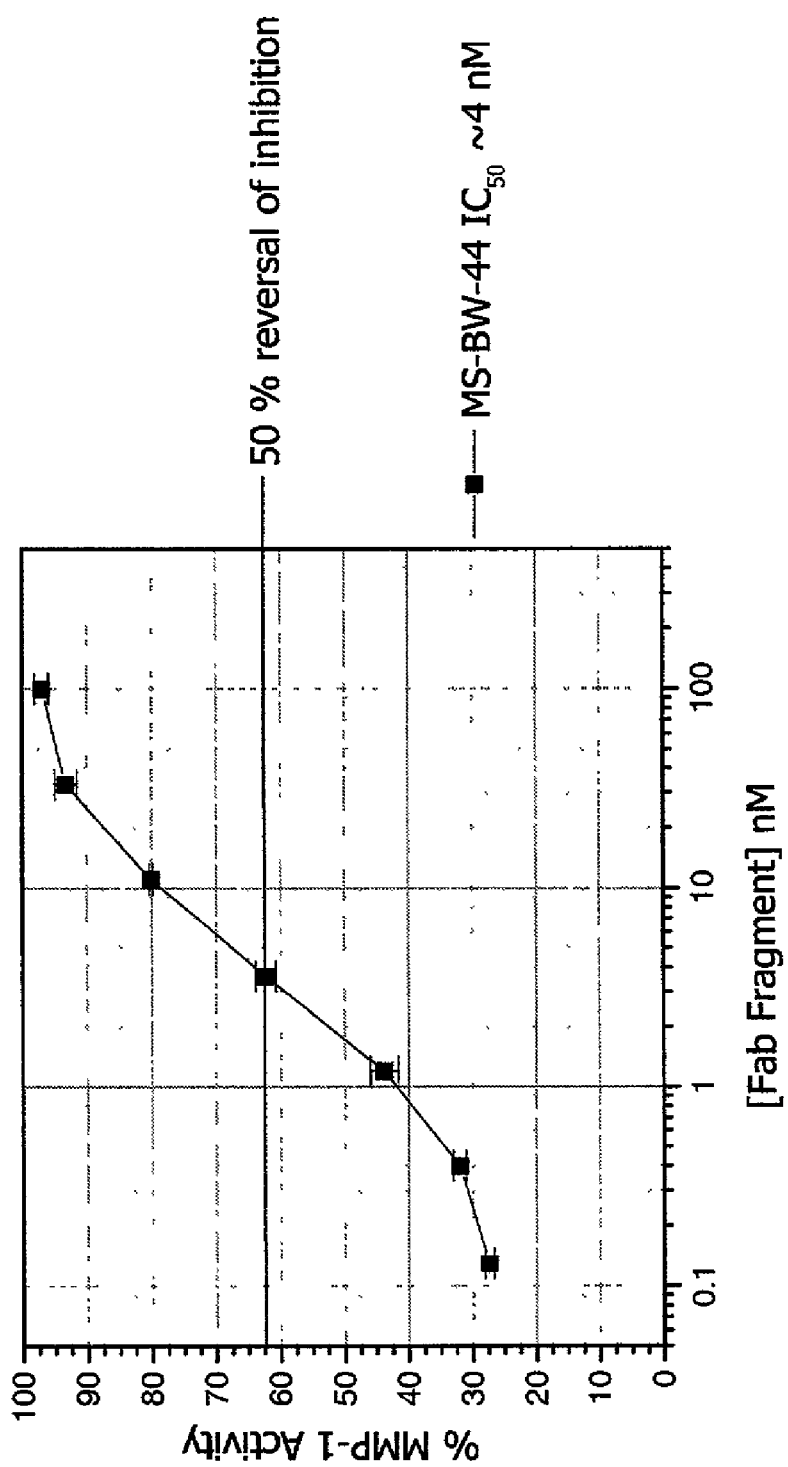
FIG. 7. Activity of MS-BW-44 in human TIMP-1/MMP-1 assay. Antibody Fab fragments were diluted in triplicate to the indicated concentrations in assay buffer containing 0.05% BSA. After addition of TIMP (final conc. 1.2 nM), MMP (final conc. 1.2 nM), and peptide substrate (final conc. 50 μM) and incubation for 1–3 h at 37° C. fluorescence at Ex320 nm/Em 430 nm was measured. IC$_{50}$ was calculated as outlined in material and methods section, using 100% MMP-1 activity (in absence of TIMP-1) and 25% MMP-1 activity (in absence of antibody) as reference values.

The resulting constructs were transformed into *E. coli* and expressions/purifications in 1-liter scale were performed. Of the 12 new constructs, 10 resulted in functional Fab molecules. These were analyzed in BIAcore™ and human protease assay as summarized in Table 3. The best antibody named MS-BW-44 had a monovalent affinity of 2 nM and an IC50 of 4 nM (FIG. 7) and was thus improved by a factor of 6.5 ($K_d$) or 2.75 ($IC_{50}$).

phage display vector pMORPH® 18 were created. In library 1, only HCDR2 of MS-BW-44 was diversified using "TRIM technology" as described in Virnekäs et al., *Nucl. Acids. Res.* 22, 5600–07, 1994; Knappik et al., *J. Mol. Biol.* 296, 57–86, 2000. In library 2, both HCDR1 and HCDR2 were diversified using the TRIM technology. In both cases, phage antibody libraries comprising $1\times10^8$ different clones were obtained. Both libraries were mixed and used as input for a modified AutoPan® procedure. In order to select antibodies having an increased affinity to human TIMP-1, solution panning using limiting amounts of biotinylated antigen and stringent washing conditions were applied. Antibody off rates were ranked by BIAcore™ using crude *E. coli* extracts of selected antibodies. Clones with slower off rate than parental clone MS-BW-44 were subjected to 1-liter scale expression and purification. Purified Fab were analyzed in BIAcore™ and human protease assay (Table 4).

TABLE 3

Overview of Fab derived from light chain cloning

| Fab | VH | HCDR3 | VL | LCDR3 | Monovalent $K_D$ to human TIMP-1 | $IC_5$* in human protease assay |
|---|---|---|---|---|---|---|
| MS-BW-40 | H3 | FLDI, SEQ ID NO:3 | λ2 | QSYDYQQFT, SEQ ID NO:44 | ~49 nM | >100 nM |
| MS-BW-41 | H3 | FLDI, SEQ ID NO:3 | λ2 | QSYDFKTYL, SEQ ID NO:45 | ~6 nM | 29 +/− 6 nM |
| MS-BW-43 | H3 | FLDI, SEQ ID NO:3 | λ2 | QSYDFINVI, SEQ ID NO:47 | ~65 nM | >100 nM |
| MS-BW-44 | H3 | FLDI, SEQ ID NO:3 | λ2 | QSYDFVRFM, SEQ ID NO:48 | 2 +/− 0.4 nM* | 4 +/− 1 nM |
| MS-BW-45 | H3 | FLDI, SEQ ID NO:3 | λ2 | QSYDFYKFN, SEQ ID NO:49 | 8 +/− 5 nM | 9 +/− 3 nM |
| MS-BW-46 | H3 | FLDI, SEQ ID NO:3 | λ2 | QSYDFRRFS, SEQ ID NO:50 | 6 +/− 3 nM | 4 +/− 0.5 nM |
| MS-BW-47 | H3 | FFDY, SEQ ID NO:7 | λ2 | QSYDYQQFT, SEQ ID NO:44 | ~152 nM | >100 nM |
| MS-BW-49 | H3 | FFDY, SEQ ID NO:7 | λ2 | QSYDFKTYL, SEQ ID NO:45 | −21 nM | >100 nM |
| MS-BW-51 | H3 | FFDY, SEQ ID NO:7 | λ2 | QSYDFINVI, SEQ ID NO:47 | ~7 nM | 7 +/− 1 nM |
| MS-BW-52 | H3 | FFDY, SEQ ID NO:7 | λ2 | QSYDFVRFM, SEQ ID NO:48 | ~11 nM | 9 +/− 1 nM |

*In cases were standard deviations are given, three independent measurements were done with Fab from three different protein expressions/purifications.
~Indicates preliminary data, in cases where measurement was done only once.

Affinity Maturation by Optimizing HCDR1 and HCDR2

In the HuCAL®-Fab 1 library, only the CDRs HCDR3 and LCDR3 are diversified to a high extent. Although it is known from crystallographic studies that amino acids from these two CDRs make most of the antibody antigen contacts, the residual four CDRs are also important for antigen binding. However, their contribution to the binding energy can vary from antibody to antibody. In the HuCAL®-Fab 1 library those CDRs exhibit only a limited variability due to the presence of the different master frameworks (Knappik et al., 2000). In order to improve the affinity of the selected antibodies, an affinity maturation approach by randomizing HCDR1 and HCDR2 was applied. For this approach two affinity maturation libraries based on MS-BW-44 cloned into

TABLE 4

Comparison of Fab derived from HCDR1 and HCDR2 optimization with parental clone MS-BW-44

| Fab | Monovalent $K_D$ to human TIMP-1 | $IC_{50}$ in human protease assay* |
|---|---|---|
| MS-BW-44 | 2 +/− 0.4 nM | 2 +/− 0.5 nM |
| MS-BW-44-2 | 0.5 +/− 0.2 nM | 0.4 +/− 0.3 nM |
| MS-BW-44-6 | 0.6 +/− 0.2 nM | 0.2 +/− 0.1 nM |

*$IC_{50}$ values derived from modified protease assay using decreased amounts of TIMP-1 and MMP-1 (0.4 nM each).

Clone MS-BW-44-2 was derived from library 1 thus having a modified HCDR2 cassette. Its affinity measured by BIAcore™ was 0.5 nM. Clone MS-BW-44-6 was derived from library 2 having a modified HCDR 1 and HCDR 2 cassette and the affinity measured by BIAcore™ was 0.6 nM. A sequence comparison between the affinity matured antibodies and their parental clones is shown in Table 8.

Affinity Maturation by Optimizing HCDR3

As mentioned above, amino acid residues in HCDR3 and LCDR3 are considered the most important for antigen binding. Taking into account that a four amino acid HCDR3

TABLE 8

Overview and sequence comparison of affinity matured Fab fragments against human TIMP-1. Sequence changes compared to parental Fab fragments (bold) are italicized

| Clone MS-BW- | Framework | VH HCDR1 sequence (SEQ ID NO:) | HCDR2 sequence (SEQ ID NO:) | HCDR3 sequence (SEQ ID NO:) | VL Framework | LCDR1 sequence (SEQ ID NO:) |
|---|---|---|---|---|---|---|
| 3 | VH3 | GFTFSSYAMS (355) | AISGSSGGSTYYADSVKG (357) | FLDI (3) | VL2 | TGTSSDVGGYNYVS (363) |
| 44 | VH3 | GFTFSSYAMS (355) | AISGSGGSTYYADSVKG (357) | FLDI (3) | VL2 | TGTSSDVGGYNYVS (363) |
| 44-6 | VH3 | GFTFNSYAMS (356) | VISGNGSNTYYADSVKG (358) | FLDI (3) | VL2 | TGTSSDVGGYNYVS (363) |
| 44-2 | VH3 | GFTFSSYAMS (355) | GISGNGVLIFYADSVKG (359) | FLDI (3) | VL2 | TGTSSDVGGYNYVS (363) |
| 44-2-4 | VH3 | GFTFSSYAMS (355) | GISGNGVLIFYADSVKG (359) | GLMDY (360) | VL2 | TGTSSDVGGYNYVS (363) |
| 44-2-15 | VH3 | GFTFSSYAMS (355) | GISGNGVLIFYADSVKG (359) | WFDH (361) | VL2 | TGTSSDVGGYNYVS (363) |
| 44-2-16 | VH3 | GFTFSSYAMS (355) | GISGNGVLIFYADSVKG (359) | WFDV (362) | VL2 | TGTSSDVGGYNYVS (363) |
| 44-6-1 | VH3 | GFTFNSYAMS (356) | VISGNGSNTYYADSVKG (358) | FLDI (3) | VL2 | TGTSSDVGGYNYVS (363) |

| Clone MS-BW- | VL LCDR2 sequence (SEQ ID NO:) | LCDR3 sequence (SEQ ID NO:) | Monov. $K_D$ to human TIMP-1 (nM) | $IC_{50}$ in human protease assay (nM) |
|---|---|---|---|---|
| 3 | DVSNRPS (364) | QSYDFLRFS (47) | 13 +/- 2 | 11 +/- 2 |
| 44 | DVSNRPS (364) | QSYDFVRFM (48) | 2 +/- 0.4 | 4 +/- 1 |
| 44-6 | DVSNRPS (364) | QSYDFVRFM (48) | 0.6 +/- 0.2 | 0.2 +/- 0.1* |
| 44-2 | DVSNRPS (364) | QSYDFVRFM (48) | 0.5 +/- 0.2 | 0.4 +/- 0.3* |
| 44-2-4 | DVSNRPS (364) | QSYDFVRFM (48) | 0.2 +/- 0.02 | 0.2 +/- 0.1* |
| 44-2-15 | DVSNRPS (364) | QSYDFVRFM (48) | 0.3 +/- 0.1 | 0.2 +/- 0.1* |
| 44-2-16 | DVSNRPS (364) | QSYDFVRFM (48) | 0.5 +/- 0.2 | 0.3 +/- 0.1* |
| 44-6-1 | DVSNRPS (364) | QSYDFIRFM (365) | 0.2 +/- 0.04 | 0.2 +/- 0.1* |

Figure 8:
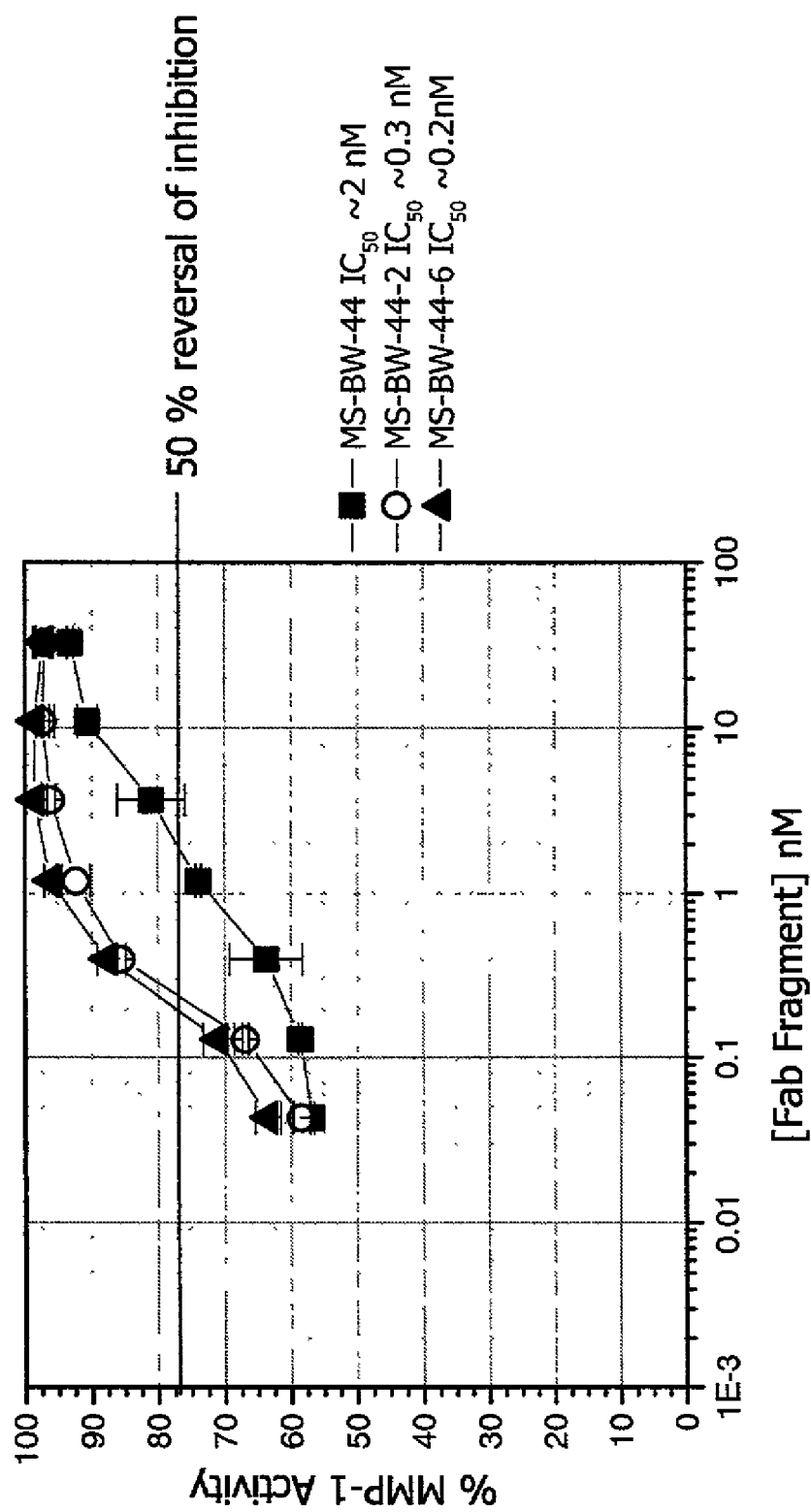
FIG. 8. Activity of MS-BW-44, -44-2, 44-6 in human TIMP-1/MMP-1 assay. Fab antibody fragments were diluted in triplicate to the indicated concentrations in assay buffer containing 0.05% BSA. After addition of TIMP (final conc. 0.4 nM), MMP (final conc. 0.4 nM) and peptide substrate (final conc. 50 μM) and incubation for 7 h at 37° C. fluorescence at Ex320 nm/Em 430 nm was measured. IC$_{50}$ was calculated as outlined in material and methods section, using 100% MMP-1 activity (in absence of TIMP-1) and 55% MMP-1 activity (in absence of antibody) as reference values.
Figure 9:
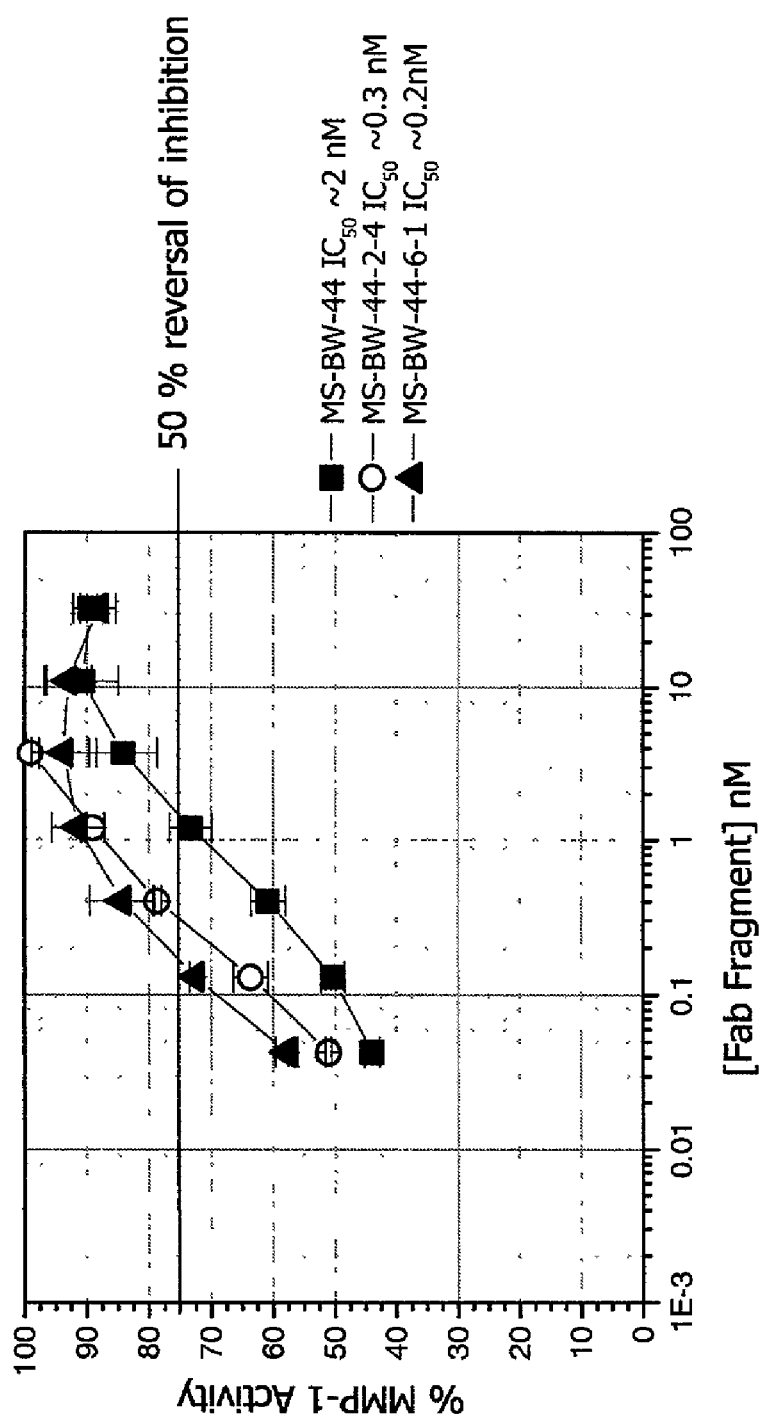
FIG. 9. Activity of MS-BW-44,-44-2-4, 44-6-1 in human TIMP-1/MMP-1 assay. Antibody Fab fragments were diluted in triplicate to the indicated concentrations in assay buffer containing 0.05% BSA. After addition of TIMP (final conc. 0.4 nM), MMP (final conc. 0.4 nM), and peptide substrate (final conc. 50 μM) and incubation for 7 h at 37° C. fluorescence at Ex320 nm/Em 430 nm was measured. IC$_{50}$ was calculated as outlined in material and methods section, using 100% MMP-1 activity (in absence of TIMP-1) and 50% MMP-1 activity (in absence of antibody) as reference values.

*$IC_{50}$ values derived from modified protease assay using decreased amounts of TIMP-1 and MMP-1; $IC_{50}$ of MS-BW-44 is 2 nM under these conditions When initially analyzed in the human TIMP-1/MMP-1 assay, it was not possible to distinguish a Fab with a sub-nanomolar affinity from a Fab with 1 nM affinity, most likely because the concentration of Fab required to reverse the inhibitory effect of human TIMP-1 on human MMP-1 activity by 50% was below the concentration of total TIMP-1 in the assay. When a modified assay was used with concentrations of TIMP-1 and MMP-1 decreased from 1.2 nM to 0.4 nM, it was possible to distinguish a 2 nM Fab from a sub-nanomolar Fab (Table 4, FIG. 8). Using this modified protease assay, MS-BW-44-2 and MS-BW-44-6 had $IC_{50}$ values of 0.4 nM and 0.2 nM respectively. Parental clone MS-BW-44 had an $IC_{50}$ of 2 nM under these conditions. Thus, by this affinity maturation approach, an affinity gain of a factor of 5 ($K_d$) or 5–10 ($IC_{50}$) was achieved.

was not planned in the design of HuCAL®-Fab 1 and thus only occurs as a rare case due to a TRIM deletion, probably not all possible combinations of the four amino acids in HCDR3 were represented in the original HuCAL®-Fab 1 library. Therefore, an affinity maturation library was constructed with four and five amino acid HCDR3 maturation cassettes inserted into Fab derived from the previous maturation cycle (among them MS-BW-44-2 and MS-BW-44-6). The obtained affinity maturation library had a diversity of $1 \times 10^8$ clones, therefore theoretically covering all possible four and five amino acid HCDR3 variations. Applying very stringent panning conditions, the best antibody identified, MS-BW-44-2-4, had an affinity measured by BIAcore™ of 0.2 nM and an $IC_{50}$ in human TIMP-1/MMP-1 assay of 0.2 nM. A sequence comparison between the affinity matured antibodies and their parental clones is shown in Table 8. The improvement factor gained by this affinity maturation approach is 2.5 with respect to the affinity and 2 with respect to the $IC_{50}$.

Affinity Maturation by Optimizing LCDR3

As an alternative approach, a maturation strategy was used to further optimize the light chain CDR3 sequence. This was due to the fact that in the first maturation cycle where light chain exchange cloning between selected antibodies was applied, only a very limited subset of sequence variation had been exploited. Therefore, a maturation library was constructed in which, using TRIM technology, a diversified LCDR3 cassette was inserted into Fab derived from HCDR1 and HCDR2 optimization (among them MS-BW-44-2 and MS-BW-44-6). The best Fab identified with this maturation strategy was MS-BW-44-6-1 with an affinity measured by BIAcore™ of 0.15 nM and an $IC_{50}$ in a human TIMP-1/MMP-1 assay of 0.2 nM. A sequence comparison between the affinity matured antibody and its parental clones is shown in Table 8. The improvement factor gained by this maturation approach is 4 with respect to affinity. A further improvement of the $IC_{50}$ in the protease assay could not be measured due to limitations in the assay.

As a result of a step-wise affinity maturation approach using four different maturation strategies, the monovalent affinity of an anti-human TIMP-1 specific Fab fragment was improved by a factor of 87 and its activity in human TIMP-1/MMP-1 assay by a factor of 55. The decision for defining the best Fab fragment has been made on the basis of $K_d$ measurements using BIAcore™, as this method proved to be reliable for ranking antibodies with sub-nanomolar affinities, whereas the sensitivity of the human TIMP-1/MMP-1 assay was considered not suitable to rank activity of the best Fabs in the sub-nanomolar range with respect to each other.

The best Fab MS-BW-44-6-1 has an affinity measured by BIAcore™ of 0.15 nM and an $IC_{50}$ in human TIMP-1/MMP-1 assay of 0.2 nM. Compared to its parental clone, MS-BW-3, it has optimized LCDR3, HCDR1 and HCDR2 sequences.

EXAMPLE 18

Cross Reactivity of Selected Anti-Human TIMP-1 Fab with TIMP-2, TIMP-3, and TIMP-4

Figure 10:
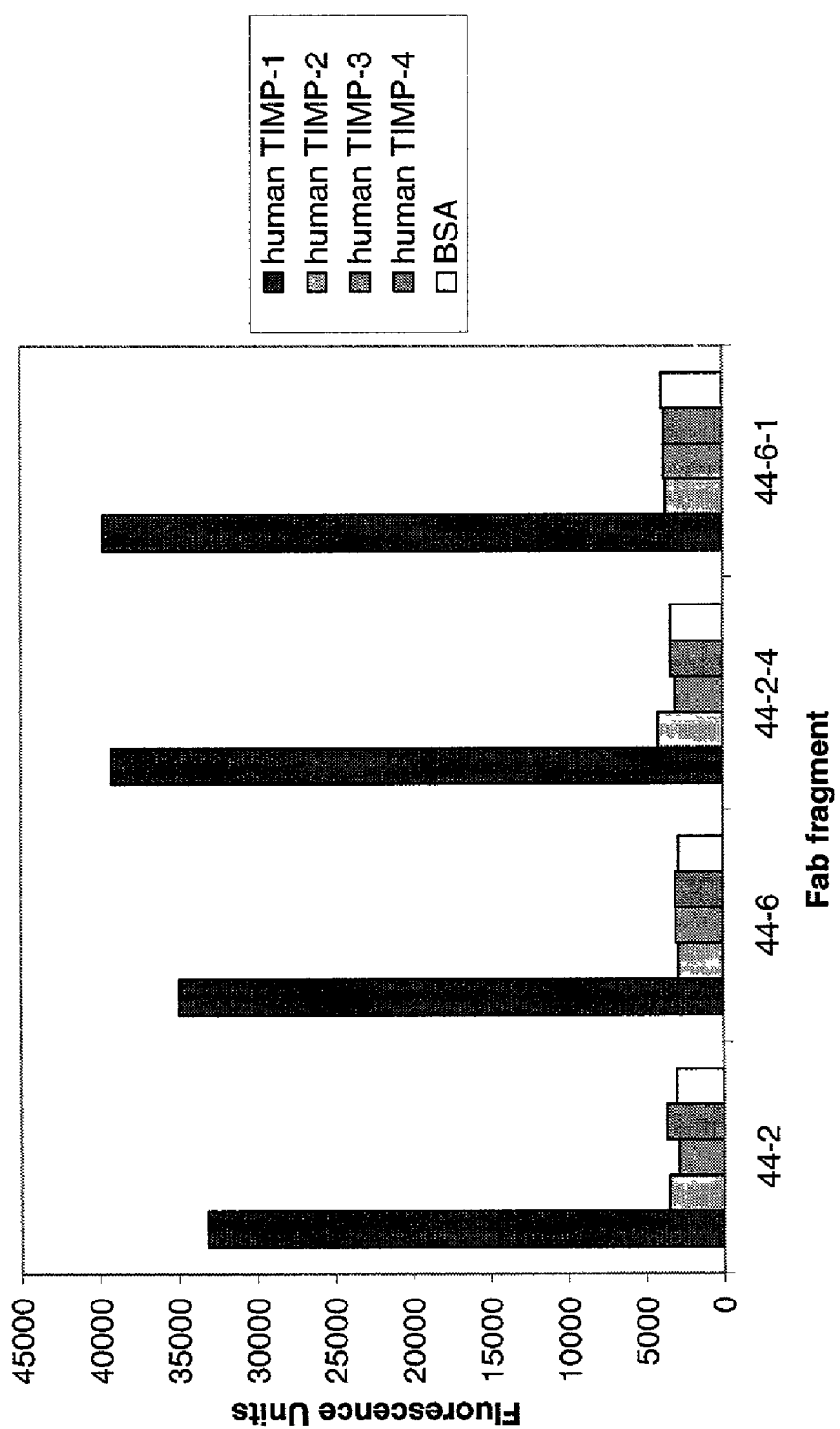
FIG. 10. Binding of Fab fragments to human TIMP-1,-2,-3 and -4. TIMP-1,-2,-3,-4 proteins were immobilized on an ELISA plate, and binding of purified Fab fragments was measured by incubation with alkaline phosphatase conjugated anti-Fab antibody (Dianova) followed by development with Attophos substrate (Roche) and measurement at Ex405 nm/Em535 nm.
Figure 11:
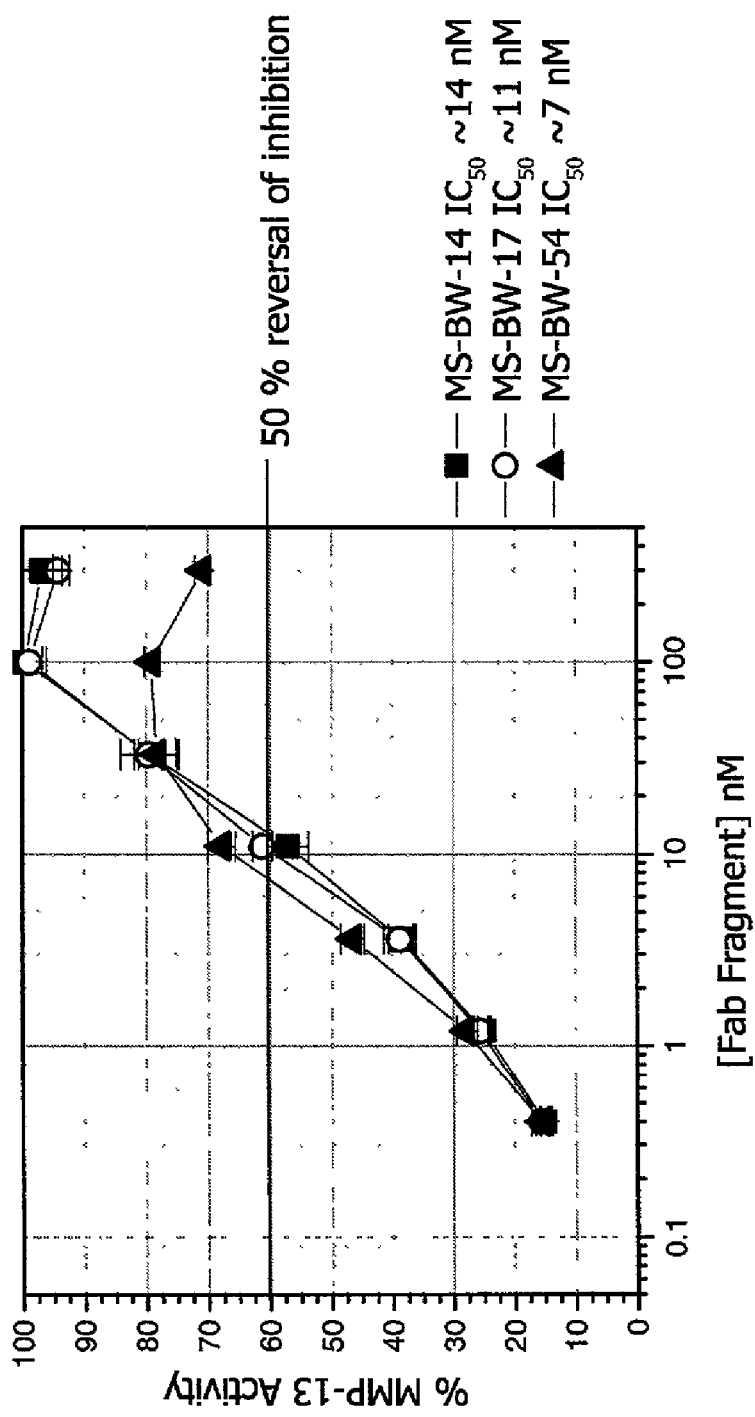
FIG. 11. Activity of MS-BW-14,-17,-54 in rat TIMP-1/MMP-13 assay. Antibody Fab fragments were diluted in triplicate to the indicated concentrations in assay buffer containing 0.05% BSA. After addition of TIMP (final conc. 1.2 nM), MMP (final conc. 1.2 nM), and peptide substrate (to final conc. 50 μM) and incubation for 1–3 h at 37° C, fluorescence at Ex320 nm/Em 430 nm was measured. IC$_{50}$ was calculated as outlined in material and methods section, using 100% MMP-13 (in absence of TIMP-1) activity and 20% MMP-13 activity (in absence of antibody) as reference values.

TIMP-1 belongs to a family of closely related protease inhibitors all binding to various members of the MMP family of proteases. To date there are four human TIMP proteins described. To investigate potential cross-reactivity of antibody fragments selected against human TIMP-1 with other members of the human TIMP family, an ELISA was performed in which binding of antibody fragments to immobilized purified human TIMP-1,-2,-3 or 4 was analyzed (FIG. 10). Antibody fragments binding to immobilized human TIMP-1 showed no binding to human TIMP-2,-3,-4 above background level when compared to unrelated control protein BSA.

EXAMPLE 19

Generation of Blocking Antibodies Against Rat TIMP-1

To generate blocking antibodies against rat TIMP-1, the HuCAL®-Fab 1 library was used for antibody selection (AutoPan®) on immobilized rat TIMP-1 followed by subcloning and expression of the selected Fab fragments in *E. coli*. Crude antibody-containing *E. coli* extracts were used for primary antibody characterization in ELISA (AutoScreen®). Purified Fab proteins were subjected to further characterization in ELISA, protease assays, and BIAcore™. Of the 8,450 selected clones were analyzed in AutoScreen®, 750 of them showed binding to rat TIMP-1. Sequence analysis revealed that in total 36 unique Fab clones specific for rat TIMP-1 were enriched during selection (Table 7). Their affinities were measured by BIAcore™ and were found to be in the range of 9–1000 nM (Table 7). When tested in the rat protease assay, all but one of them were able to block the interaction between rat TIMP-1 and rat MMP-13 (Table 7). The concentration of monovalent Fab needed to reverse the inhibitory effect of rat TIMP-1 on rat MMP-13 activity by 50% ($IC_{50}$) was in the range of 7–300 nM. The most active Fab clones are MS-BW-14 ($K_d$ 10 nM; $IC_{50}$ 14 nM), MS-BW-17 ($K_d$ 13 nM; $IC_{50}$ 11 nM), and MS-BW-54 ($K_d$ 9 nM; $IC_{50}$ 7 nM).

TABLE 7

Overview of anti-rat TIMP-1 Fab

| Fab | VH | HCDR3 | VL | LCDR3 | Monovalent $K_D$ to rat TIMP-1 | $IC_{50}$* in rat protease assay |
|---|---|---|---|---|---|---|
| MS-BW-5 | H1A | GLYWAVYPYFDF, SEQ ID NO:8 | λ1 | QSRDFNRGP, SEQ ID NO:51 | ~210 nM | non blocking |
| MS-BW-6 | H3 | LDTYYPDLFDY, SEQ ID NO:9 | λ1 | QSYDQRKW, SEQ ID NO:52 | ~68 nM | ~100 nM |
| MS-BW-7 | H1A | TYYYFDS, SEQ ID NO:10 | κ3 | QQLYGTVS, SEQ ID NO:53 | ~168 nM | >300 nM |
| MS-BW-9 | H3 | YMAYMAEAIDV, SEQ ID NO:11 | λ1 | QSYDGFKTH, SEQ ID NO:54 | ~256 nM | >300 nM |
| MS-BW-10 | H1B | LVGIVGYKPDELLYFDV, SEQ ID NO:12 | λ3 | QSYDYSLL, SEQ ID NO:55 | ~200 nM | ~30 nM |
| MS-BW-11 | H3 | YGAYFGLDY, SEQ ID NO:13 | λ3 | QSYDFNFH, SEQ ID NO:56 | ~200 nM | >300 nM |
| MS-BW-12 | H6 | GYADISFDY, SEQ ID NO:14 | λ2 | QSYDMIARYP, SEQ ID NO:57 | ~419 nM | >300 nM |
| MS-BW-13 | H3 | YYLLLDY, SEQ ID NO:15 | λ3 | QSWDIHPFDV, SEQ ID NO:58 | ~939 nM | not tested |
| MS-BW-14 | H1A | WSDQSYHYYWHPYFDV, SEQ ID NO:16 | λ1 | QSWDLEPY, SEQ ID NO:59 | 10 +/− 5 nM | 14 +/− 3 nM |

TABLE 7-continued

Overview of anti-rat TIMP-1 Fab

| Fab | VH | HCDR3 | VL | LCDR3 | Monovalent $K_D$ to rat TIMP-1 | $IC_{50}$* in rat protease assay |
|---|---|---|---|---|---|---|
| MS-BW-15 | H3 | LIGYFDL, SEQ ID NO:17 | λ2 | QSYDVLDSE, SEQ ID NO:60 | ~80 nM | ~200 nM |
| MS-BW-17 | H5 | LTNYFDSIYYDH, SEQ ID NO:18 | λ2 | QSYDPSHPSK, SEQ ID NO:61 | 13 +/- 3 nM | 11 +/- 3 nM |
| MS-BW-18 | H5 | LVGGGYDLMFDS, SEQ ID NO:19 | λ2 | QSYDDMQF, SEQ ID NO:62 | ~153 nM | >300 nM |
| MS-BW-19 | H5 | YVTYGYDDYHFDY, SEQ ID NO:20 | λ2 | QSWDINHAI, SEQ ID NO:63 | ~187 nM | >300 nM |
| MS-BW-20 | H1A | SGYLDY, SEQ ID NO:21 | λ2 | QSYDYYDYG, SEQ ID NO:64 | ~70 nM | >300 nM |
| MS-BW-21 | H1A | YIGYTNVMDIRPGYFLDY, SEQ ID NO:22 | κ3 | QQANDFPI, SEQ ID NO:65 | 36 +/- 2 nM | 67 +/- 5 nM |
| MS-BW-22 | H5 | FRAYGDDFYFDV, SEQ ID NO:23 | λ2 | QSWDNLKMPV, SEQ ID NO:66 | 35 nM | 65 +/- 11 nM |
| MS-BW-23 | H1B | JMWSDYGQLVKGGDI, SEQ ID NO:24 | λ2 | QSYDVFPINR, SEQ ID NO:67 | ~207 nM | >300 nM |
| MS-BW-24 | H5 | YYVTDTAYFDY, SEQ ID NO:25 | λ2 | QSDLYFP, SEQ ID NO:68 | 23 nM | 20 +/- 1 nM |
| MS-BW-29 | H5 | HDFDGSIFMDF, SEQ ID NO:26 | λ2 | QSYDVTPR, SEQ ID NO:69 | ~214 nM | >100 nM |
| MS-BW-30 | H5 | YAGHQYEFFFDF, SEQ ID NO:27 | λ3 | QSRDPVGFP, SEQ ID NO:70 | ~36 nM | >100 nM |
| MS-BW-31 | H5 | LYADADIYFDY, SEQ ID NO:28 | λ2 | QSYDLSPR, SEQ ID NO:71 | ~13 +/- 9 nM | >100 nM |
| MS-BW-32 | H1A | TKYVGSEDV, SEQ ID NO:29 | λ2 | QSYDFSHYFF, SEQ ID NO:72 | ~92 nM | >100 nM |
| MS-BW-36 | H5 | YRYPHMFDF, SEQ ID NO:30 | λ3 | QSYDLRYSH, SEQ ID NO:73 | ~42 nM | ~75 nM |
| MS-BW-37 | H5 | LFAGLELYFDY, SEQ ID NO:31 | λ2 | QSYDLRNR, SEQ ID NO:74 | 10 +/- 9 nM | >100 nM |
| MS-BW-38 | H3 | GGFFNMDY, SEQ ID NO:32 | λ2 | QSYDFTYGS, SEQ ID NO:75 | ~353 nM | >300 nM |
| MS-BW-39 | H1A | GYIPYHLFDY, SEQ ID NO:33 | κ3 | QQFNDSPY, SEQ ID NO:76 | ~108 nM | >100 nM |
| MS-BW-54 | H5 | YYGFEYDLLFDN, SEQ ID NO:34 | λ2 | QSYDISGYP, SEQ ID NO:77 | 9 +/- 1 nM | 7 nM |
| MS-BW-55 | H1B | ITYIGYDF, SEQ ID NO:35 | λ2 | QSRDLYYVYY, SEQ ID NO:78 | ~23 nM | ~100 nM |
| MS-BW-56 | H1A | QEWYMDY, SEQ ID NO:36 | λ3 | QSYDRSMW, SEQ ID NO:79 | ~170 nM | >100 nM |
| MS-BW-57 | H5 | LYPEDLIYFDY, SEQ ID NO:37 | λ2 | QSWDVQTDK, SEQ ID NO:80 | ~39 nM | ~60 nM |
| MS-BW-58 | H6 | WMTPPGHYYGYTFDV, SEQ ID NO:38 | λ3 | QSWDPSHYY, SEQ ID NO:81 | ~138 nM | not tested |
| MS-BW-59 | H5 | LRVHDYAMYFDL, SEQ ID NO:39 | λ2 | QSYDIMPER, SEQ ID NO:82 | ~15 nM | 30 +/- 5 nM |
| MS-BW-60 | H5 | FVSYNGSVPYFDY, SEQ ID NO:40 | λ2 | QSMDFRLMH, SEQ ID NO:83 | ~30 nM | >100 nM |
| MS-BW-61 | H5 | IIGDYVIFFDV, SEQ ID NO:41 | λ2 | QSFDMIHPY, SEQ ID NO:84 | ~51 nM | >100 nM |
| MS-BW-62 | H5 | LFTYPFLYFDY, SEQ ID NO:42 | λ2 | QSDFPVM, SEQ ID NO:85 | ~36 nM | 19 +/- 2 |
| MS-BW-63 | H5 | ILTGHVLLFDY, SEQ ID NO:43 | λ2 | QSDNPYL, SEQ ID NO:86 | ~14 nM | 20 +/- 1 mM |

*In cases were standard deviations are given, three independent measurements were done with Fab from three different protein expressions/purifications.
~Indicates preliminary data, in cases where measurement was done only once.

EXAMPLE 20

Increasing the Affinity of Selected Anti-Rat TIMP-1 Antibodies

Affinity maturation was applied to increase the affinity of monovalent anti-rat TIMP-1 Fab fragments to the sub-nanomolar range. No clear sequence homology could be identified among the light chain CDR3 sequences of the selected antibody fragments, indicating that an optimal light chain CDR3 sequence was probably not present or had not been selected from the original HuCAL®-Fab 1 library. We therefore started with modification of LCDR3 to increase the affinity of Fabs.

Two affinity maturation libraries based on MS-BW-14, -17, and -54 cloned into phage display vector pMORPH® 18 were created. In library 1, only LCDR3 was diversified using TRIM technology, as described in Virnekäs et al., Nucl. Acids. Res. 22, 5600–07, 1994; Knappik et al., J. Mol. Biol. 296, 57–86, 2000. In library 2, LCDR1, LCDR2, and LCDR3 were diversified simultaneously using the TRIM technology, while the connecting framework regions were kept constant. In both cases, phage antibody libraries comprising 3×10$^8$ different clones were obtained. Both libraries were mixed and used as input for a modified AutoPan® procedure. To select antibodies having an increased affinity to rat TIMP-1, solution panning using limiting amounts of biotinylated antigen and stringent washing conditions were applied.

Antibody-off-rates were ranked by BIAcore™ using crude E. coli extracts. Clones with slower off rate than parental clones MS-BW-14, -17, or -54 were subjected to expression and purification in 1-liter scale. Purified Fab were analyzed in BIAcore™ and rat protease assays (Table 6). MS-BW-17-1 ($K_d$ 0.8 nM, $IC_{50}$ 1.6 nM), MS-BW-17-2 ($K_d$ 1.3 nM, $IC_{50}$ 1.1 nM), and MS-BW-17-3 ($K_d$ 1.9 nM, $IC_{50}$ 3 nM) were derived from affinity maturation library 1 having an optimized LCDR3 sequence, whereas MS-BW-54-1 ($K_d$ 2 nM, $IC_{50}$ 3 nM) was derived from affinity maturation library 2 having an optimized LCDR1,-2, and -3 sequence (Table 9).

EXAMPLE 21

Conversion of Anti-TIMP-1 Fab Fragments into Human $IgG_1$ Molecules for use in the Rat Model of Chronic Carbon Tetrachloride-Induced Liver Fibrosis Anti-TIMP-1 Fab fragments were converted into human IgG1 molecules to create antibody molecules with prolonged in vivo half-lives for the use in the rat model of chronic carbon tetrachloride-induced liver fibrosis. This was done by cloning the heavy and light chain variable regions of the Fab into two separate vectors for mammalian $IgG_1$ expression (Krebs et al., 2001)

Anti-rat TIMP-1 clone MS-BW-14 was chosen for the first in vivo study, and $IgG_1$ protein was produced by transient expression. Anti-human TIMP-1 clone MS-BW-3 was selected as a negative control $IgG_1$ and was also produced by transient expression. Purified $IgG_1$ proteins MS-BW-14 and MS-BW-3 were subjected to quality control in BIAcore™ and rat TIMP-1/rat MMP-13 assays. Bivalent affinity for rat TIMP-1 measured in BIAcore™ (chip density 500 RU, fitting model for bivalent analyte) is 0.2 nM for MS-BW-14, compared to 13 nM for the corresponding

TABLE 9

Overview and sequence comparison of affinity matured Fab fragments against rat TIMP-1. Sequence changes compared to parental Fab fragments (bold) are italicized.

| Clone (MS-BW-) | Framework | HCDR1 sequence (SEQ ID NO:) | HCDR2 sequence (SEQ ID NO:) | HCDR3 sequence (SEQ ID NO:) | Framework | LCDR1 sequence (SEQ ID NO:) |
|---|---|---|---|---|---|---|
| 14 | VH1A | GGTFSSYAIS (366) | GIIPIFGTANYAQKFQG (368) | WSDQSYHYYWHPYFDV (370) | VL1 | SGSSSNIGSNYVS (371) |
| 17 | VH5 | GYSFTSYWIG (367) | IIYPGDSDTRYSPSFQG (369) | LTNYFDSIYYDH (18) | VL2 | TGTSSDVGGYNYVS (363) |
| 54 | VH5 | GYSFTSYWIG (367) | IIYPGDSDTRYSPSFQG (369) | YYGFEYDLLFDN (34) | VL2 | TGTSSDVGGYNYVS (363) |
| 17-1 | VH5 | GYSFTSYWIG (367) | IIYPGDSDTRYSPSFQG (369) | LTNYFDSIYYDH (18) | VL2 | TGTSSDVGGYNYVS (363) |
| 17-2 | VH5 | GYSFTSYWIG (367) | IIYPGDSDTRYSPSFQG (369) | LTNYFDSIYYDH (18) | VL2 | TGTSSDVGGYNYVS (363) |
| 17-3 | VH5 | GYSFTSYWIG (367) | IIYPGDSDTRYSPSFQG (369) | LTNYFDSIYYDH (18) | VL2 | TGTSSDVGGYNYVS (363) |
| 54-1 | VH5 | GYSFTSYWIG (367) | IIYPGDSDTRYSPSFQG (369) | YYGFEYDLLFDN (34) | VL2 | TGTSS*DL*GGYNYVS (372) |

| Clone (MS-BW-) | LCDR2 sequence (SEQ ID NO:) | LCDR3 sequence (SEQ ID NO:) | Monov. $K_D$ to rat TIMP-1 (nM) | $IC_{50}$ in rat protease assay (nM) |
|---|---|---|---|---|
| 14 | LMIYDNNQRPS (373) | QSWDLEPY (59) | 10 +/- 5 | 14 +/- 3 |
| 17 | LMIYDVSNRPS (374) | QSYDPSHPSK (61) | 13 +/- 3 | 11 +/- 3 |
| 54 | LMIYDVSNRPS (374) | QSYDISGYP (77) | 9 +/- 1 | 7 |
| 17-1 | LMIYDVSNRPS (374) | QAFDVAPNGK (376) | 0.8 | 1.6 |
| 17-2 | LMIYDVSNRPS (374) | QAFAVMPNVE (377) | 1.3 | 1.1 |
| 17-3 | LMIYDVSNRPS (374) | QSFTVSPGAD (378) | 1.9 | 3 |
| 54-1 | LMIY*AG*NNRPS (375) | QAYDSSGYP (379) | 2 | 3 |

The improvement gained by these different one-step maturation strategies was up to a factor of 16.3 with regard to affinity and 10 with regard to functional activity in the protease assay.

monovalent Fab fragment. This increase in affinity for the $IgG_1$ is due to the avidity effects caused by binding of bivalent $IgG_1$ to immobilized rat TIMP-1 protein on the BIAcore™ chip. As expected, the negative control $IgG_1$ MS-BW-3 showed no binding to rat TIMP-1 but bound to human TIMP-1 with a bivalent affinity of approximately 0.4 nM.

Figure 12:
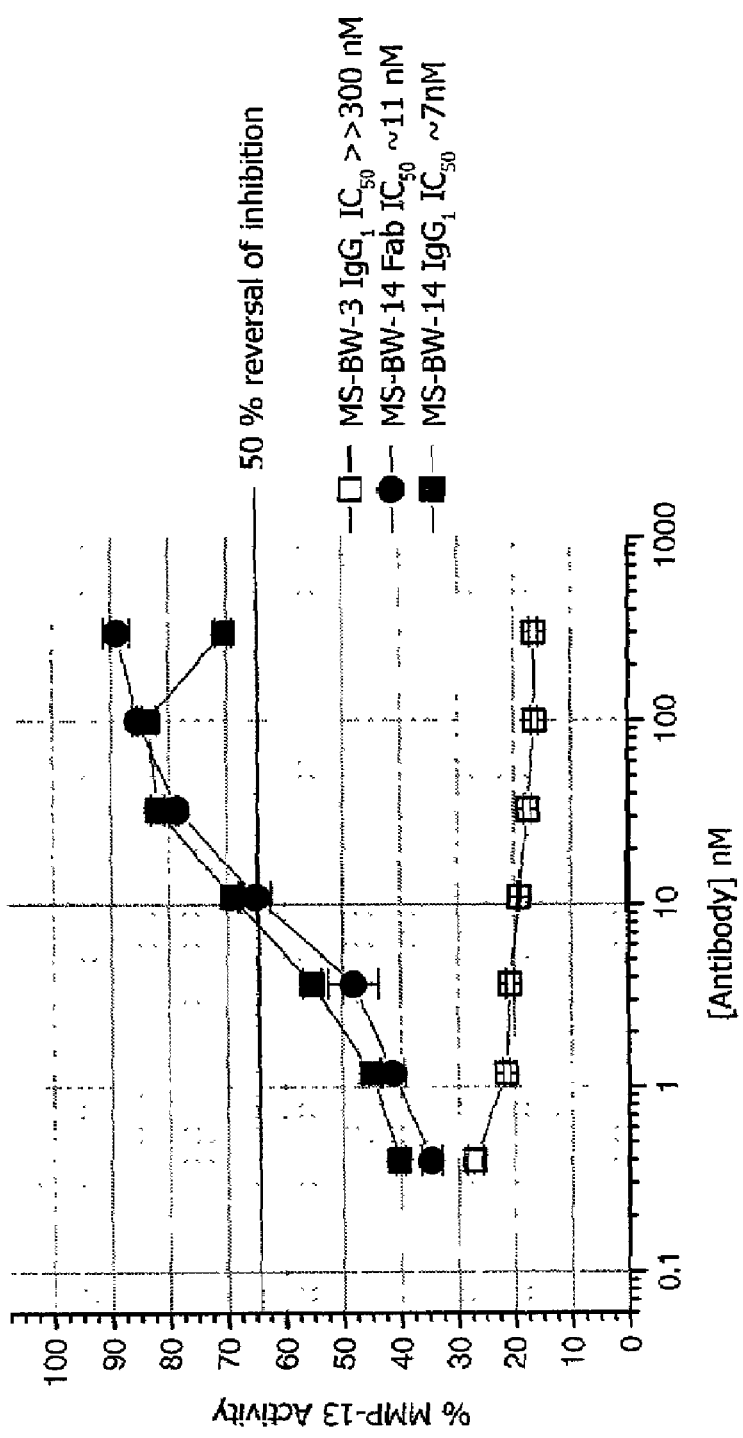
FIG. 12. Activity of MS-BW-14 Fab and IgG$_1$ and MS-BW-3 IgG$_1$ in rat TIMP-1/MMP-13 assay. Antibodies were diluted in triplicate to the indicated concentrations in assay buffer containing 0.05% BSA. After addition of TIMP (final conc. 1.2 nM), MMP (final conc. 1.2 nM) and peptide substrate (to final conc. 50 μM) and incubation for 1–3 h at 37° C., fluorescence at Ex320 nm/Em 430 nm was measured. IC$_{50}$ was calculated as outlined in material and methods section, using 100% MMP-13 activity (in absence of TIMP-1) and 30% MMP-13 activity (in absence of antibody) as reference values.

FIG. 12 shows the activity of MS-BW-14 Fab and IgG$_1$ and MS-BW-3 IgG$_1$ in a rat TIMP-1/rat MMP-13 assay. The IC$_{50}$ of MS-BW-14 Fab and IgG$_1$ are nearly identical. The avidity effect seen in BIAcore™ does not occur in this assay because, in contrast to the BIAcore™ experiment, this assay is based on a monovalent interaction in solution between TIMP-1 and the IgG$_1$. As expected, MS-BW-3 has no effect on rat TIMP-1 binding to rat MMP-13 and thus is a suitable negative control for a rat in vivo study.

Figure 13:
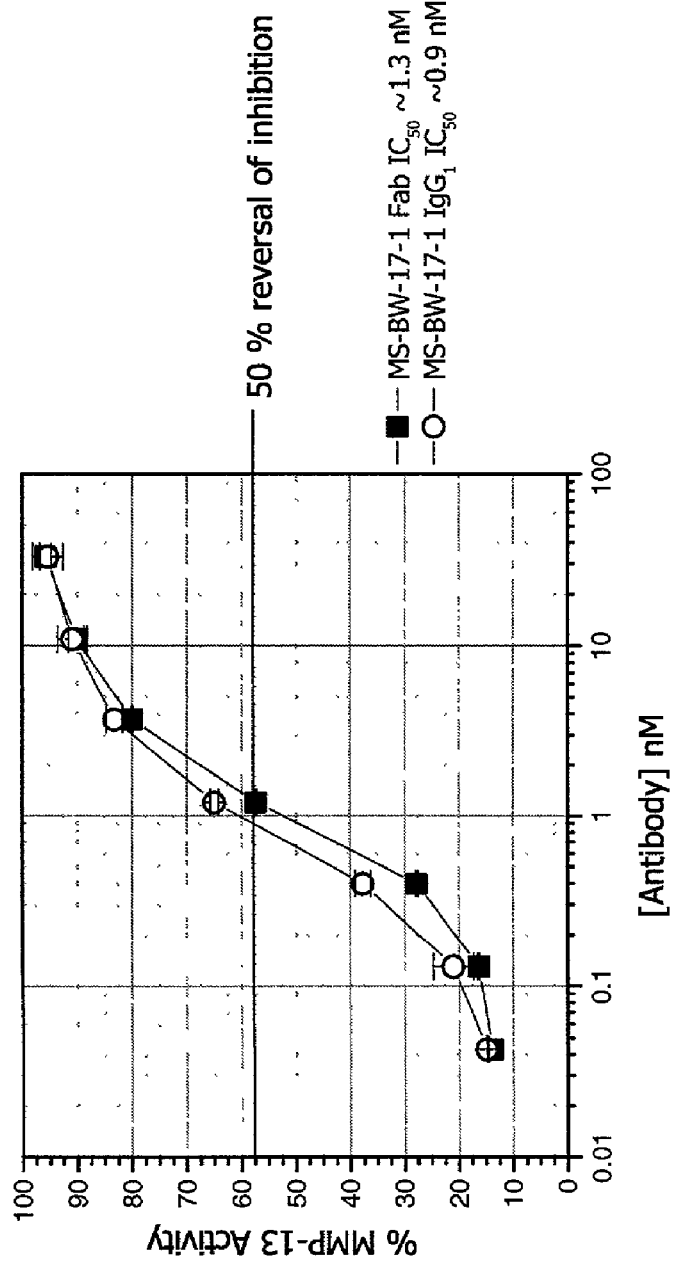
FIG. 13. Activity of MS-BW-17-1 Fab and IgG$_1$ in rat TIMP-1/MMP-13 assay. Fab antibody fragments were diluted in triplicate to the indicated concentrations in assay buffer containing 0.05% BSA. After addition of TIMP (final conc. 1.2 nM), MMP (final conc. 1.2 nM) and peptide substrate (to final conc. 50 μM) and incubation for 1–3 h at 37° C. fluorescence at Ex320 nm/Em 430 nm was measured. IC$_{50}$ was calculated as outlined in material and methods section, using 100% MMP-13 activity (in absence of TIMP-1) and 15% MMP-13 activity (in absence of antibody) as reference values.

Affinity matured clone MS-BW-17-1 was then converted from a monovalent Fab fragment to a bivalent IgG$_1$. Protein was produced by stable transfection. Purified protein was subjected to quality control in BIAcore™ and rat TIMP-1/rat MMP-13 assays (FIG. 13). In BIAcore™ an increased bivalent affinity (avidity) of 0.04 nM for IgG$_1$ compared to 0.8 nM for monovalent Fab fragment was seen, whereas the activity in the rat TIMP-1/rat MMP-13 assay was comparable for IgG$_1$ and Fab as expected.

EXAMPLE 22

Cross-Reactivity of Anti-Rat TIMP-1 IgG$_1$ MS-BW-17-1 with Mouse TIMP-1

Species cross-reactivity of MS-BW-17-1 IgG$_1$ and Fab with mouse TIMP-1 was determined by BIAcore™ to investigate the feasibility of alternative in vivo models that use mice instead of rats. Although MS-BW-17-1 clearly bound to mouse TIMP-1 immobilized to the chip surface, the affinity of both Fab (180 nM) and IgG$_1$ (9 nM) was 225-fold weaker than the affinity to rat TIMP-1. As the interaction between mouse TIMP-1 and BW-17-1 IgG$_1$ in serum is most likely monovalent, the affinity of BW-17-1 Fab probably reflects the "real" affinity of this interaction. Therefore, the Fab affinity value should be considered when calculating the feasibility of using BW-17-1 IgG$_1$ in a mouse in vivo study.

EXAMPLE 23

Effect of Timp-1 Antibody on the Development of Bleomycin-Induced Pulmonary Fibrosis The following example demonstrates the ability of a human anti-rat Timp-1 antibody (BW17.1) to prevent fibrotic collagen deposition in a bleomycin-induced rat lung fibrosis model.

Male Lewis rats (6 weeks of age) received a single intratracheal challenge with bleomycin (0.3 mg/rat, in saline) or vehicle (saline) on day 0. Fourteen days later, animals were euthanized, the lung excised, fixed, and processed for evaluation of lung fibrosis. Lung tissue sections were cut, and quantitative assessment by image analysis of lung collagen in lung tissue sections stained with Mason Trichrome stain performed.

Antibody administration: A 20 mg/kg dose of human ant-rat TIMP-1 antibody or control human antibody (IgG) was administered subcutaneously on day—1. Subsequently, a 10 mg/kg dose of human ant-rat TIMP-1 antibody or control human antibody (IgG) was administered s.c. on days 2, 5, 8, and 11. The following five groups of animals were studied: Saline i.t. challenge+antibody vehicle (PBS); Saline i.t. challenge+TIMP-1 antibody; Bleomycin i.t. challenge+ TIMP-1 antibody; Bleomycin i.t. challenge+antibody vehicle (PBS); Bleomycin i.t. challenge+control antibody.

Figure 14:
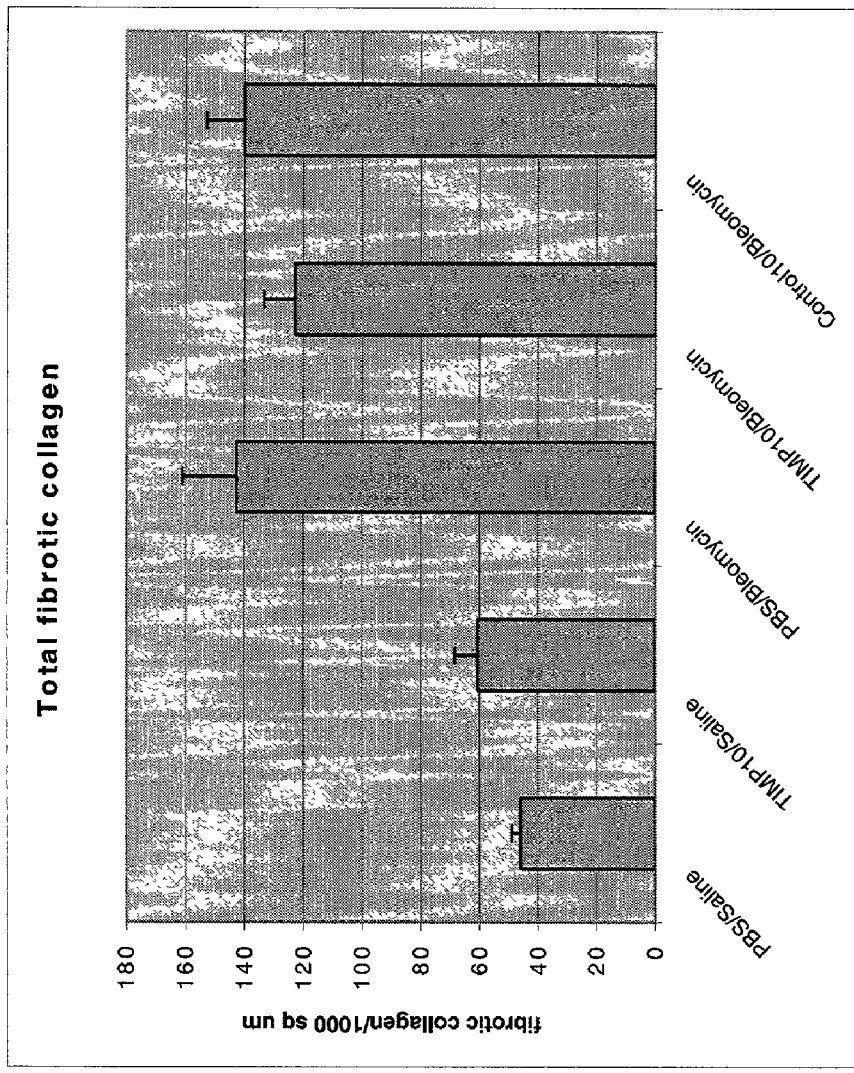
FIG. 14. Effect of the inhibitory effect of MS-BW-17-1 TIMP-1 antibody on bleomycin-induced lung fibrotic collagen.

FIG. 14 shows the effect of the inhibitory effect of TIMP-1 antibody on bleomycin-induced lung fibrotic collagen.

EXAMPLE 24

Effect of BW-14 Anti-TIMP-1 Antibody in a Rat Model with CCl$_4$-Induced Liver Fibrosis Carbon tetrachloride (CCl$_4$) was used to induce liver fibrosis as described in Example 9. A single intravenous dose of 3 mg/kg BW-14 or control antibody BW-3, respectively, was administered on day 19. At this time, total liver collagen (hydroxyproline determined according to Prockop and Udenfried) is already significantly increased by CCl$_4$, and fibrotic collagen rapidly accumulates during the following weeks. The rats were sacrificed on day 28. The treatment groups were: no CCl$_4$+ control antibody BW 3 (n=10 rats), CCl$_4$+control antibody BW 3 (n=20 rats), and CCl$_4$+BW 14 (n=20 rats).

Figure 15:
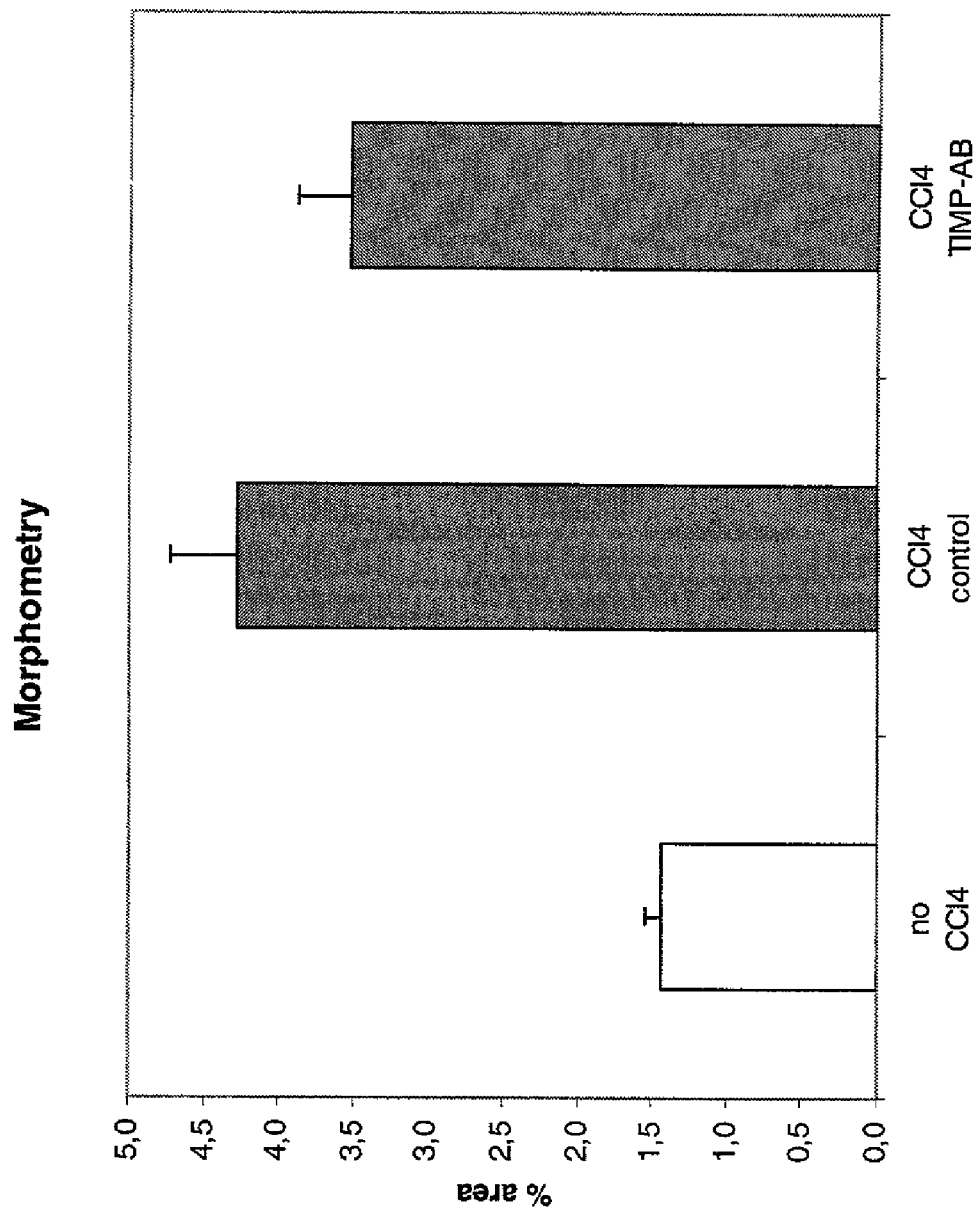
FIG. 15. Effect of anti-TIMP-1 antibody on fibrotic collagen as stained by Sirus Red in carbon tetrachloride-induced rat liver fibrosis model. Sirus Red-stained area as percent of total field in carbon tetrachloride-treated rats treated with PBS, control antibody, and MS-BW-14 anti-TIMP-1 antibody.

The effect of control vs. TIMP-1 antibody as reflected in morphometric measurements of fibrous collagen (Sirius Red stained area as percentage of the total field) is shown in FIG. 15. Comparison of both control antibody treated groups shows that CCl$_4$ caused an approximately three-fold increase in collagen area. BW-14 antibody treatment reduced the pathological collagen increment by 26%. The lower fibrous collagen value of the CCl$_4$+BW-14 group compared to the CCl$_4$+BW-3 group was statistically significant ($p<0.05$, Kolmogorow-Smirnow test).

REFERENCES

Ausubel et al. (1998) Current Protocols in Molecular Biology. Wiley, N.Y., USA.

Better et al., (1988) *Escherichia coli* secretion of an active chimeric antibody fragment. Science 240, 1041.

Bruggeman et al., (1996) Phage antibodies against an unstable hapten: oxygen sensitive reduced flavin. FEBS Lett. 388, 242.

Butler et al., (1999) Human tissue inhibitor of metalloproteinases 3 interacts with both the N- and C-terminal domains of gelatinases A and B. Regulation by polyanions. J Biol Chem. 274, 10846.

Gomis-Ruth et al., (1996). Mechanism of inhibition of the human matrix metalloproteinase stromelysin-1 by TIMP-1. Nature. 389, 77.

Griffiths, A. D. and Duncan, A. R. (1998) Strategies for selection of antibodies by phage display. Curr. Opin. Biotechnol. 9, 102.

Hoogenboom, H. R. and Winter, G. (1992). By-passing immunisation. Human antibodies from synthetic repertoires of germline VH gene segments rearranged in vitro. J. Mol. Biol. 227, 381.

Iredale et al., (1996) Tissue inhibitor of metalloproteinase-1 messenger RNA expression is enhanced relative to interstitial collagenase messenger RNA in experimental liver injury and fibrosis. Hepatology. 24, 176.

Knappik et al., (2000) Fully synthetic human combinatorial antibody libraries (HuCAL) based on modular consensus frameworks and CDRs diversified with trinucleotides. J. Mol. Biol. 296, 55.

Krebs et al., (2001) High-throughput generation and engineering of recombinant human antibodies. J Immunol Methods. 254, 67.

Lowman, H. B. (1997) Bacteriophage display and discovery of peptide leads for drug development. Annu. Rev. Biophys. Biomol. Struct. 26,401.

McCafferty et al., (1990) Phage antibodies: filamentous phage displaying antibody variable domains. Nature 348, 552.

Meng et al., (1999) Residue 2 of TIMP-1 is a major determinant of affinity and specificity for matrix metalloproteinases but effects of substitutions do not correlate with those of the corresponding P1' residue of substrate. J Biol Chem. 274, 10184.

Meulemans et al., (1994) Selection of phage-displayed antibodies specific for a cytoskeletal antigen by competitive elution with a monoclonal antibody. J. Mol. Biol. 244, 353.

Miyazaki et al., (1999) Changes in the specificity of antibodies by site-specific mutagenesis followed by random mutagenesis. Protein Eng. 12, 407.

Sheets et al., (1998) Efficient construction of a large non-immune phage antibody library: The production of high-affinity human single-chain antibodies to protein antigens. Proc. Natl. Acad. Sci. U.S.A. 95, 6157.

Skerra, A. and Plückthun, A. (1988) Assembly of a functional immunoglobulin Fv fragment in *Escherichia coli*. Science 240, 1038.

Smith, G. P. (1985) Filamentous fusion phage: novel expression vectors that display cloned antigens on the virion surface. Science 228, 1315.

Smith, G. P. and Petrenko, V. A. (1997) Phage display. Chem. Rev. 97, 391.

Stausbøl-Grøn et al.(1996) A model phage display subtraction method with potential for analysis of differential gene expression. FEBS Lett. 391, 71.

Virnekäs et al. (1994) Trinucleotide phosphoramidites: ideal reagents for the synthesis of mixed oligonucleotides for random mutagenesis. Nucl. Acids Res. 22, 5600.

The invention claimed is:

1. A purified human antibody, wherein the antibody: binds to a tissue inhibitor of metalloprotease-1 (TIMP-I); neutralizes a matrix metalloprotease (MMP)-inhibiting activity of the TIMP-1; and comprises:
   a VHCDR1 region comprising an amino acid sequence as set forth in SEQ ID NO:355;
   a VHCDR2 region comprising an amino acid sequence as set forth in SEQ ID NO:359;
   a VHCDR3 region comprising an amino acid sequence as set forth in SEQ ID NO:360;
   a VLCDR1 region comprising an amino acid sequence as set forth in SEQ ID NO:363;
   a VLCDR2 region comprising an amino acid sequence as set forth in SEQ ID NO:364; and
   a VLCDR3 region comprising an amino acid sequence as set forth in SEQ ID NO:48.

2. The antibody of claim 1 wherein the MMP is human MMP-1.

3. The antibody of claim 1 wherein the TIMP-1 is a human TIMP-1.

4. The antibody of claim 3 wherein the antibody binds to the human TIMP-1 with a $K_d$ selected from the group consisting of about 0.1 nM to about 10 μM, about 0.2 nM to about 13 nM, and about 0.2 nM to about 0.5 nM.

5. The antibody of claim 3 wherein the antibody binds to the human TIMP-1 with a $K_d$ of about 0.2 nM.

6. The antibody of claim 3 wherein the antibody neutralizes the MMP-inhibiting activity of the human TIMP-1 with an $IC_{50}$ selected from the group consisting of about 0.1 nM to about 200 nM, about 0.2 nM to about 11 nM, and about 0.2 nM to about 4 nM.

7. The antibody of claim 3 wherein the antibody neutralizes the MMP-inhibiting activity of the human TIMP-1 with an $IC_{50}$ of about 0.2 nM.

8. The antibody of claim 3, wherein the antibody binds to human TIMP-1 and neutralizes the MMP-inhibiting activity of the human TIMP-1 with a Kd and an IC50 that are approximately equal.

9. A composition comprising:
   a human purified antibody which (1) binds to a TIMP-1; (2) neutralizes an MMP-inhibiting activity of the TIMP-1; and (3) comprises
   a VHCDR1 region comprising an amino acid sequence as set forth in SEQ ID NO:355;
   a VHCDR2 region comprising an amino acid sequence as set forth in SEQ ID NO:359;
   a VHCDR3 region comprising an amino acid sequence as set forth in SEQ ID NO:360;
   a VLCDR1 region comprising an amino acid sequence as set forth in SEQ ID NO:363;
   a VLCDR2 region comprising an amino acid sequence as set forth in SEQ ID NO:364; and
   a VLCDR3 region comprising an amino acid sequence as set forth in SEQ ID NO:48; and
   a pharmaceutically acceptable carrier.

10. The composition of claim 9 wherein the MMP is human MMP-1.

11. The composition of claim 9 wherein the TIMP-1 is a human TIMP-1.

12. The composition of claim 9, wherein the antibody binds to human TIMP-1 and neutralizes the MMP-inhibiting activity of the human TIMP-1 with a Kd and an IC50 that are approximately equal.

* * * * *